US009095384B2

(12) United States Patent
Robie

(10) Patent No.: US 9,095,384 B2
(45) Date of Patent: Aug. 4, 2015

(54) METHODS, SYSTEMS AND APPARATUSES FOR TORSIONAL STABILIZATION

(75) Inventor: Bruce Robie, Glen Rock, NJ (US)

(73) Assignee: ARO Medical ApS u/stiftelse, Risskov (DK)

( * ) Notice: Subject to any disclaimer, the term of this patent is extended or adjusted under 35 U.S.C. 154(b) by 943 days.

(21) Appl. No.: 12/253,004

(22) Filed: Oct. 16, 2008

(65) Prior Publication Data

US 2009/0105761 A1  Apr. 23, 2009

Related U.S. Application Data

(60) Provisional application No. 60/980,534, filed on Oct. 17, 2007, provisional application No. 61/034,115, filed on Mar. 5, 2008, provisional application No. 61/058,885, filed on Jun. 4, 2008.

(51) Int. Cl.
*A61B 17/88* (2006.01)
*A61B 17/04* (2006.01)
(Continued)

(52) U.S. Cl.
CPC ......... *A61B 17/7067* (2013.01); *A61B 17/1671* (2013.01); *A61B 17/1757* (2013.01);
(Continued)

(58) Field of Classification Search
CPC ........... A61B 17/7071; A61B 17/7073; A61B 17/7076; A61B 17/8861; A61B 2017/0496; A61B 17/0642; A61B 17/7053; A61B 17/7067; A61F 2/4405
USPC ......... 606/228, 232, 233, 246–249, 260, 279, 606/250; 623/17.11–17.16
See application file for complete search history.

(56) References Cited

U.S. PATENT DOCUMENTS 4,570,618 A * 2/1986 Wu ............................... 606/263
4,643,178 A * 2/1987 Nastari et al. .................. 606/74
(Continued)

FOREIGN PATENT DOCUMENTS

DE   20 2006 019649 U1   8/2007
GB        2198043         6/1988
(Continued)

OTHER PUBLICATIONS

International Search Report dated Sep. 22, 2009 for application PCT/US2008/080209.
(Continued)

*Primary Examiner* — Jan Christopher Merene
*Assistant Examiner* — Atiya Mahmud
(74) *Attorney, Agent, or Firm* — Knobbe, Martens, Olson & Bear, LLP.

(57) ABSTRACT

Methods, systems and apparatuses are provided for torsionally stabilizing a spinal motion segment. One or more implants are placed between two vertebrae to provide torsional stabilization. In particular, one or more implants may be fixed between a superior vertebral body, such as at the spinous process, and an inferior vertebral body. The implants may be connected to the superior vertebral body using a fixation device such as a turnbuckle, an outrigger, a thimble, an endobutton, a suture plug or combinations thereof. The implant may also be connected to the inferior vertebral body using various types of hardware, including staples, screws and anchors. The implant may be kept in tension to provide torsional stabilization and may be comprised of one or more sutures. A multi-functional instrument having one or more arms having holes can be used to clamp onto the superior vertebral body and guide one or more implants to various locations for fixation in accordance with the methods described herein.

24 Claims, 49 Drawing Sheets

(51) Int. Cl.
*A61B 17/70* (2006.01)
*A61B 17/17* (2006.01)
*A61B 17/064* (2006.01)
*A61B 17/16* (2006.01)
*A61B 17/34* (2006.01)
*A61B 19/00* (2006.01)

(52) U.S. Cl.
CPC ......... *A61B17/7053* (2013.01); *A61B 17/8863* (2013.01); *A61B 17/0401* (2013.01); *A61B 17/0469* (2013.01); *A61B 17/0485* (2013.01); *A61B 17/0487* (2013.01); *A61B 17/0642* (2013.01); *A61B 17/1604* (2013.01); *A61B 17/1606* (2013.01); *A61B 17/1664* (2013.01); *A61B 17/1675* (2013.01); *A61B 17/1684* (2013.01); *A61B 17/3421* (2013.01); *A61B 17/8861* (2013.01); *A61B 19/26* (2013.01); *A61B 2017/0404* (2013.01); *A61B 2017/044* (2013.01); *A61B 2017/0409* (2013.01); *A61B 2017/0414* (2013.01); *A61B 2017/0458* (2013.01); *A61B 2017/0496* (2013.01); *A61B 2019/461* (2013.01)

(56) References Cited

U.S. PATENT DOCUMENTS

| | | | |
|---|---|---|---|
| 5,306,275 A | | 4/1994 | Bryan |
| 5,413,579 A * | | 5/1995 | Tom Du Toit .................. 606/87 |
| 5,534,011 A | | 7/1996 | Green et al. |
| 5,628,756 A * | | 5/1997 | Barker et al. ................ 606/139 |
| 5,733,284 A | | 3/1998 | Martin |
| 5,814,070 A | | 9/1998 | Borzone et al. |
| 5,989,256 A | | 11/1999 | Kuslich et al. |
| 6,132,464 A | | 10/2000 | Martin |
| 6,168,598 B1 | | 1/2001 | Martello |
| 6,264,677 B1 | | 7/2001 | Simon et al. |
| 6,358,254 B1 * | | 3/2002 | Anderson ..................... 606/103 |
| 6,547,795 B2 | | 4/2003 | Schneiderman |
| 6,589,243 B1 * | | 7/2003 | Viart et al. .................... 606/250 |
| 6,610,080 B2 | | 8/2003 | Morgan |
| 6,610,091 B1 | | 8/2003 | Reiley |
| 6,719,795 B1 | | 4/2004 | Cornwall et al. |
| 6,773,436 B2 | | 8/2004 | Donnelly et al. |
| 6,843,799 B2 | | 1/2005 | Bartlett |
| 6,860,884 B2 | | 3/2005 | Shirado et al. |
| 6,974,478 B2 | | 12/2005 | Reiley et al. |
| 7,041,136 B2 | | 5/2006 | Goble et al. |
| 7,074,237 B2 | | 7/2006 | Goble et al. |
| 7,074,238 B2 | | 7/2006 | Stinson et al. |
| 7,090,698 B2 | | 8/2006 | Goble et al. |
| 7,163,540 B2 | | 1/2007 | Martello |
| 7,799,057 B2 | | 9/2010 | Hudgins et al. |
| 7,998,176 B2 * | | 8/2011 | Culbert ......................... 606/279 |
| 2002/0120292 A1 | | 8/2002 | Morgan |
| 2003/0040746 A1 | | 2/2003 | Mitchell et al. |
| 2005/0033434 A1 | | 2/2005 | Berry |
| 2005/0049705 A1 | | 3/2005 | Hale et al. |
| 2005/0058790 A1 | | 3/2005 | Reilley et al. |
| 2005/0090827 A1 | | 4/2005 | Gedebou |
| 2005/0143818 A1 * | | 6/2005 | Yuan et al. .................. 623/17.11 |
| 2005/0288672 A1 * | | 12/2005 | Ferree ............................ 606/61 |
| 2006/0004367 A1 * | | 1/2006 | Alamin et al. ................. 606/74 |
| 2006/0036259 A1 * | | 2/2006 | Carl et al. ...................... 606/90 |
| 2006/0036324 A1 | | 2/2006 | Sachs et al. |
| 2006/0058790 A1 * | | 3/2006 | Carl et al. ...................... 606/61 |
| 2006/0064166 A1 * | | 3/2006 | Zucherman et al. ....... 623/17.11 |
| 2006/0084991 A1 * | | 4/2006 | Borgstrom et al. ............. 606/61 |
| 2006/0085069 A1 * | | 4/2006 | Kim ............................ 623/17.11 |
| 2006/0089646 A1 * | | 4/2006 | Bonutti ........................... 606/61 |
| 2006/0149375 A1 | | 7/2006 | Yuan et al. |
| 2006/0190081 A1 * | | 8/2006 | Kraus et al. ................. 623/17.11 |
| 2006/0241613 A1 * | | 10/2006 | Bruneau et al. ................ 606/69 |
| 2006/0282076 A1 | | 12/2006 | Labrom et al. |
| 2006/0293663 A1 | | 12/2006 | Walkenhorst et al. |
| 2007/0016191 A1 | | 1/2007 | Culbert et al. |
| 2007/0055236 A1 * | | 3/2007 | Hudgins et al. ................ 606/61 |
| 2007/0055373 A1 | | 3/2007 | Hudgins et al. |
| 2007/0088358 A1 | | 4/2007 | Yuan et al. |
| 2007/0123868 A1 | | 5/2007 | Culbert et al. |
| 2007/0142837 A1 * | | 6/2007 | Dreyfuss ........................ 606/73 |
| 2007/0156237 A1 * | | 7/2007 | Kwak ........................ 623/13.14 |
| 2007/0162000 A1 | | 7/2007 | Perkins |
| 2007/0162005 A1 * | | 7/2007 | Peterson et al. ................ 606/61 |
| 2007/0168035 A1 * | | 7/2007 | Koske ........................ 623/17.13 |
| 2007/0173818 A1 * | | 7/2007 | Hestad et al. ................... 606/61 |
| 2007/0185492 A1 | | 8/2007 | Chervitz et al. |
| 2007/0191834 A1 | | 8/2007 | Bruneau et al. |
| 2007/0198091 A1 | | 8/2007 | Boyer et al. |
| 2007/0233077 A1 | | 10/2007 | Khalili |
| 2007/0233093 A1 * | | 10/2007 | Falahee ........................... 606/61 |
| 2007/0233189 A1 | | 10/2007 | Pedlick et al. |
| 2007/0255411 A1 | | 11/2007 | Reiley |
| 2007/0270822 A1 * | | 11/2007 | Heinz ............................. 606/61 |
| 2007/0276500 A1 * | | 11/2007 | Zuckerman et al. ........ 623/17.16 |
| 2008/0015585 A1 * | | 1/2008 | Berg et al. ...................... 606/61 |
| 2008/0082172 A1 * | | 4/2008 | Jackson ..................... 623/17.16 |
| 2008/0114358 A1 * | | 5/2008 | Anderson et al. .............. 606/64 |
| 2008/0154262 A1 | | 6/2008 | Brundobler et al. |
| 2008/0195148 A1 * | | 8/2008 | Cook et al. .................... 606/232 |
| 2008/0215094 A1 * | | 9/2008 | Taylor ........................... 606/246 |
| 2008/0306537 A1 | | 12/2008 | Culbert |
| 2011/0106163 A1 * | | 5/2011 | Hochschuler et al. ........ 606/264 |

FOREIGN PATENT DOCUMENTS

| | | |
|---|---|---|
| WO | WO 90/04948 | 5/1990 |
| WO | WO 98/48717 A | 11/1998 |
| WO | WO 2005/037150 | 4/2005 |
| WO | WO 2005/112835 | 12/2005 |
| WO | WO 2006/102443 A | 9/2006 |

OTHER PUBLICATIONS

Bardana, Davide et al., "The Effect of Suture Anchor Design and Orientation on Suture Abrasion: An In Vitro Study", *Arthroscopy: The Journal of Arthroscopic and Related Surgery*, vol. 19, No. 3, pp. 274-281 (Mar. 2003).

Crossman, John et al., "Recurrent Atlantoaxial Rotatory Fixation in Children: A Rare Complication of a Rare Condition", *J. Neurosurg: Spine*, vol. 100, pp. 307-311 (Mar. 2004).

Salib, Richard et al., "Modified Repair of a Defect in Spondylolysis or Minimal Spondylolisthesis by Pedicle Screw, Segmental Wire Fixation, and Bone Grafting," *Spine*, vol. 18, No. 4, pp. 440-443 (1993).

Partial International Search Report for PCT/US2008/080209 mailed Mar. 10, 2009.

Written Opinion of International Searching Authority dated Sep. 22, 2009 for application PCT/US2008/080209.

Office Action dated Oct. 26, 2011 from European Patent Application No. 08839681.7.

Office Action dated Nov. 29, 2012 from European Patent Application No. 08839681.7.

Jul. 4, 2014 European Search Report and Written Opinion for Application No. 13191484.8 filed on Nov. 4, 2013.

* cited by examiner

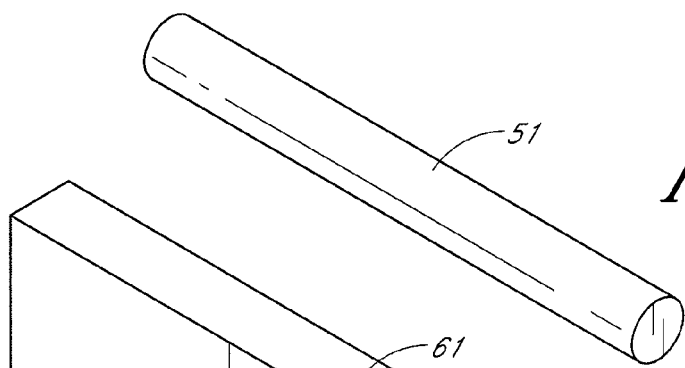
FIG. 5
FIG. 6
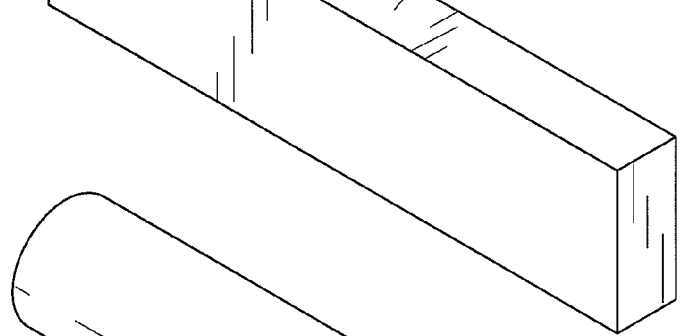
FIG. 7A
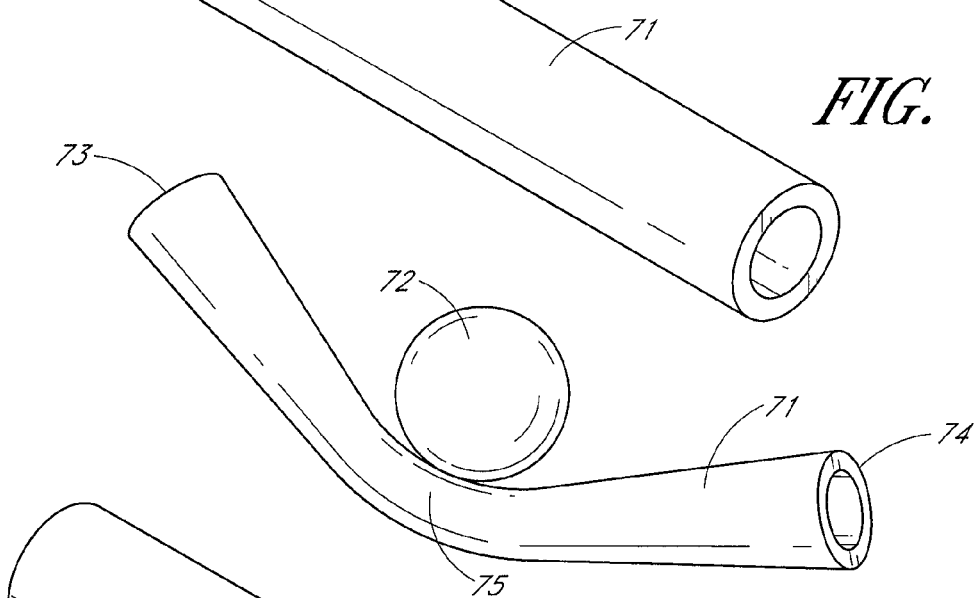
FIG. 7B
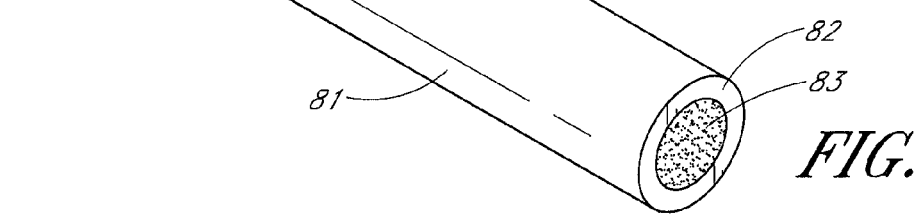
FIG. 8

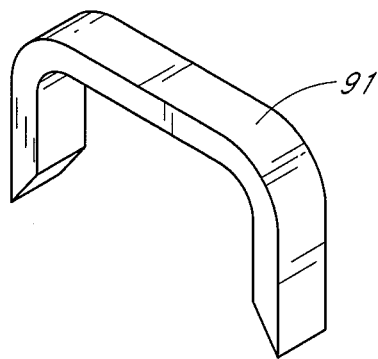
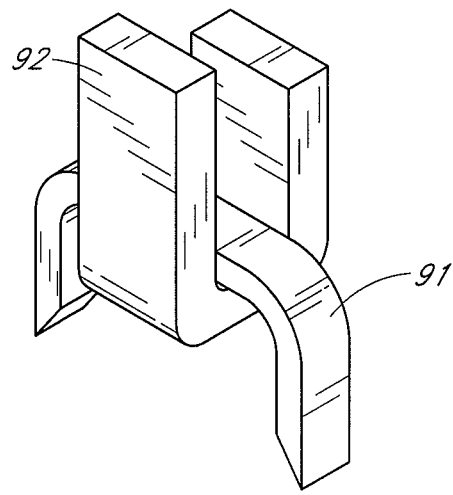
*FIG. 9A*  *FIG. 9B*
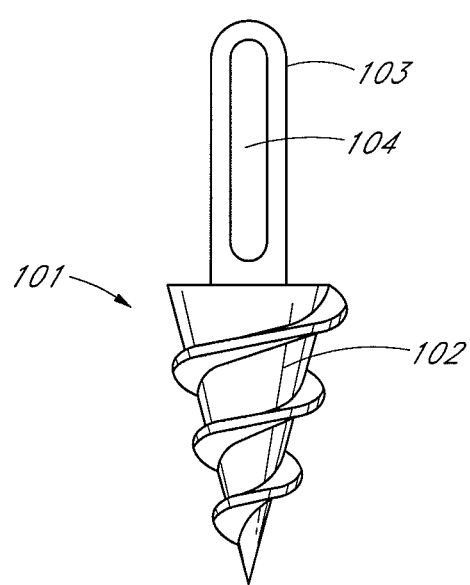
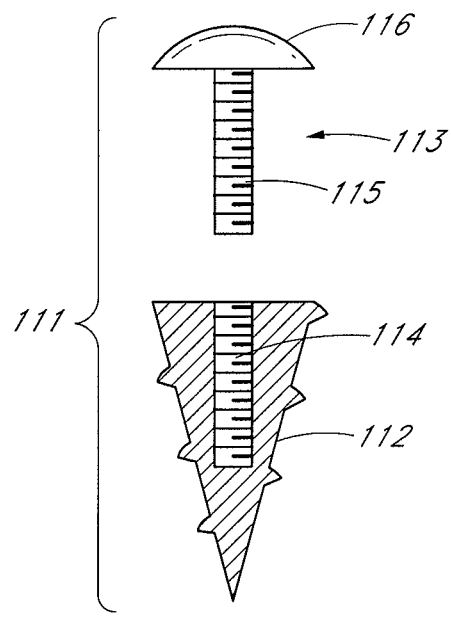
*FIG. 10*  *FIG. 11*

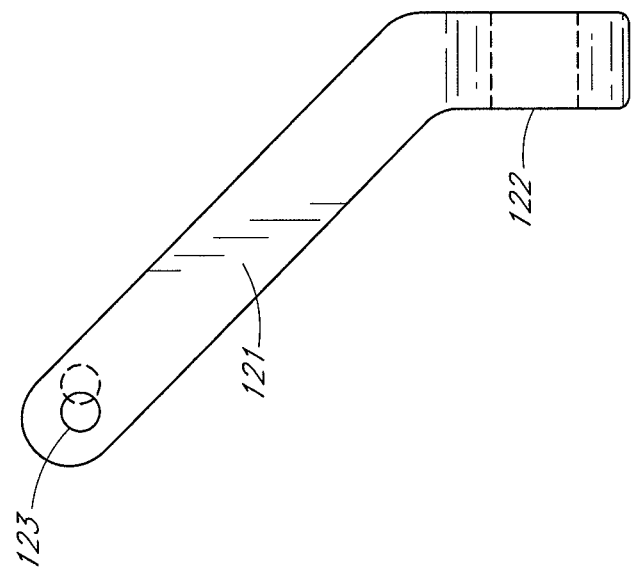
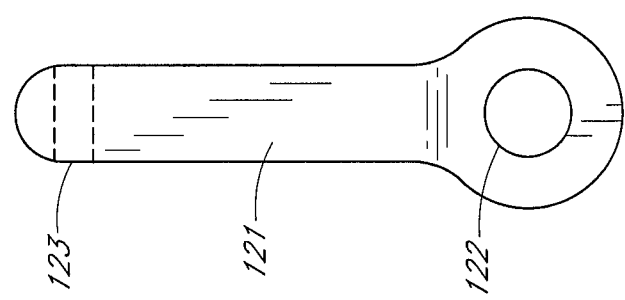
FIG. 12B
FIG. 12A

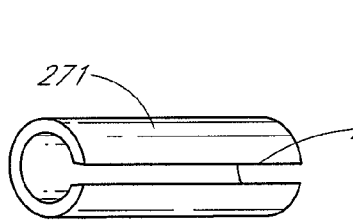
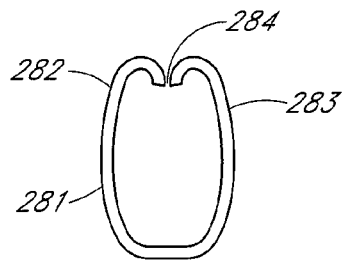
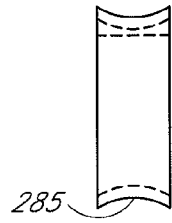
FIG. 27    FIG. 28A    FIG. 28B
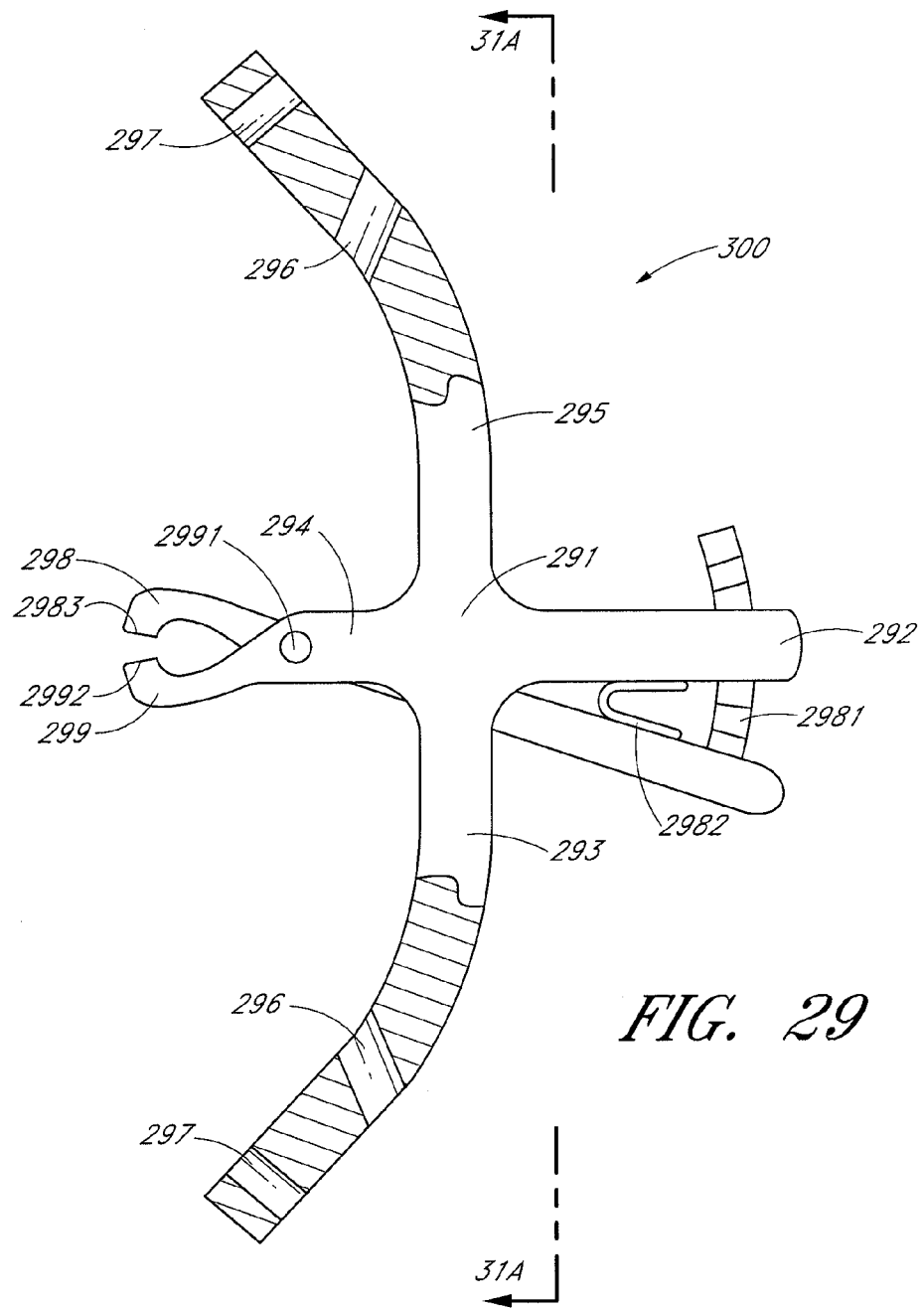
FIG. 29

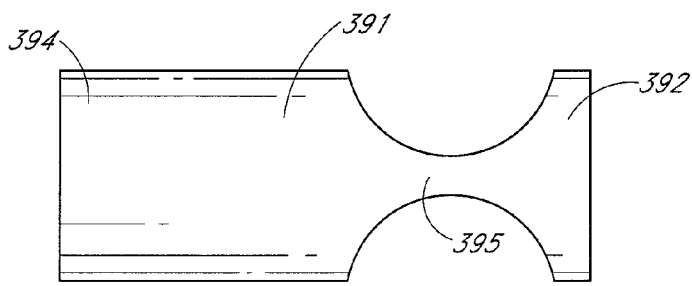
*FIG. 40A*
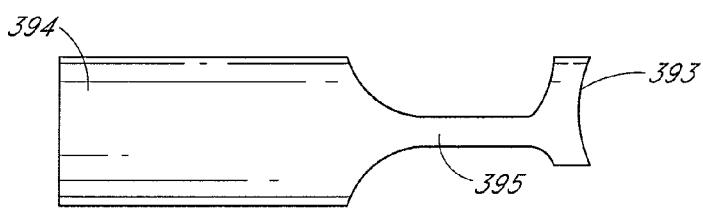 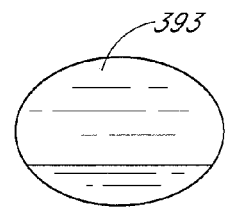
*FIG. 40B*    *FIG. 40C*
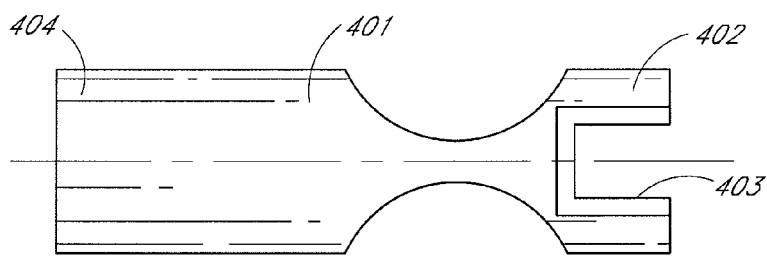
*FIG. 41A*
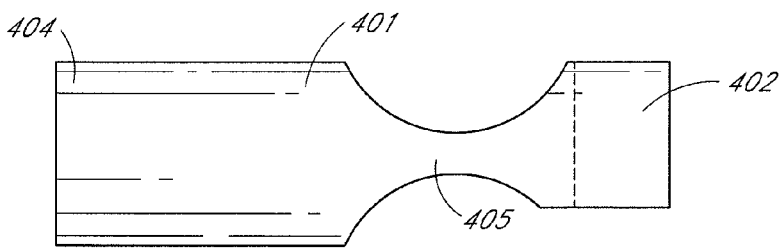 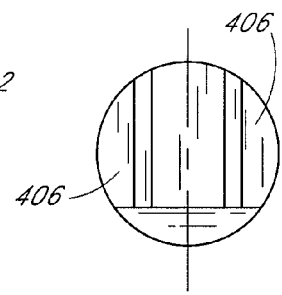
*FIG. 41B*    *FIG. 41C*

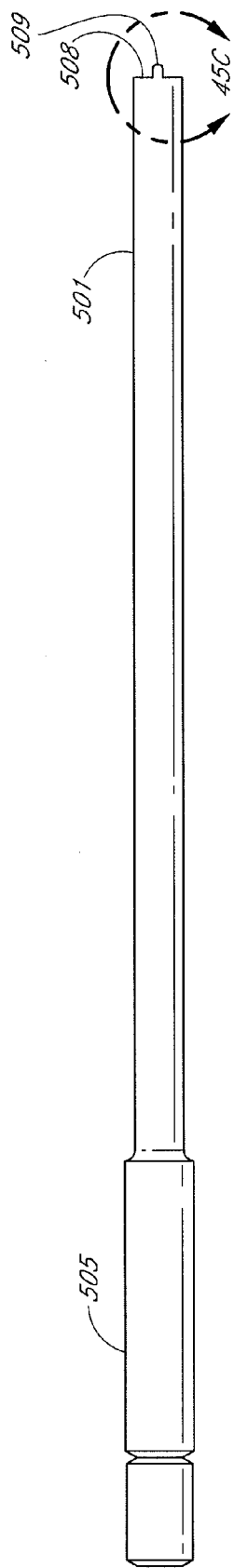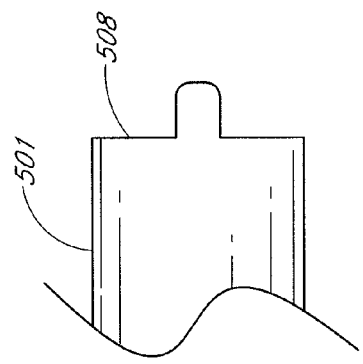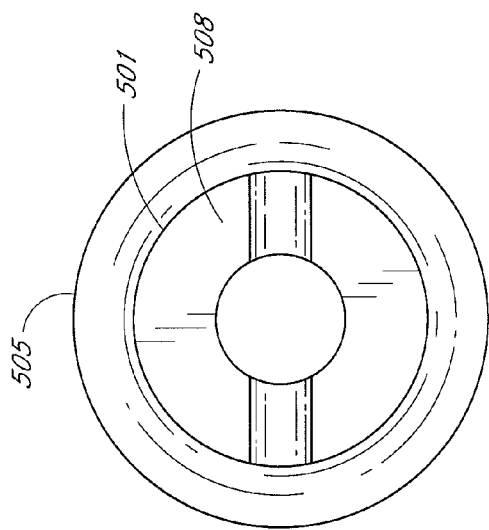
FIG. 45A
FIG. 45C
FIG. 45B

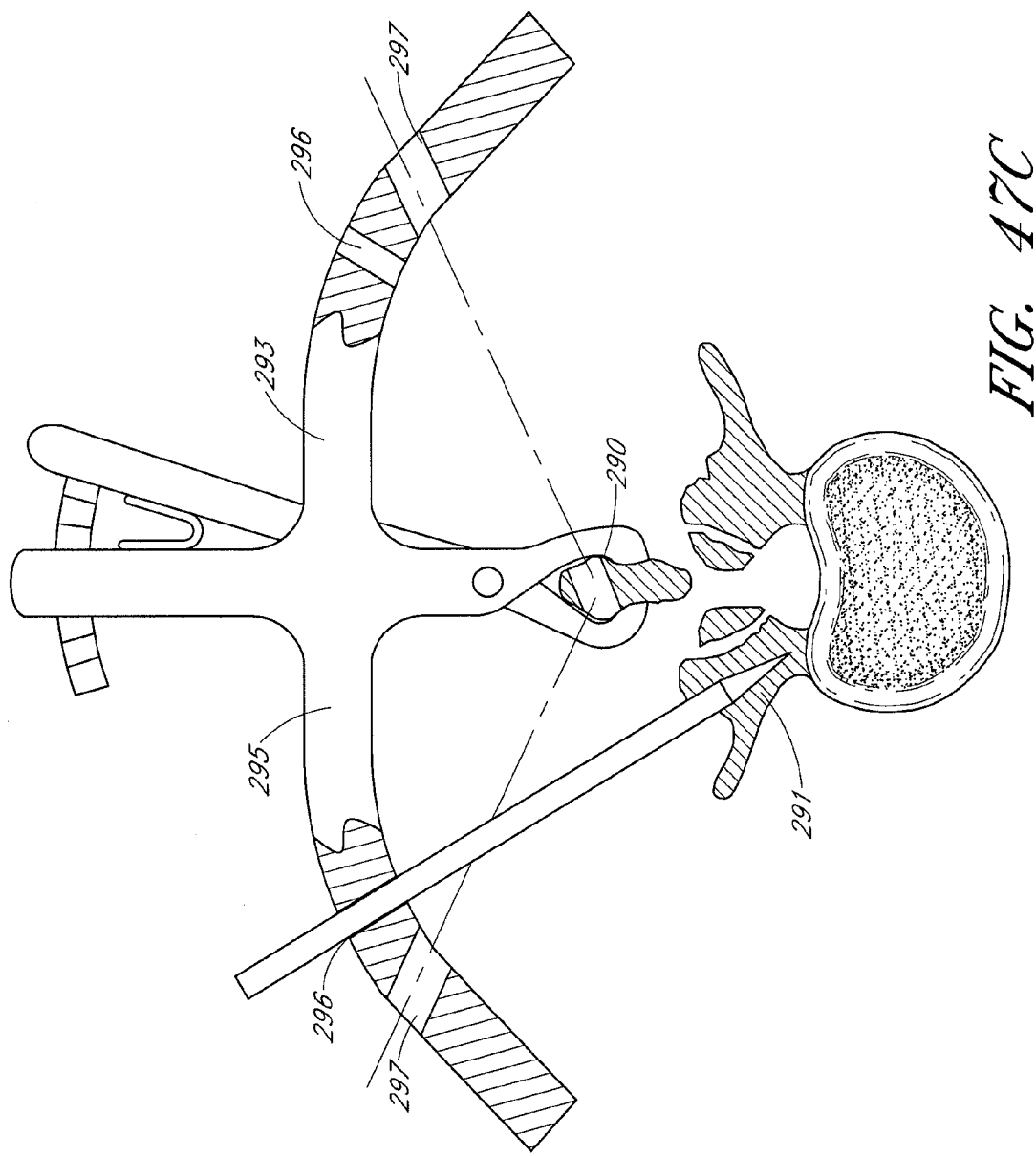

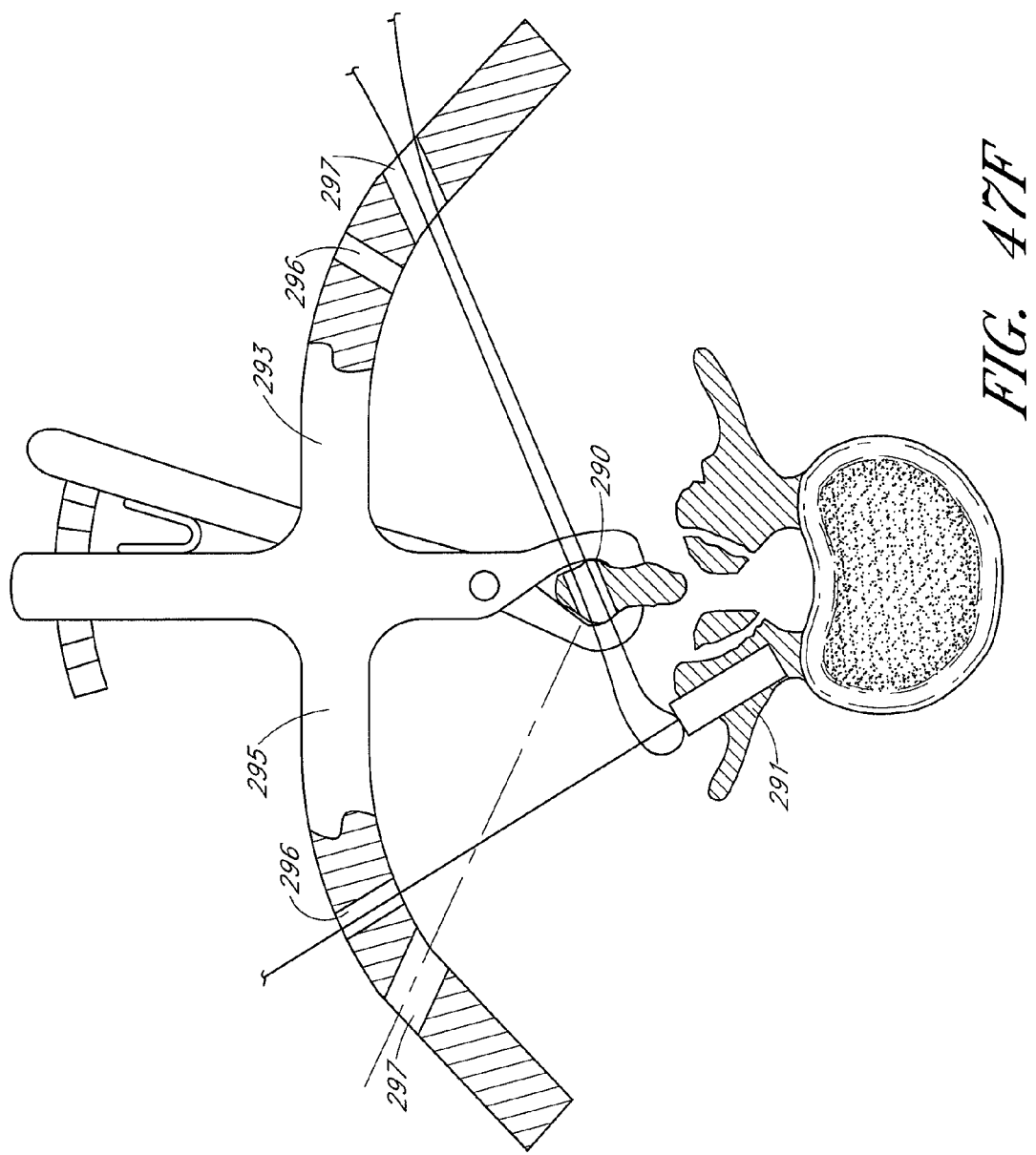

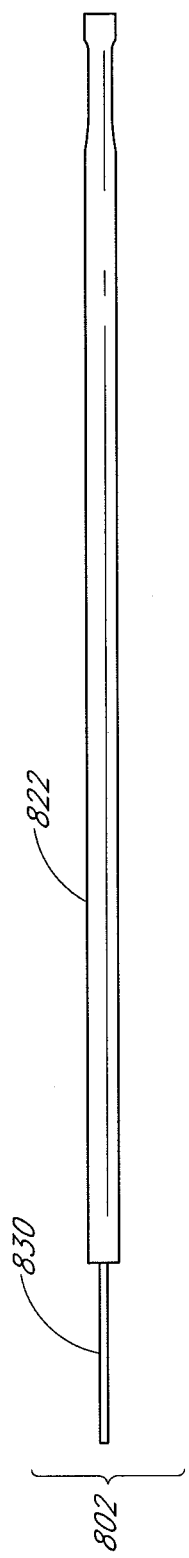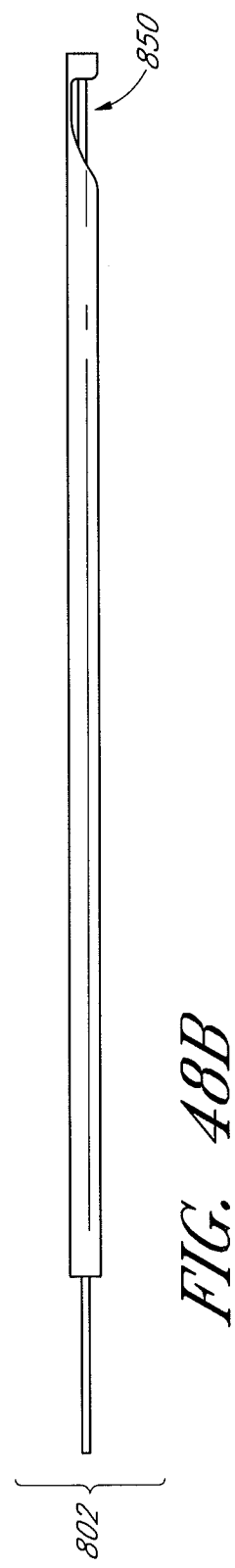
FIG. 48A
FIG. 48B

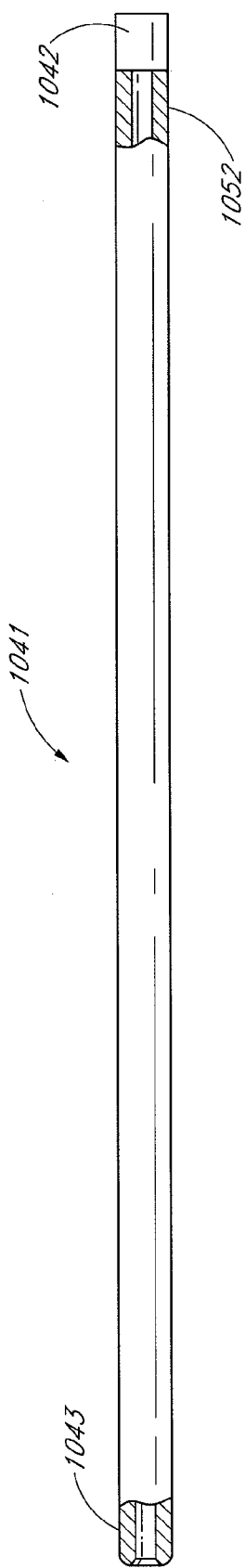
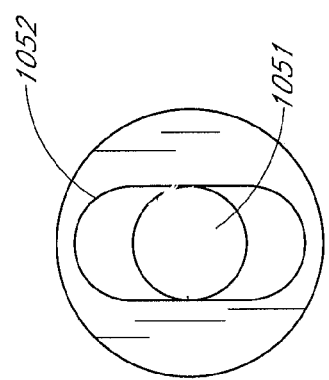
FIG. 55
FIG. 56

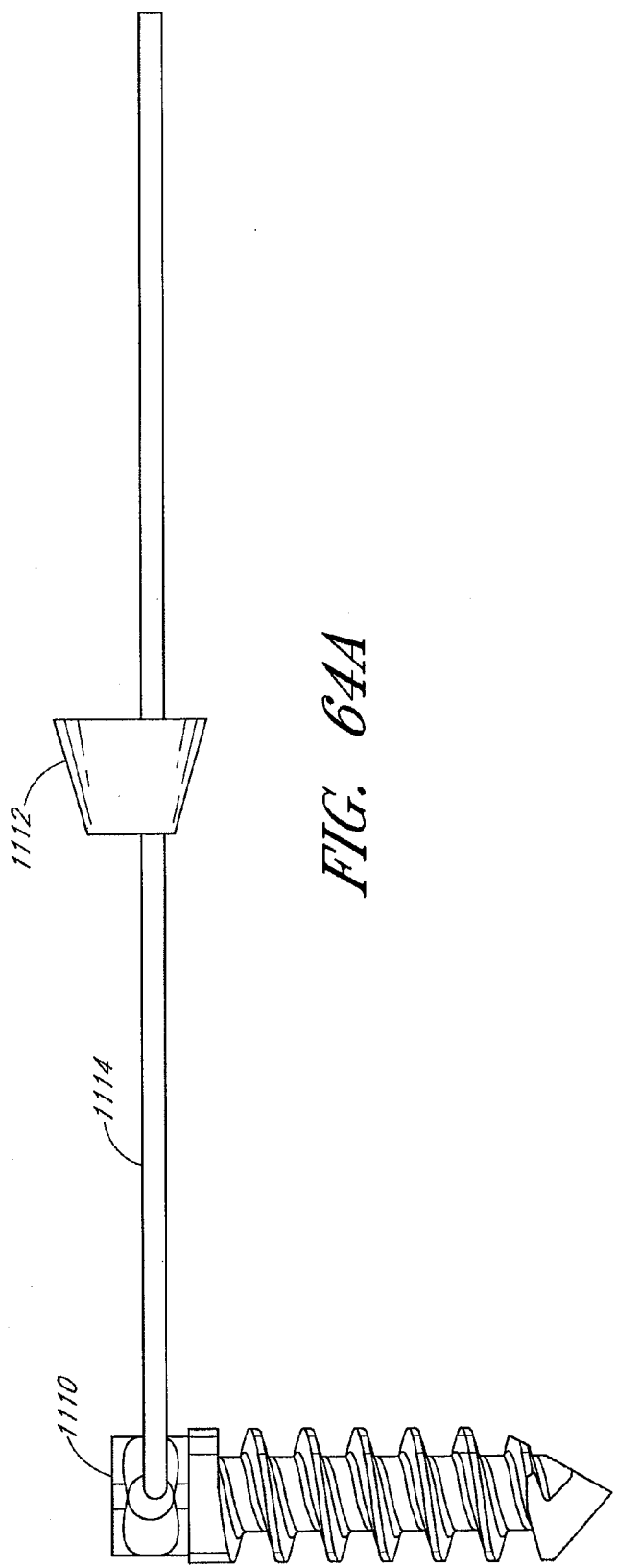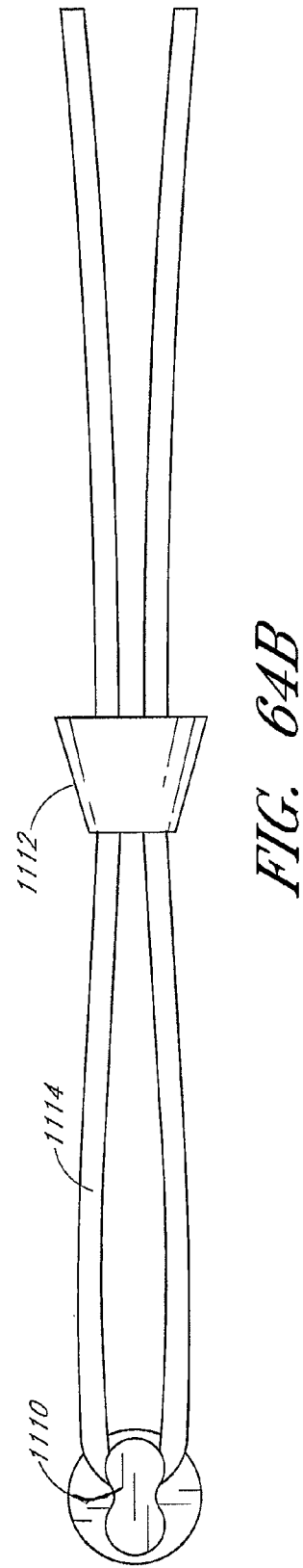

METHODS, SYSTEMS AND APPARATUSES FOR TORSIONAL STABILIZATION

The present application claims priority under 35 U.S.C. §119(e) to U.S. Provisional Patent Application Ser. No. 60/980,534, entitled "Torsionally Resistive Spinal Implants and Methods," filed Oct. 17, 2007, U.S. Provisional Patent Application Ser. No. 61/034,115, entitled "Torsionally Resistive Spinal Implants and Methods," filed Mar. 5, 2008, and U.S. Provisional Patent Application Ser. No. 61/058,885, entitled "Torsionally Resistive Spinal Implants and Methods," filed Jun. 4, 2008. The entire disclosures of all the priority applications are hereby expressly incorporated by reference in their entireties.

BACKGROUND OF THE INVENTION

1. Field of the Invention

The present application relates to methods, systems and apparatuses to torsionally stabilize a spinal motion segment.

2. Description of the Related Art

In many patients, an early finding associated with back pain is a weakening or disruption of the annulus. Patients in this state may then be treated with either micro- or open discectomy to remove any fragments associated with pain. Typically, these patients do well in the short term, but eventually have degeneration leading to axial (back or neck) pain, sometimes also in the presence of radicular pain, radicular weakness or a loss of sensation radicularly.

In patients with low back pain generally, including those without disruption of the annulus, there is known to be excessive axial rotation, as recently shown by Haughton et al., Measuring the Axial Rotation of Lumbar Vertebrae in Vivo with MR, Am J Neuroradiol 23: 1110-1116, August 2002. Also, scoliosis patients are known to have changes in the multifidus, which is a significant contributor to spinal stabilization and is a significant generator of axial rotation. In both the population of patients with low back pain, and in scoliosis patients, there may be benefit to a device that increases the stability of the segment(s).

Mechanically, the annulus is a significant structure. In the lumbar spine, the annulus is reported to be on the order of 10 mm thick in the anterior half of the body, but perhaps less than 5 mm posteriorly. As such, it can represent 40 to 60% of the overall area of the endplate. It is known to resist compression, tension, flexion/extension, lateral bending and axial rotation.

With weakening or disruption of the annulus, mechanical changes in the annulus' behavior are expected. It is of value to consider the mechanical impact of annular defects in the different loading directions.

The compression and tension behavior of the annulus is determined by the material properties of the annulus and the annulus' cross-sectional area. The size of the annular defect is a relatively small percentage of the overall annulus. For example, a 10 mm diameter defect in an annulus only represents 8% of the overall annular area. As such, an annular defect has a modest impact on the area, and therefore, the compressive and tensile load carrying capacity of the motion segment.

In flexion/extension or lateral bending motions, the structural behavior of the motion segment is related to the moment of inertia of the annulus. Like tension/compression, the annulus is a significant contributor, and the effect of a defect has a relatively modest impact. Calculations show that an annular defect reduces the moment of inertia of the annulus by only 10%.

In torsion, the structural behavior of the motion segment is related to the polar moment of inertia of the annulus. Using an approximation of a hollow circular cylinder for the annulus, the impact of a hole in the annulus reduces the polar moment of inertia on the order of 90%, and greatly influences the torsional stiffness of the spine. It is therefore desirable to provide systems, methods and apparatuses that may effectively help stiffen motion segment(s) torsionally.

SUMMARY OF THE INVENTION

The present application relates to methods, systems and apparatuses for providing torsional stabilization of a spinal motion segment. More specifically, these methods, systems and apparatuses are related to stabilizing the spine torsionally by placing an implant between adjacent vertebral bodies. In some embodiments, one or more implants are oriented in a plane generally aligned with the disc space, so as to stiffen a motion segment torsionally. The stabilizing implant may comprise a single entity or two or more pieces.

Methods described permit the surgeon to install hardware at two, or preferably three locations, generally aligned with the disc space, and to pass one or more implants between the locations, so as to treat a single spinal level. A single spinal level is defined as a disc space, the vertebral body above the disc space and the vertebral body below the disc space. Preferred fixation on the superior vertebral body is to the spinous process and is the sole point of fixation on the superior vertebral body. Preferred fixation on the inferior vertebral body is bilateral, though fixation could be unilateral.

Systems for providing torsional stabilization to a spine are provided. In one embodiment, a system comprises at least one implant configured to extend between a superior vertebral body and an inferior vertebral body oriented in a plane generally aligned with the disc space to provide torsional stiffness to the spine. A first fixation device is configured to fix the one or more implants to the inferior vertebral body. A second fixation device is configured to fix the one or more implants to the spinous process of the superior vertebral body. To assist with aligning the first and second fixation devices to desired locations, the system also includes a clamping mechanism configured to attach to the spinous process of the superior vertebral body. The clamping mechanism comprises one or more arms, said one or more harms having one or more holes oriented to align with a location desirable for attaching the first and second fixation devices.

Methods for providing torsional stabilization to a spine are provided. In one embodiment, a surgical instrument is clamped to the spinous process, wherein the surgical instrument comprises a clamping mechanism for attachment to the spinous process and one or more arms, each arm having one or more alignment holes oriented to align with a location desirable for attaching one or more fixation devices. A hole may then be created in the spinous process of the superior vertebral body through a first alignment hole of the surgical instrument aligned with a desired location on the spinous process of the superior vertebral body. A stabilizing implant may then be inserted through a second alignment hole aligned to a desired location on an inferior vertebral body and a first portion of the stabilizing implant fixed to a desired location of the inferior vertebral body. The stabilizing implant may then be captured through the created hole in the spinous process and pulled towards the spinous process where it may be attached.

In another embodiment, a method for providing torsional stabilization to a spine comprises extending an implant in tension between a first vertebral body and a second vertebral body, the implant being attached to a fixation device engaged to the spinous process of the second vertebral body and extending laterally outwardly to attach to a location on the first vertebral body.

In another embodiment, a method for providing torsional stabilization to a spine comprises creating a hole through the spinous process of a superior vertebral body. A suture may then be attached to a first location on an inferior vertebral body. The suture may be extended from the inferior vertebral body to the spinous process of the superior vertebral body along a plane generally aligned with the disc space and secured to the spinous process of the superior vertebral body via an endobutton secured to the hole in the spinous process, wherein the suture is placed in tension to provide torsional stabilization.

Novel instruments are provided that enable the surgeon to prepare two or more locations for fixation, to pass one or more stabilizing implants between the different locations, to tighten the stabilizing implants and/or to fix the stabilizing implants to various hardware. In one embodiment, a surgical instrument is provided for delivering hardware to the spine comprising a clamping mechanism configured to be inserted into a patient and attached to the spinous process of a first vertebral body and at least one arm extending laterally outwardly from the clamping mechanism and configured to be positioned outside of the patient. The at least one arm has at least one hole oriented to align with a location on either the spinous process of the first vertebral body or a lateral location on a second vertebral body, the at least one hole being configured to guide an instrument to either the spinous process or to the lateral location on the second vertebral body.

Apparatuses are provided comprising a suture anchor loaded with one or more sutures. The suture anchor comprises a threaded shaft and a suture head connected to the threaded shaft. The threaded shaft comprises an eyelet hole and a rounded post, wherein the eyelet hole transitions smoothly into the rounded post, and wherein one or more sutures loaded to the suture anchor make contact with the suture anchor only via the rounded post.

Various other systems, methods and apparatuses are contemplated and discussed below. While the systems, methods and apparatuses are described with respect to torsional stabilization of the spine, many of the novel embodiments herein can be used for the stabilization of other areas of the body, and may be used for other applications, including non-spinal applications.

BRIEF DESCRIPTION OF THE DRAWINGS

FIG. 5 shows an implant having a rounded cross-section according to one embodiment.
FIG. 6 shows an implant having a rectangular cross-section according to one embodiment.
FIG. 7A shows a tubular implant according to one embodiment.
FIG. 7B shows the effect of a compliant tubular implant when passing around a piece of bone.
FIG. 8 shows a filled tubular implant according to one embodiment.
FIG. 9A shows a staple which can function as an anchor according to one embodiment.
FIG. 9B shows a staple assembled to an implant according to one embodiment.
FIG. 10 shows a front view of an anchor including a bone anchoring portion and an implant receiving portion according to one embodiment.
FIG. 11 shows an exploded front view of an anchor including a bone anchoring component and an implant attachment post according to one embodiment.
FIG. 12A shows a front view of an offset anchor according to one embodiment.
FIG. 12B shows a side view of the offset anchor of FIG. 12A.
FIG. 27 shows an alternative clamp according to one embodiment.
FIG. 28A shows a front view of a thimble.
FIG. 28B shows a side view of the thimble of FIG. 28A.

FIG. 29 shows a top view of a multi-functional surgical instrument according to one embodiment.

FIG. 40A shows a side view of an inserter.

FIG. 40B shows a top view of an inserter.

FIG. 40C shows a front view of an inserter.

FIG. 41A shows a side view of an alternative inserter.

FIG. 41B shows a top view of the alternative inserter of FIG. 41A.

FIG. 41C shows a front view of the alternative inserter of FIG. 41A.

FIG. 45A shows a side view of an anchor driver according to one embodiment.

FIG. 45B shows a cross-sectional top view of the tip of the anchor driver of FIG. 45A.

FIG. 45C shows an exploded side view of the tip of the anchor driver of FIG. 45A.

FIG. 47A-J show the illustrated steps of one embodiment of a surgical method using a multi-functional surgical tool and an endobutton.

FIG. 48A shows a side view of a measuring instrument assembly according to one embodiment.

FIG. 48B shows a front view of the measuring instrument assembly in FIG. 48A.

FIG. 55 is a side view of a suture anchor inserter according to one embodiment.

FIG. 56 is a cross-sectional top view of the suture anchor inserter of FIG. 55.

FIG. 64A shows a side view of a suture anchor and suture plug using a single suture according to one embodiment.

FIG. 64B shows a top view of the suture anchor and suture plug of FIG. 64A

DETAILED DESCRIPTION OF THE PREFERRED EMBODIMENTS

Methods, systems and apparatuses are provided in certain embodiments of the present application to selectively stabilize the spine torsionally by placing one or more implants between adjacent vertebral bodies generally aligned with the disc space, so as to stiffen a motion segment torsionally One procedure of the present application permits the surgeon to install hardware at two or preferably three locations aligned generally with the disc space as fixation devices, and to pass one or more implants between the locations, so as to treat a single spinal level. Novel instruments enable the surgeon to prepare locations for fixation, to pass one or more stabilizing implants between locations, to tighten the stabilizing implants and to fix the stabilizing implants to hardware.

Figure 1:
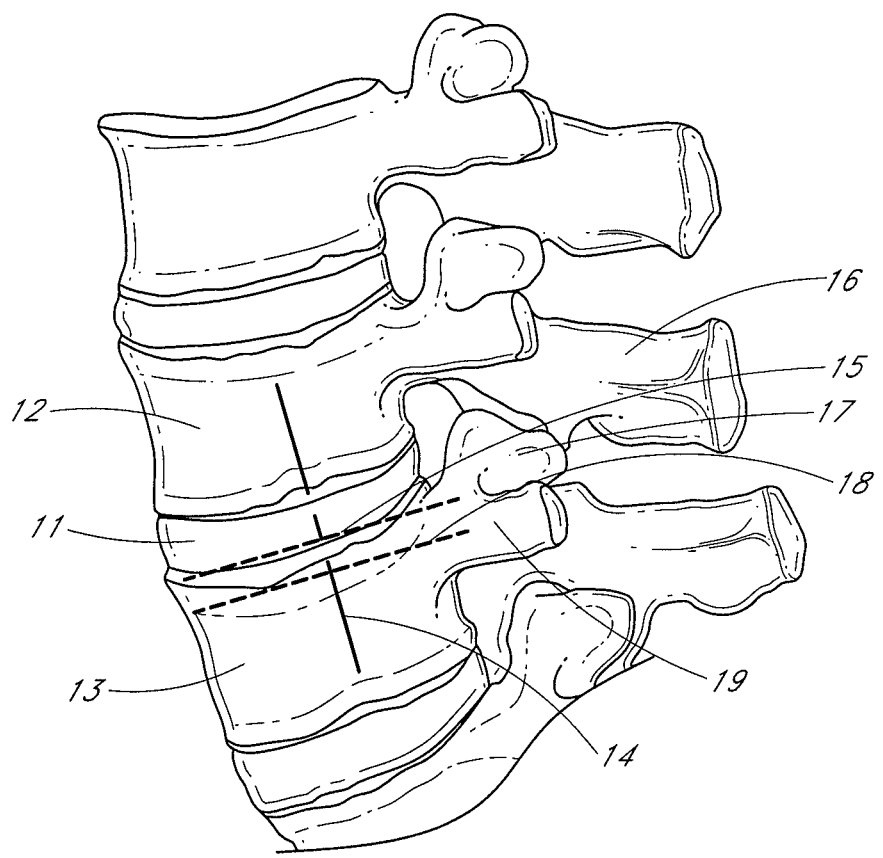
FIG. 1 shows a sagittal (side) view of the lumbar spine.

FIG. 1 shows a sagittal view of the lumbar spine. The present application involves treatment of one or more spinal levels to provide torsional stability. A single spinal level is composed of a disc 11 targeted for treatment, a superior vertebral body 12, and an inferior vertebral body 13.

To provide torsional stabilization without significantly impacting the flexion/extension or lateral bending motion of spinal segments (which may be referred to as "selective" torsional stabilization), the locations to fix the implants preferably lie generally in a plane perpendicular to the torsional axis of rotation 14 of the disc 11. The torsional axis of rotation 14 is aligned with the long axis of the spine. Any plane generally perpendicular to the torsional axis of rotation 14 is defined as being aligned with the disc space. One generally preferred plane 15 shown in FIG. 1 passes through the spinous process 16 of the superior vertebral body 12, and the mamillary process 17 of the inferior vertebral body 13. An alternative plane 18 passes through the pedicle 19 of the inferior vertebral body 13 but does not pass through any part of the superior vertebral body 12. To provide selective torsional stabilization in the alternative plane 18, a fixation device, such as an anchor, may be attached to the spinous process 16 of the superior vertebral body 12 and one or more implants may be fixed inferior to the spinous process 16.

Figure 2:
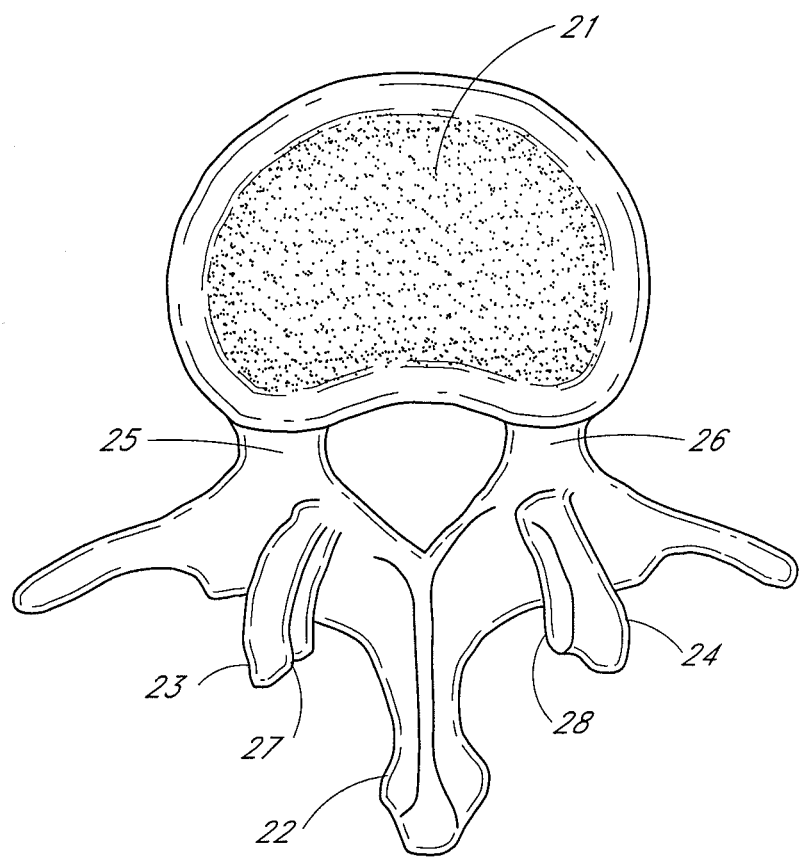
FIG. 2 shows a top view of a lumbar vertebral body.

FIG. 2 shows a top view of a lumbar vertebral body 21. In this view, it is possible to identify the spinous process 22, the mamillary processes 23 and 24 and the pedicles 25 and 26. It can be seen in this view that an implant passing generally between the mamillary processes 23 and 24 to the spinous process would pass adjacent to the facets 27 and 28.

Figure 3:
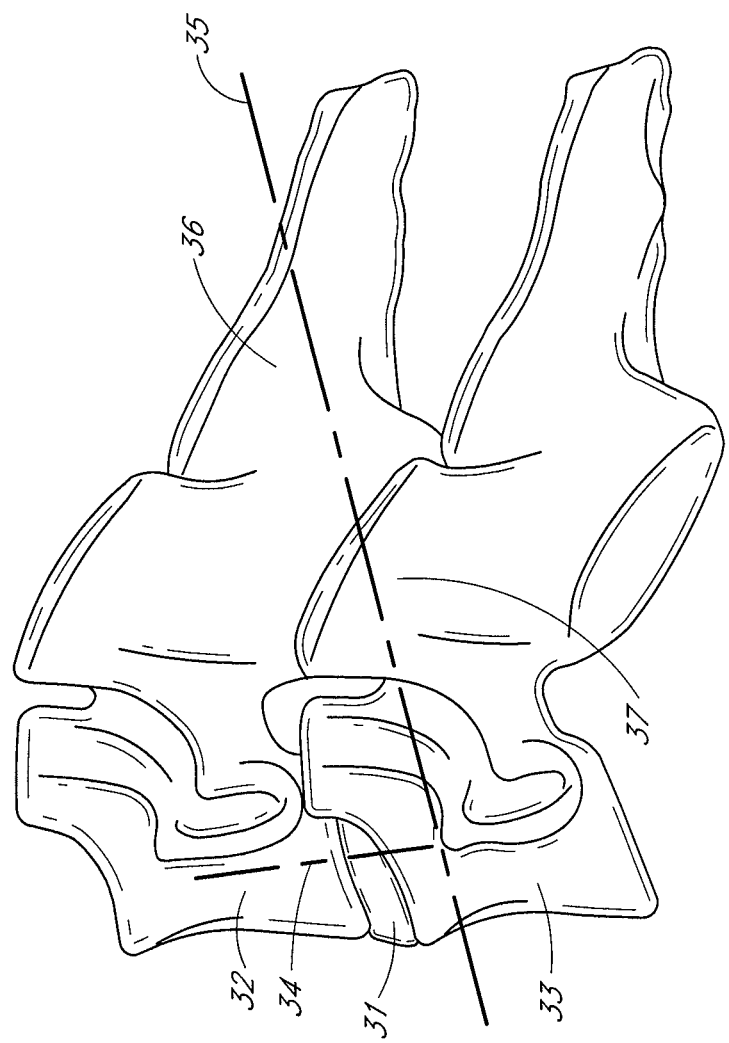
FIG. 3 shows a sagittal (side) view of the cervical spine.

FIG. 3 shows a sagittal view of the cervical spine. As shown, a single spinal level is composed of the disc targeted for treatment 31, the superior vertebral body 32, and the inferior vertebral body 33.

In the cervical spine, the torsional axis of rotation 34 of the disc 31 is shown. The torsional axis 34 is aligned with the long axis of the spine. Any plane generally perpendicular to the torsional axis of rotation is defined as being aligned with the disc space. One generally preferred plane 35 passes through the spinous process 36 of the superior vertebral body 32 and the lateral aspect 37 of the superior articular process of the inferior vertebral body 33.

It is recognized that due to anatomical and surgical variation, it is unlikely that all points of fixation will lie precisely within a plane perpendicular to the torsional axis 14 and 34 of the targeted disc 11 and 31. However, trigonometry shows that any plane within +/−17.5 degrees of perpendicularity with the torsional axis of rotation 14 and 34 will result in no more than 30% off axis contribution. Accordingly, preferred planes for fixing one or more implants are those within 17.5 degrees of perpendicularity.

Figure 4:
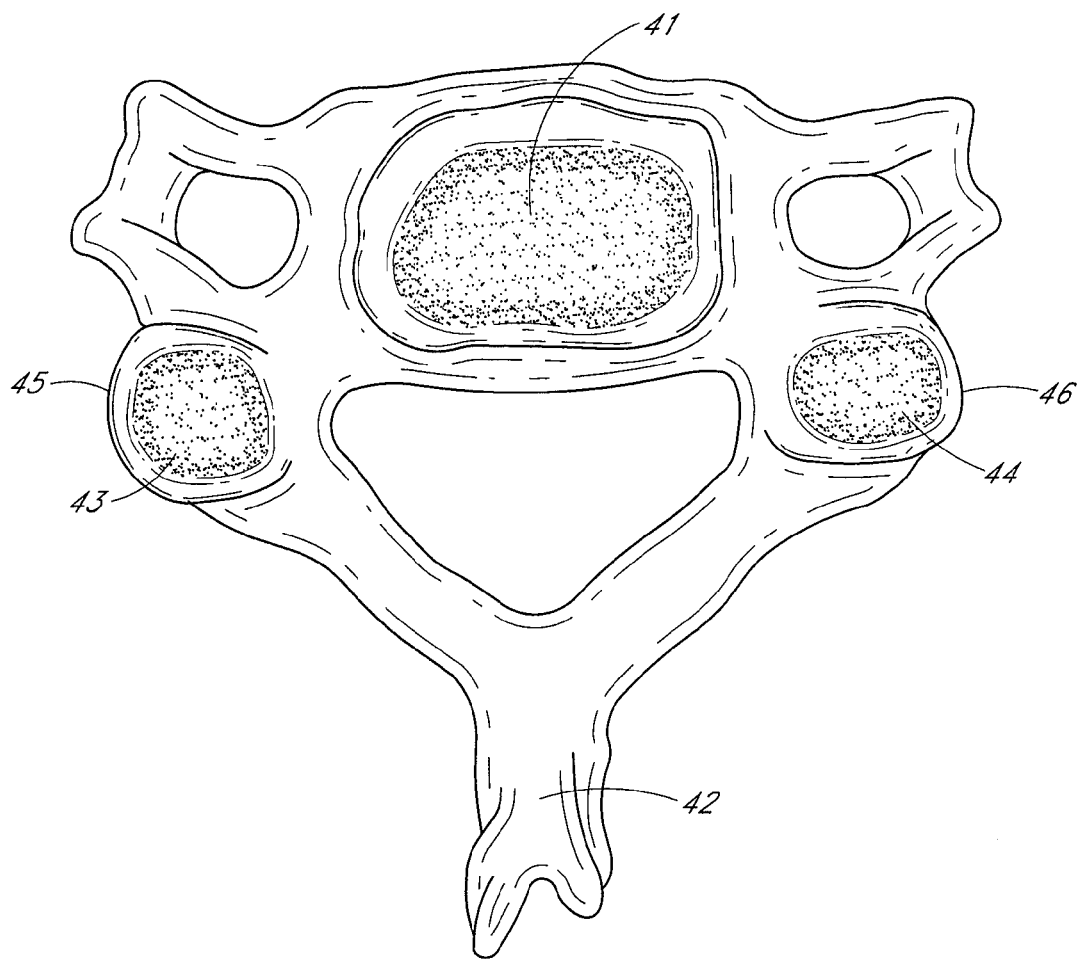
FIG. 4 shows a top view of a cervical vertebral body.

FIG. 4 shows a top view of a cervical vertebral body 41. In this view, it is possible to identify the spinous process 42, the superior articular processes 43 and 44, and the lateral aspects 45 and 46 of the superior articular processes 43 and 44.

Methods described permit the surgeon to install hardware at two, preferably three locations, generally aligned with the disc space, and to pass one or more implants between the locations to treat a single spinal level. Hardware may be installed on a first vertebral body, a second vertebral body or both in order to assist in fixation of an implant between vertebral bodies. A first vertebral body may be a superior vertebral body while a second vertebral body may be an inferior vertebral body, or vice versa.

In a preferred embodiment, hardware is fixed on a superior vertebral body at the spinous process and is the sole point of fixation on the superior vertebral body. Fixation on an inferior vertebral body may be bilateral, such as at two locations extending laterally outwardly on opposite sides of the spinous process. For example, in one embodiment, two implants may be fixed to the spinous process of a superior vertebral body and may extend laterally outward such that one implant is fixed to a first pedicle of an inferior vertebral body and the other implant is fixed to a second pedicle of the inferior vertebral body. In another embodiment, two implants fixed to the spinous process of a superior vertebral body may extend laterally outward such that one implant is fixed to a first mamillary process of an inferior vertebral body and the other implant is fixed to a second mamillary process of the inferior vertebral body. In some embodiments, fixation could be unilateral using a sufficiently stiff implant.

The location for fixation on the inferior vertebral body is dependent on the level of the spine being operated on. In the lumbar spine, the preferred location for fixation is in the region from the pedicle superiorly and medially onto the mamillary process, bilaterally. At the L5-S 1 spinal level, the preferred location for fixation is to the sacrum, generally aligned with the disc space. In the cervical spine, the preferred location for fixation to the inferior vertebral body is the lateral aspect of the superior articular process.

Various implants are provided which may provide torsional stabilization to the spine. These implants may be configured to extend in tension between a superior vertebral body and an inferior vertebral body in a plane generally aligned with the disc space to provide torsional stabilization. The implants may be fixed to one or more locations of the superior vertebral body and the inferior vertebral body. As used herein, the term "fix" means direct fixation of an implant to a vertebral body (such as by tying the implant around the vertebral body) or indirect fixation of an implant to a vertebral body by using fixing a fixation device such as a staple, anchor, endobutton or outrigger.

As illustrated below, the implants may be of various shapes and sizes. While some of the implants may be comprised of relatively stiff materials including metals such as titanium and stainless steel and non-metals such as carbon fiber, in a preferred embodiment, the implant is comprised of a material that allows for sufficient strength and flexibility. In some embodiments, the stabilizing implant is flexible and can be fashioned of a variety of biocompatible materials including polymeric surgical fabrics using resorbable and/or non-resorbable polymers in the form of weaves, braids, knits and embroidery. In some embodiments, the stabilizing implant comprises a solid polymer including resorbable and non-resorbable polymers, autograft soft tissue, allograft soft tissue, allograft or autograft bone, metal fabrics, metal meshes or solid metal components in addition to titanium and metal, as well as biocompatible composites. Having a flexible implant allows the implant to be used advantageously with a variety of hardware at specific locations of the spine. Having a flexible implant also allows for ease in fixing the implant using the preferred methods of the present application, which may allow the implant to be grabbed, pulled and placed in tension in between locations. A flexible implant also permits laying the implant over the posterior part of the facet so as to take a non-linear path between points of fixation. A flexible implant also allows for passing the implant from one location to another, as will be described later in this specification. As an implant may contact bone between its anchor points and will lie within muscle, it may also be advantageous to have the implant coated with a biocompatible hydrophilic material or with a biocompatible hydrogel so that friction may be reduced between the implant and the biological material that it contacts. Besides flexibility, an implant's stiffness may be considered when providing torsional stabilization using one or more implants. The stiffness of an implant can be varied by using different types of materials and/or by adjusting the geometry of the implant to provide a variety of stiffening effects.

Implants of various geometries are now provided. FIG. 5 shows one embodiment of an implant 51 having a generally rounded cross-section. FIG. 6 shows one embodiment of an implant 61 having a generally rectangular cross-section. FIG. 7A shows one embodiment of an implant 71 having a tubular cross-section.

In a preferred embodiment, the implants are comprised of a flexible, compliant material that allows the implant to be shaped with ease in and around spinal segments. FIG. 7B shows the effect of using the compliant tube implant 71 of FIG. 7A when passing the implant around a piece of bone 72. As shown, the cross section at both ends 73 and 74 are generally tubular while in the central portion 75 of the implant 71, the thickness of the implant is reduced. This reduction in thickness corresponds to a collapse of the tube in this region which may be beneficial in applications where the implant comes in contact with the bone. Allowing the implant 71 to be flexible and work around the bone 72 reduces wear and tear to the bone. In addition, in some embodiments, deformation of the implant 71 at its central portion 75 can result in increased strength of the implant by deformation strengthening at the central region of the implant.

FIG. 8 shows a filled tubular implant 81 according to one embodiment. In this embodiment, the implant is again tubular in cross section 82, but the tube is also filled with material 83. Filler material 83 can act as a cushion for various loads on the implant. Examples of filler material in the tubular implant 81 include elastic materials such as rubber, viscoelastic materials and advanced polymers, metal monofilament, animal derived materials (allograft, autograft) and combinations of the above. The benefits of this structure are that the inner material 83 may be used as the load carrying element, while the tube 82 is designed to better integrate with the adjacent material. For example, the inner material could be a polymer or metal monofilament and the external tube could be highly porous. The monofilament provides the strength to torsionally stabilize the spinal level, whereas the highly porous external tube permits integration of the implant with adjacent soft tissue.

The stabilizing implant may be fixed to the bone using a variety of available means, including screws, staples, anchors (including soft tissue anchors) and other types of hardware. The hardware can be fashioned of a variety of biocompatible materials, including resorbable and non-resorbable polymers, metals, as well as assemblies of polymers and metals. Besides or in addition to using hardware, an implant may be fixed to bone using a surgical adhesive.

FIG. 9A shows a staple 91 which can be used as an anchor in the present application. FIG. 9B shows an anchor 91 assembled to an implant 92. The implant 92 corresponds to the implant 61 of FIG. 6 having a generally rectangular cross-sectional area. Methods and means of assembling an implant to an anchor are described later.

FIG. 10 shows an embodiment of an anchor 101 comprised of a threaded bone anchoring portion 102 and an implant receiving portion 103. The hole 104 in the implant receiving portion 103 can be configured to match, but be a slightly oversized version of the cross section of the implant.

FIG. 11 shows an exploded view of an embodiment of an anchor comprised of a bone anchoring component 112 and an implant attachment post 113. The bone anchoring component is threaded externally to attach to the bone, and the thread could be self-tapping to minimize the number of instruments required to insert the device. The bone anchoring component 112 also features an internal threaded hole 114 to receive the threaded portion 115 of the implant attachment post 113. The implant attachment post 113 also has a cap 116 which can have a feature (not shown) to permit tightening of the implant attachment post 113 to the bone anchoring component 112.

FIG. 12A shows a front view of an offset anchor 121. The anchor has two holes 122, 123. The first hole 122 is intended to receive a screw (not shown) that can be used to fix the anchor to the bone. The second hole 123 is intended to receive an implant.

FIG. 12B shows a side view of the offset anchor 121 shown in FIG. 12A. As seen in the side view, the anchor permits attachment at one location (using hole 122) while fixing the implant at a second location by using hole 123. Fixation of the implant at hole 123 could be accomplished by a variety of means and methods, which will be described later. Using an offset anchor, such as shown in FIGS. 12A and 12B, advantageously allows for fixation of the implant at a suitable bone site, such as the pedicle, while still permitting the implant to be generally aligned with the disc space. Using an offset anchor advantageously permits fixation of implants to locations further away from the disc space, such as to sites which may have greater volumes of bone or locations that are easier to access.

Figure 13:
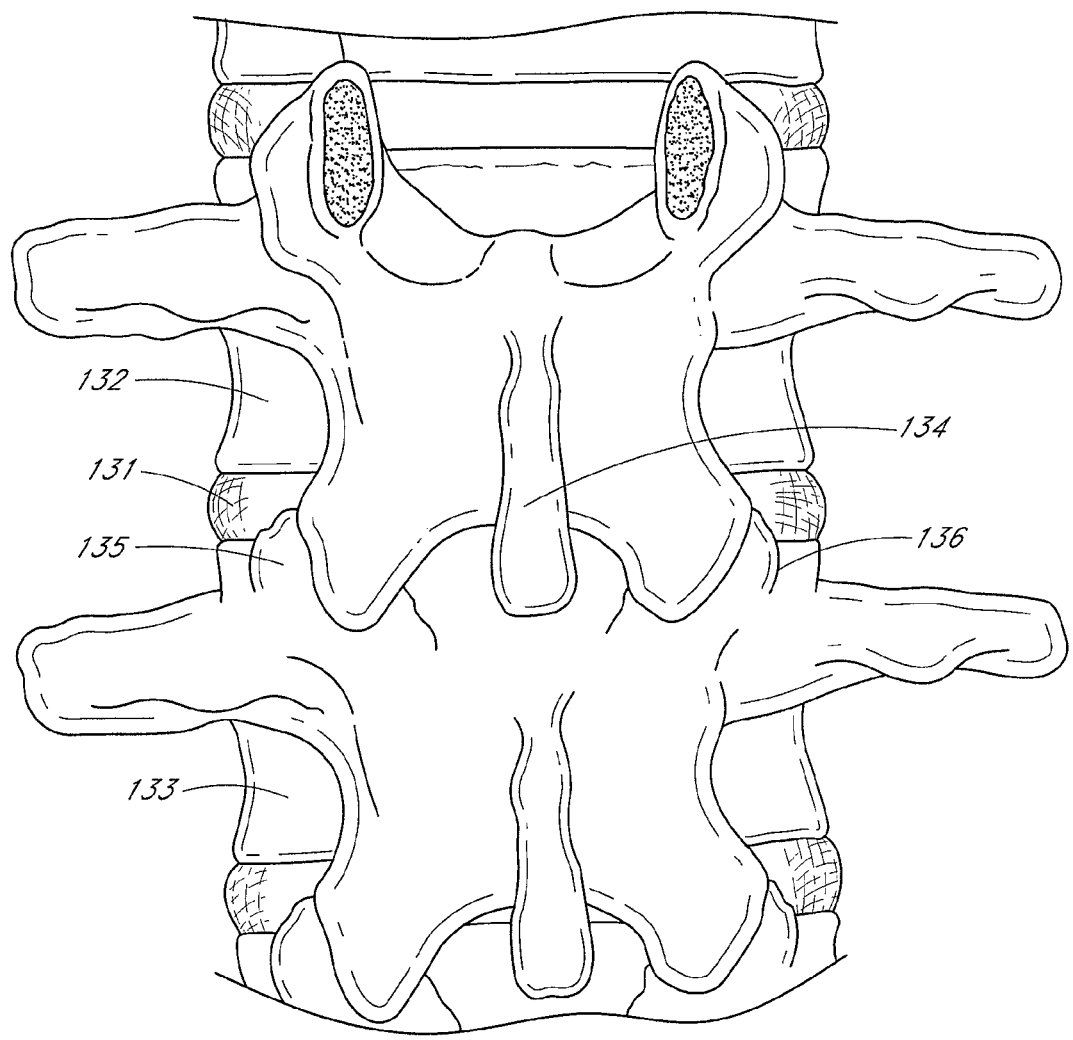
FIG. 13 shows a posterior (rear) view of a lumbar vertebral spine.

FIG. 13 shows a posterior (rear) view of a lumbar vertebral spine. As shown, a single spinal level is composed of the disc targeted for treatment 131, a superior vertebral body 132, and an inferior vertebral body 133. In this view, it is possible to visualize the spinous process 134 of the superior vertebral body 132, as well as the mamillary processes 135 and 136 of the inferior vertebral body 133.

Figure 14A:
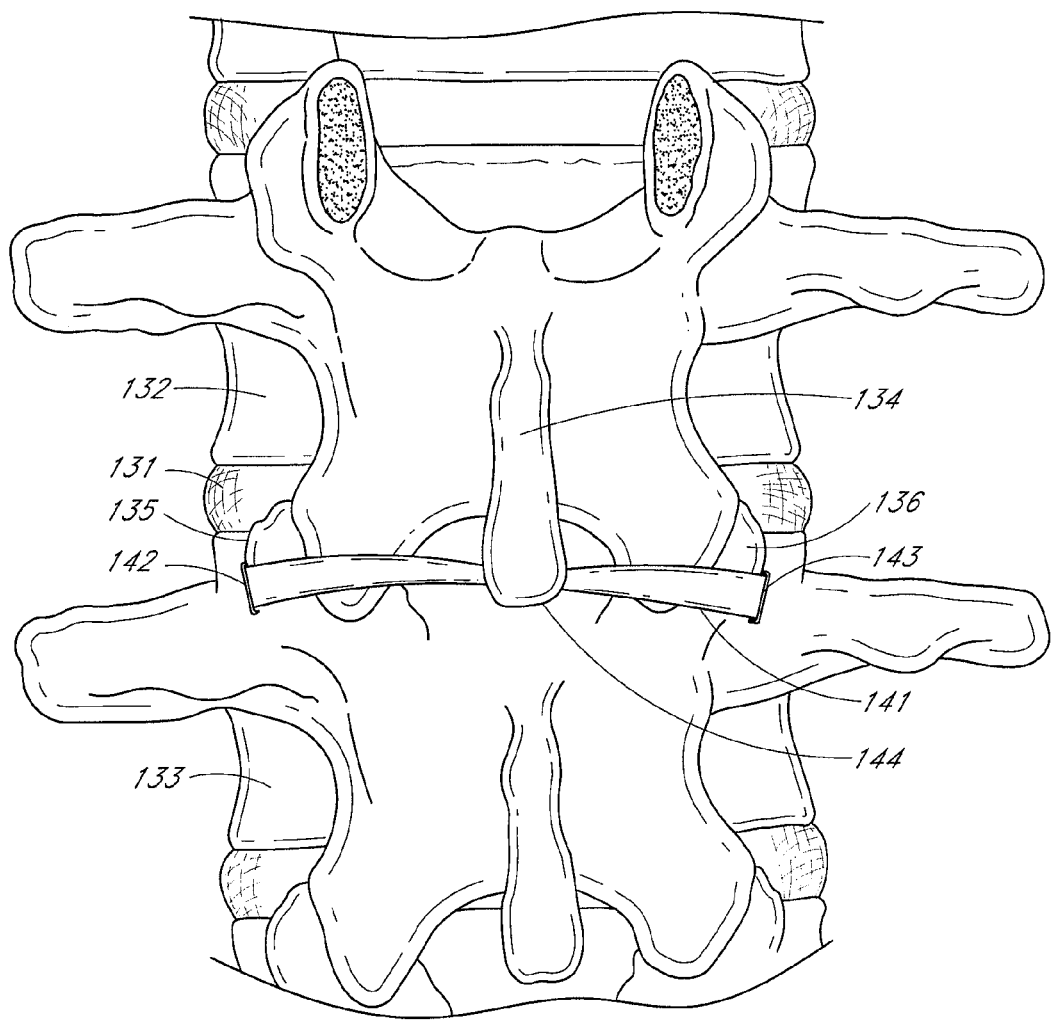
FIG. 14A shows a posterior (rear) view of a lumbar vertebral spine with an implant and anchors, where the implant is attached to the superior vertebral body via a loop according to one embodiment.

FIG. 14A shows a posterior (rear) view of a lumbar vertebral spine with an implant and anchors applied. The implant 141 is affixed at the mamillary process of the left side 135 of the inferior vertebral body 133 by a staple 142. It passes below the spinous process 134 of the superior vertebral body 132, wraps up along the right side of the spinous process, through a hole drilled in the spinous process, back down along the left side of the spinous process and then loops 144 under the spinous process. It then continues to the mamillary process of the right side 136 of the inferior vertebral body 133 where it is affixed to the bone using a staple 143.

Figure 14B:
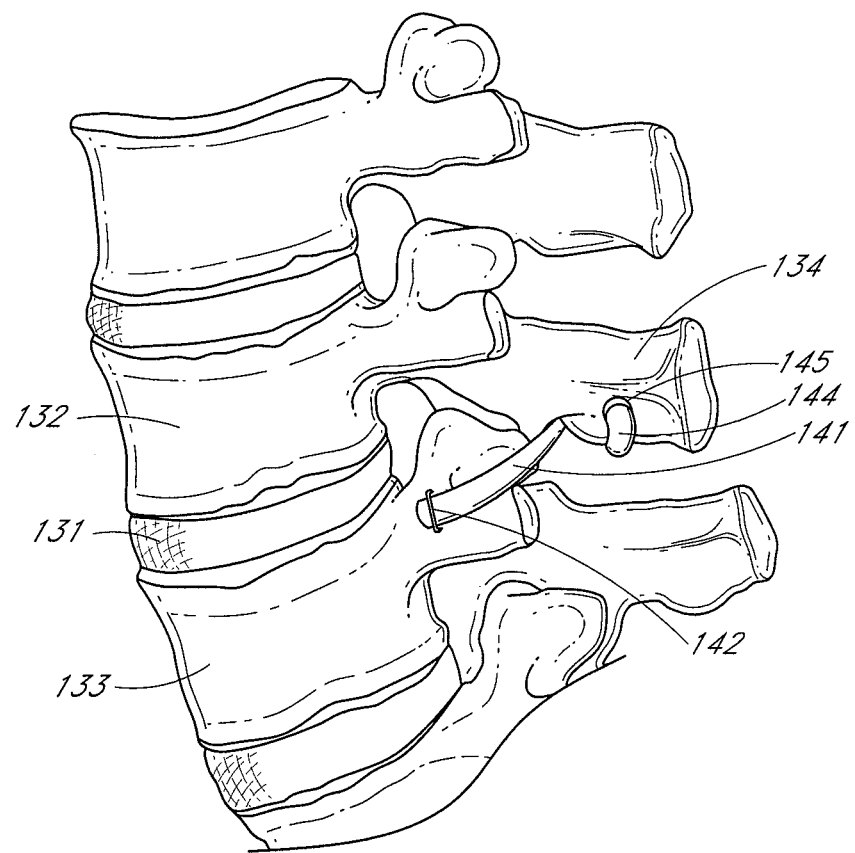
FIG. 14B shows a sagittal (side) view of the system of anchors and implant of FIG. 14A.

FIG. 14B shows a sagittal (side) view of the implantation system shown in FIG. 14A. As in FIG. 14A, the implant 141 is affixed at the mamillary process of the left side of the inferior vertebral body 133 by a staple 142. The implant 141 wraps under the spinous process 134 of the superior vertebral body 132, loops through a hole 145 in the spinous process, and then passes below 144 the spinous process and continues to the right side (not shown).

As an alternative to passing the implant through a hole in the spinous process and as a way to reduce bone trauma, the implant could loop over the entire spinous process instead of passing through a hole in the spinous process. While this approach would require less bone trauma, it may result in a less stable implant (as it is not as rigidly anchored to the spinous process of the superior vertebral body and may be subject to loosening by sliding anteriorly along the spinous process), and may require more soft tissue stripping of the muscles that attach to the spinous process.

Fixation to locations on the inferior vertebral body, such as at the mamillary processes or the pedicles, can be accomplished by using a variety of hardware, including the staple shown in FIG. 9A and the bone anchors shown in FIGS. 10 and 11. Additionally, there are a variety of metal and polymeric screws, some made of either resorbable and/or non-resorbable polymers, that can be used to anchor an implant to the inferior vertebral body. In some embodiments, the anchor comprises a suture anchor capable of being fixed into the inferior vertebral body. Additionally, other mechanical means of fixation include screws and nails to fix the implant to the inferior vertebral body. In these cases, the mechanical means would pass through the implant and into the selected boney location.

Alternatively, a surgical adhesive could be used to fix the implant directly to the bone and eliminate some or all hardware. In this case, the implant would be put in proximity to the desired bone location, the adhesive applied to either the implant or the bone location and the implant held against the bone until the adhesive set, using whatever technique the adhesive producer suggests for setting the adhesive.

Various hardware, besides those used as fixation devices to an inferior vertebral body, may also be used with the spinous process of the superior vertebral body. Hardware, including alternate anchors, may be used to fix the implant to the spinous process. When using hardware to fix the implant to the spinous process, it may be easier to have two or more separate implants. In one embodiment, a first implant can extend from the left side fixation on the inferior vertebral body to the spinous process of the superior vertebral body, while a second implant can extend between the right side fixation on the inferior vertebral body and the spinous process of the superior vertebral body. The implants used in such a configuration can include any of those implants described in FIGS. 5, 6, 7A and 8 and any combination thereof. These implants can be chosen or made to have an appropriate length to span the distance on one side from an inferior vertebrae to a superior vertebrae. Other suitable implants, may include for example, one or more sutures or wires.

Various hardware are now described which may be used to fix one or more implants to the superior vertebrae, and more specifically, the spinous process of the superior vertebrae. In some embodiments, the hardware used for fixation to the spinous process may also be used to fix one or more implants to the inferior vertebral body. The hardware can be attached to the spinous process of the superior vertebrae by engaging the spinous process and/or by engaging a hole through the spinous process. Using hardware described below (which includes but is not limited to turnbuckles and outriggers) advantageously provides a stable mechanism for securing the implants at or near the spinous process. In addition, using hardware of different geometries provides the additional benefit of allowing for attachment of one or more implants either at the spinous process or near the spinous process (e.g., below or along the side of the spinous process), thus providing the flexibility for fixing an implant at various locations to optimize torsional stability from subject to subject. The use of hardware also permits distributing force applied to the spinous process over a sufficiently large area so as to avoid local failure of the cancellous bone that constitutes the spinous process. Also, hardware can be manufactured out of a resorbable material so that the device has a temporary function—providing torsional stability until the resorbable material decays to the point where the mechanical function of the device is lost.

Figure 15B:
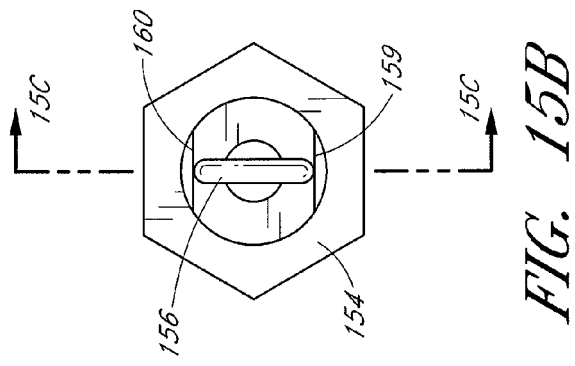
FIG. 15B shows a right side view of the turnbuckle of FIG. 15A.
Figure 15A:
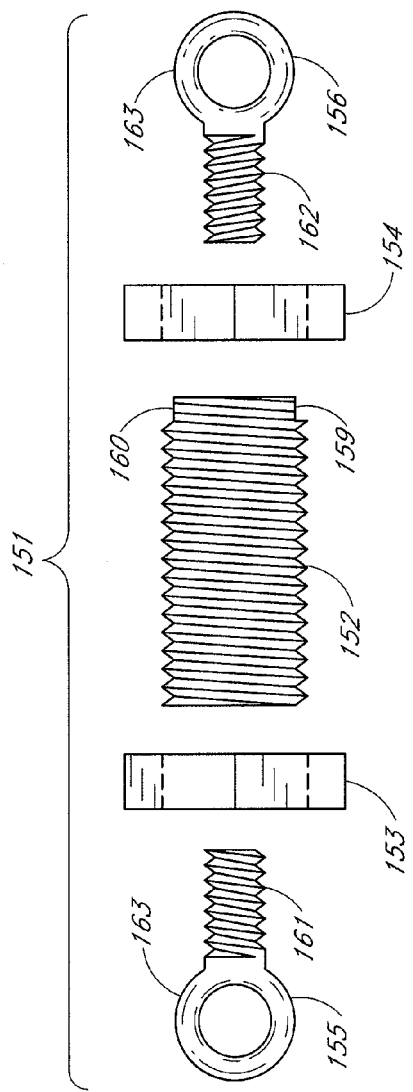
FIG. 15A shows an exploded front view of a turnbuckle.
Figure 15C:
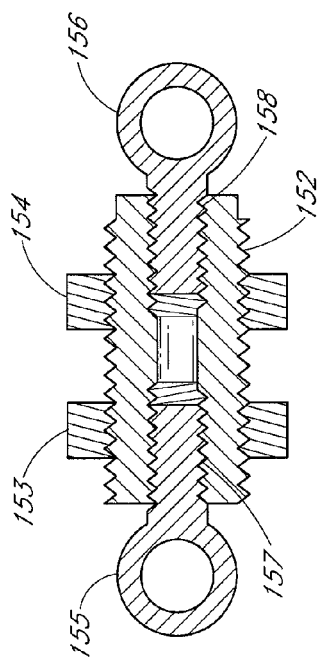
FIG. 15C shows an assembled bottom section view of the turnbuckle of FIG. 15A.

FIGS. 15A, 15B and 15C show a front exploded, right side and an assembled bottom section view respectively of a turnbuckle 151. It is composed of a body 152, two nuts 153 and 154, and two outriggers 155 and 156. The nuts permit clamping of the body to the spinous process. The outriggers permit fixation of the implant to the turnbuckle.

The body 152 has an external thread on the outside that mates with the internal thread on the nuts 153 and 154. The body also has two internal threads 157 and 158 (shown in FIG. 15C) that receive the outriggers 155 and 156. The internal thread 157 is cut in the opposite direction as the internal thread 158 (making one a "right handed" thread and the other a "left handed" thread). Two flats 159 and 160 are cut on the outside of the body 152.

The outriggers 155 and 156 each have external threaded shafts 161 and 162 respectively. Consistent with the body, the threaded shaft 161 is cut in the opposite direction as the external thread on the shaft 162. The threaded shaft 161 is cut in the same direction as the internal thread 157 of the body; the threaded shaft 162 is likewise cut in the same direction as the internal thread 158 of the body. The end of the outriggers 163 is configured to receive an end of the implant and to permit fixation of the implant to the end of the outrigger.

Figure 16:
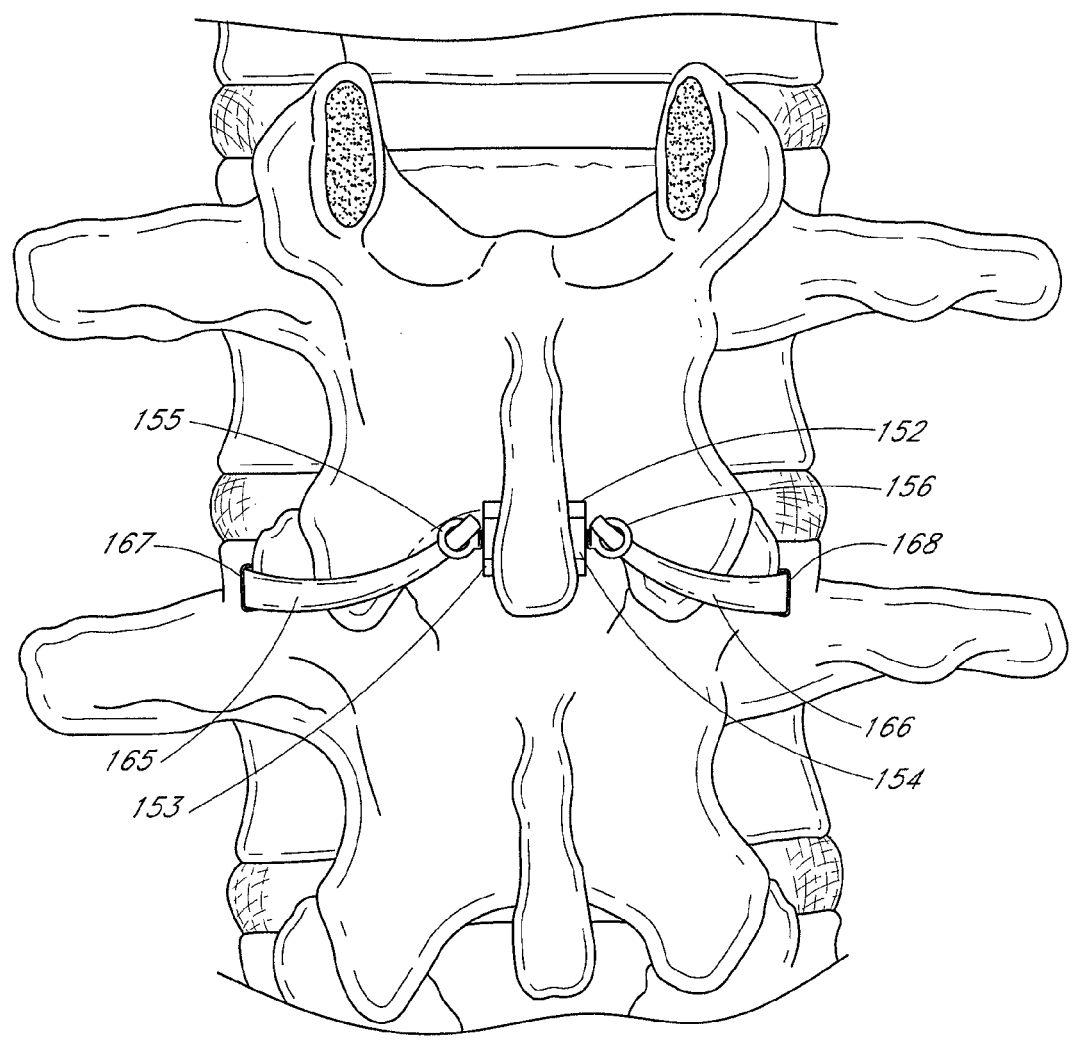
FIG. 16 shows a posterior (rear) view of a lumbar vertebral spine with two implants, two anchors applied, wherein the implants are attached to the spinous process via a turnbuckle according to one embodiment.

FIG. 16 shows a posterior (rear) view of a lumbar vertebral spine with two implants 165 and 166, two anchors 167 and 168 applied to fix the implants to the inferior vertebral body, and a turnbuckle 151 having outriggers 155 and 156 to attach the implants to the spinous process. Fixation of the implants 165 and 166 to the outriggers 155 and 156 could be by a variety of means described below. No fixation of the implants to the outrigger is shown. Once the implants are fixed bilaterally via the anchors to the inferior vertebral body and the implants fixed to the outriggers (but prior to tightening down on the nuts 153 and 154 to clamp the turnbuckle to the spinous process), the two implants can be simultaneously tightened. This is accomplished by aligning a wrench with the flats 159 and 160 (shown in FIGS. 15A and 15B) on the body and rotating. Rotation in one direction will result in simultaneous tightening; rotation in the opposite direction will result in loosening. After reaching the appropriate tightness, the turnbuckle can then be clamped to the spinous process by tightening both nuts 153 and 154.

While there are some circumstances where due to anatomy and surgeon preference, it is possible to fix through the spinous process, there are other times when it is preferable to fix the implants to a location below the spinous process. One possible time is when fixation to the inferior vertebral body is at the level of the pedicle, as shown in FIG. 1 and it is desired that the implants are generally aligned with the alternative plane 18 of FIG. 1. Using various hardware as described in this application to engage the spinous process can help to facilitate placement of an implant to a desired location below the spinous process.

Figure 17A:
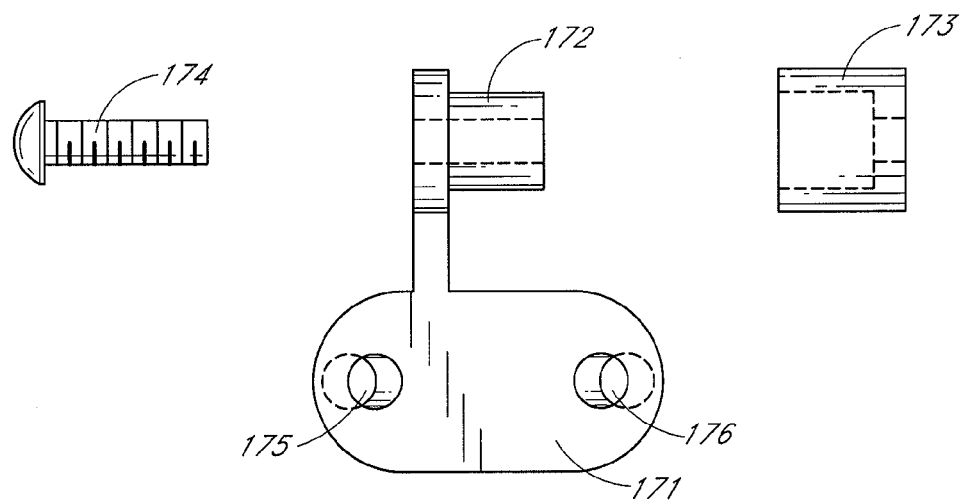
FIG. 17A shows a front exploded view of an alternative embodiment of an outrigger.
Figure 17B:
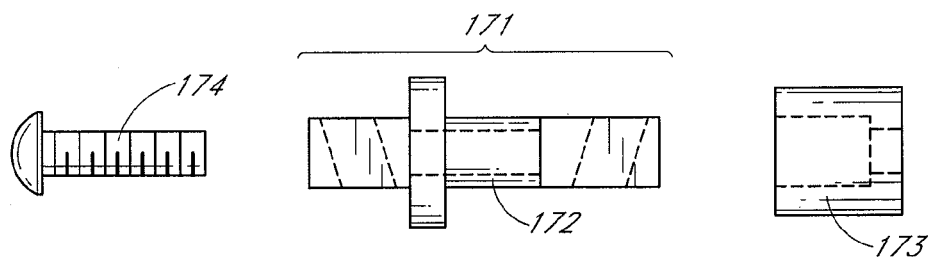
FIG. 17B shows a top exploded view of the outrigger of FIG. 17A.

FIGS. 17A and 17B show exploded views of an alternative embodiment of an outrigger 171 for fixing two implants to a location below the spinous process of the superior vertebral body. The outrigger 171 has a stem portion 172 that mechanically couples the outrigger to a nut 173. As shown, the stem portion 172 of outrigger 171 fits within the nut 173. The stem portion 172 and nut 173 can be held together via a screw 174 that passes through the stem portion 172 and threads into the nut 173. The outrigger also has two holes 175 and 176 respectively that can receive one or more implants. It should be noted that it is preferable to have the holes 175 and 176 angled with respect to the outrigger 171 so as to put the holes in alignment with the overall direction of the implant from its fixation point on the inferior vertebral body or in alignment with an intermediate location between fixation point and the outrigger where the implant, when tensioned, can follow a linear path to the outrigger 171.

Figure 17C:
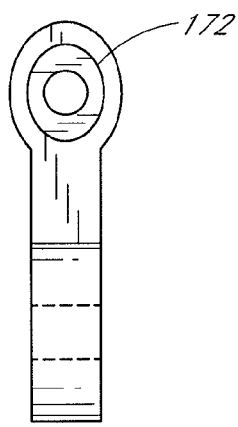
FIG. 17C shows a side view of the outrigger of FIG. 17A.

FIG. 17C shows an additional side view of the outrigger 171 of FIG. 17A. As best seen in FIG. 17C, the stem portion 172 of outrigger 171 is oval. The advantage of this shape is that it couples the outrigger 171 with the nut 173 when attempting to twist about the long axis of the stem portion 172. In turn, it is preferable that the outrigger stem 172 of the outrigger 171 be put through a hole in the spinous process that matches the shape of the stem portion 172, thus transferring any twist induced by the implants directly to the bone of the spinous process and limiting any rotations due to twist.

Figure 18A:
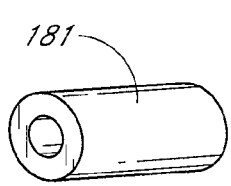
FIG. 18A shows a clamp used to fix an implant according to one embodiment.

When using hardware to fix an implant to a vertebral body, it may be preferable to clamp the implant to the hardware instead of using one or more knots to fix the implant to the hardware. FIG. 18A shows a clamp 181 that can be used to fix the implant. The clamp 181 is shown in use with an implant 185 in FIG. 18B.

Figure 19:
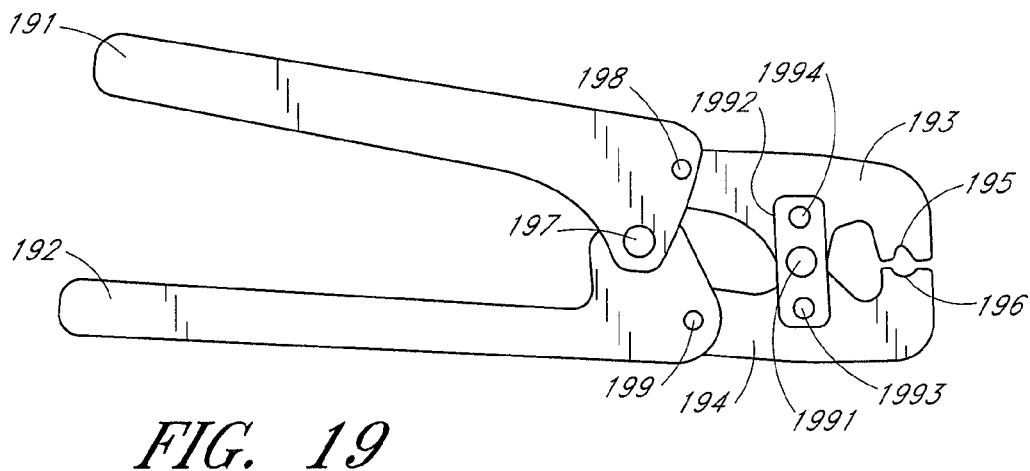
FIG. 19 shows a view of a crimping instrument used to fix the clamp to an implant according to one embodiment.

FIG. 19 shows a crimping instrument suitable for fixing the clamp to the implant. The instrument has two handles 191 and 192, two jaws 193 and 194 and portions of a cavity 195 and 196 created in the jaws. A band 1992 is pinned 1993 and 1994 onto the jaws 193 and 194 to hold the pin 1991 in place. Hinge pins 197, 198, 199 and 1991 and their relative positions permit a multiplication of the force generated at the handles to be applied to a clamp placed in the portions of the cavity 195 and 196.

Figure 18B:
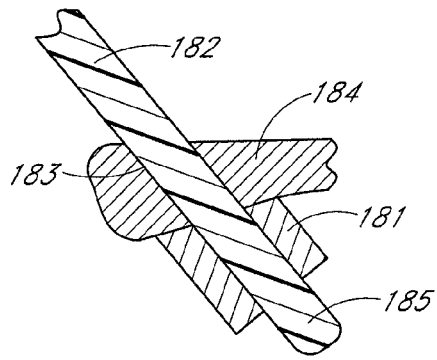
FIG. 18B shows a section view of an assembly of an implant, hardware and clamp according to one embodiment.

The use of the clamp 181 is shown in FIG. 18B. The implant 182 is passed through a hole 183 in the hardware 184 and then passed through the clamp 181. Once assembled, one end of the implant 185 would be held taught using a hemostat or similar device. A crimping instrument, similar to that shown in FIG. 19, would then be used to hold the clamp 181 tight to the hardware 184. The crimping instrument would then be actuated to plastically deform the clamp 181 around the implant 182, thus preventing the implant from pulling through the clamp and fixing the implant to the outrigger.

Figure 20A:
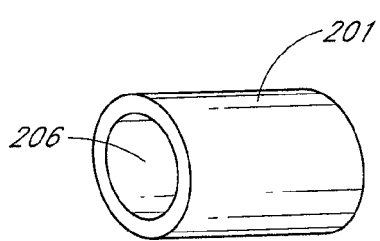
FIG. 20A shows an alternative clamp that can be used to fix an implant.
Figure 20B:
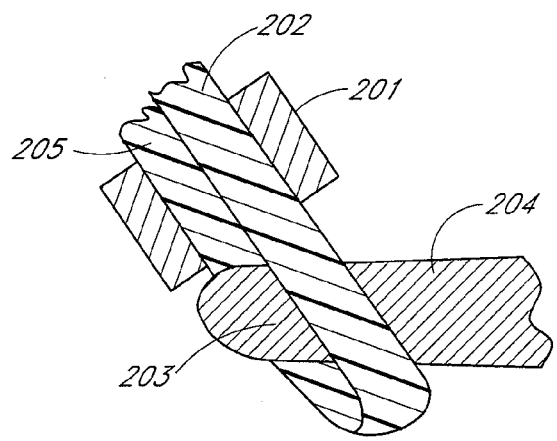
FIG. 20B shows a section view of an assembly of an implant, hardware and an alternative clamp according to one embodiment.

FIG. 20A shows an alternative clamp 201 that can be used to fix the implant. The cavity 206 is sized to fit two implants. As shown in FIG. 20B, an implant 202 is passed through the clamp 201, through a hole 203 in the hardware 204, wrapped around the hardware 204 and back through the clamp 201 such that the free end of the implant 205 is turned back onto the previously fixed end of the implant 202. Once assembled, one end of the implant 205 would be held taught using a hemostat or similar device. A crimping instrument, similar to that shown in FIG. 19, may then be used to crimp the clamp 201 to both parts of the implant 202 and 205. The advantage of this approach is that the clamp 201 does not need to contact the hardware 204, eliminating one possible wear couple. The disadvantage to this approach is that the clamping is done deep to the hardware, if the hardware is an outrigger or such as described in FIG. 17A.

To ease fixation of an implant to hardware, it may be preferable to have a split clamp 271 as shown in FIG. 27. In this configuration, the clamp 271 features a split 272 along its length. The split 272 permits insertion of an implant from the side of the clamp 271. Following insertion, the clamp is crimped by a tool such as that described previously.

Generally, fixation of an implant to hardware can be accomplished by a variety of means, which are dependent on the type of hardware employed. For hardware such as nails, screws and staples including those described in FIGS. 9A and 11, the hardware could pass through the implant and then into the bone where the implant is to be fixed. For hardware that has a member around which the implant can pass, such as those described in FIGS. 9A, 10, 12A-12B, 15A-15C, 17A-C, 23A-B, 24A-B, 25A-25B and 26A-B, the implant could be tied to the member, hitched to the member, knotted after passing through a hole in the member or crimped to the member. Additionally, an implant can be fixed to hardware having a member around which the implant can pass by passing the implant around the member, doubling the implant on itself (as shown in FIG. 20B), and then using a variety of mechanical means to fix the implant to itself. These include sutures, staples and rivets, as well as clamps such as those shown in FIG. 18A, FIG. 20A and FIG. 27. If the implant were suitably porous, for example a fabric, or chemically appropriate to develop a chemical bond between the implant and the adhesive, an alternative means of fixation is the use of a surgical adhesive, such as cyanoacrylate or fibrin glue to fix the implant to the hardware. The implant would be wrapped around or through the hardware and the adhesive used to hold the implant to itself.

A surgical adhesive could also be used to fix the implant directly to the bone and eliminate some or all hardware. In this case, the implant would be put in proximity to the desired bone location, the adhesive applied to either the implant or the bone location and the implant held against the bone until the adhesive set, using whatever technique the adhesive producer suggests for setting the adhesive.

Figure 21:
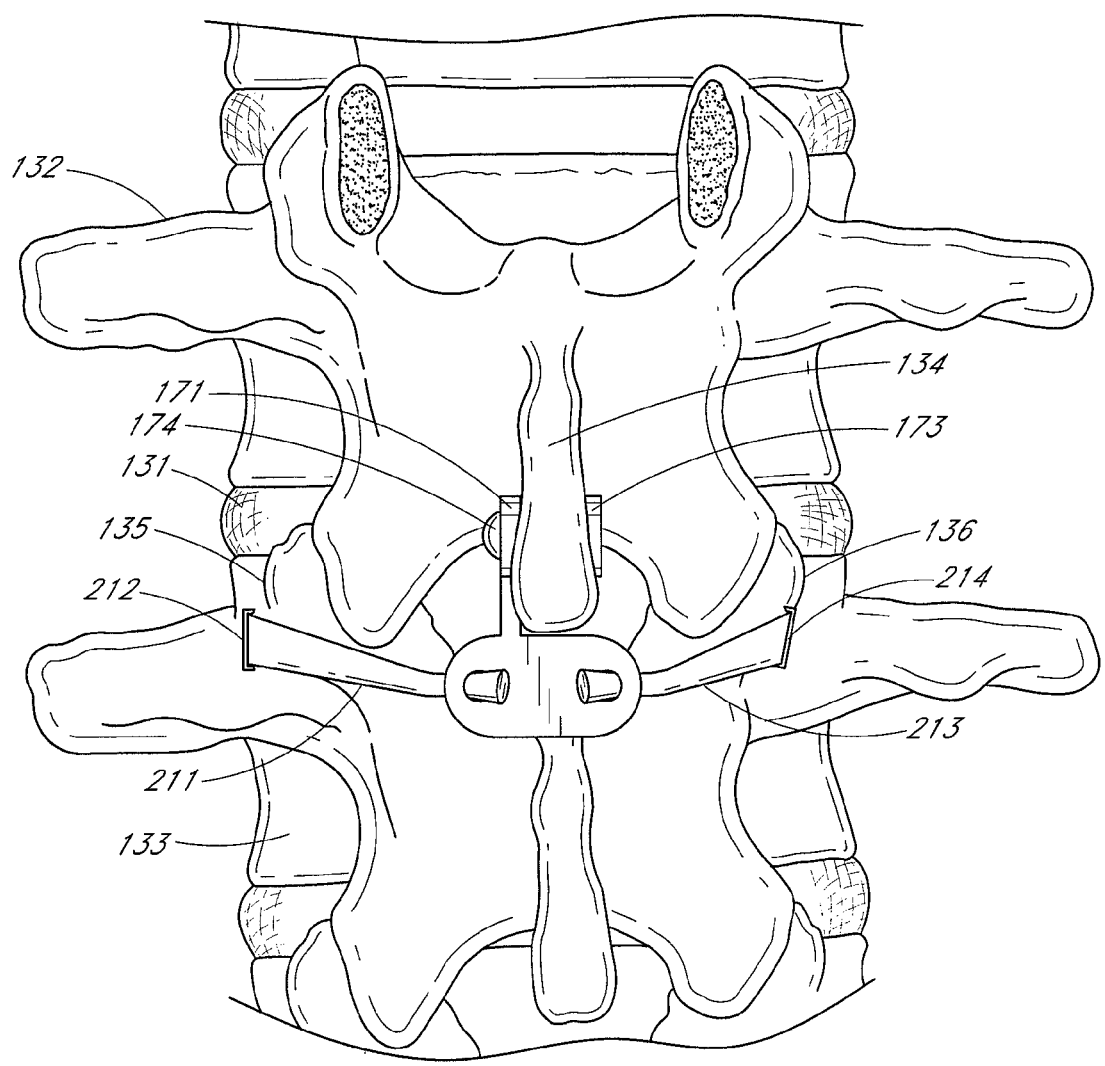
FIG. 21 shows a posterior (rear) view of a lumbar vertebral spine having two implants attached to the spinous process via an outrigger according to one embodiment.

FIG. 21 shows a posterior (rear) view of a lumbar vertebral spine as previously described in FIG. 13, having two implants 211, 213 attached to locations of an inferior vertebrae 133 using two anchors 212, 214. The implants are also attached to the spinous process 134 via an outrigger 171. As shown, a single spinal level is composed of the disc targeted for treatment 131, the superior vertebral body 132, and the inferior vertebral body 133. In this view, it is possible to visualize the spinous process 134 of the superior vertebral body 132, as well as the mamillary processes 135 and 136 of the inferior vertebral body 133.

An implant 211 is affixed at the mamillary process of the left side 135 of the inferior vertebral body 133 by an anchor 212. The implant 211 passes towards the midline, where it is affixed to an outrigger 171. Fixation of the implant 211 to the outrigger 171 could be by a variety of means previously described. No fixation of the implant to the outrigger is shown. A second implant 213 is affixed at the mamillary process of the right side 136 by an anchor 214. It is attached to the spinous process 134 of the superior vertebral body 132 via the outrigger 171. Fixation of the implant 213 to the outrigger 171 could be by a variety of means previously described. No fixation of the implant to the outrigger is shown. The outrigger 171 is clamped together to the spinous process via a nut 173 and screw 174.

Figure 22:
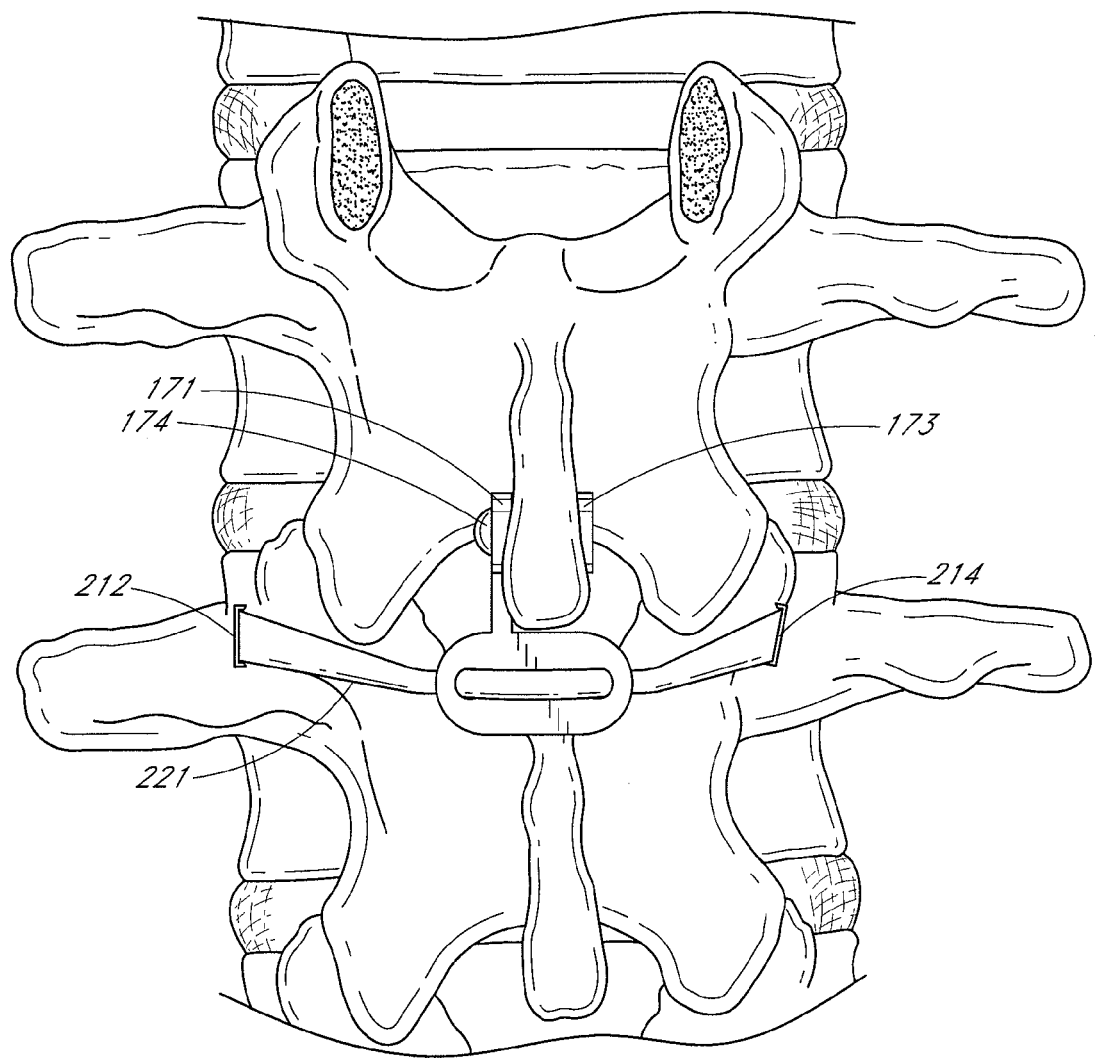
FIG. 22 shows a posterior (rear) view of a lumbar vertebral spine with one implant attached to the spinous process via an outrigger according to one embodiment.

FIG. 22 shows an alternative assembly using the outrigger 171 of FIG. 21 with a single implant 221. In this assembly, the hardware used is the same (anchors 212 and 214, outrigger 171 and nut 173 clamped together to the spinous process via a screw 174). A single implant 221 is used that is fixed to the anchors 212 and 214 on the inferior vertebral body and which passes through both holes in the outrigger 171. Fine tensioning of this assembly could be accomplished by sliding shims between the implant and the outriggers, with different thickness shims resulting in different amounts of tensioning.

Figure 23A:
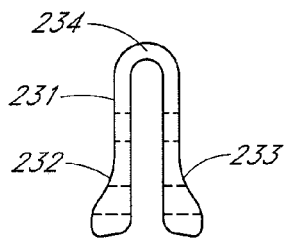
FIG. 23A shows a front view of an outrigger.
Figure 23B:
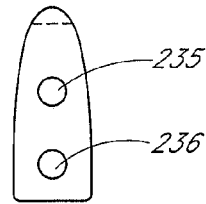
FIG. 23B shows a side view of the outrigger in FIG. 23A.

A variety of alternative outriggers are also possible. FIG. 23A and FIG. 23B show views of one such outrigger 231. The outrigger 231 has two arms 232 and 233 connected by a reduced section hinge 234 that permits deformation of the outrigger. The hole 236 as shown in FIG. 23B represents a hole through which an implant could pass and thus be secured to the outrigger. A hole for this purpose would be in each arm 232 and 233. The orientation of the hole 236 could be in a variety of directions so as to put the hole in alignment with the overall direction of the implant from its fixation point on the inferior vertebral body or in alignment with an intermediate location between fixation point and the outrigger where the implant, when tensioned, can follow a linear path to the outrigger. Additionally, there is a secondary fixation hole 235 that could receive a screw (not shown) in both arms 232 and 233.

The outrigger of FIG. 23A could be assembled to the spinous process using the following procedure. A hole of appropriate shape is cut or punched through the spinous process. One arm of the outrigger (either 232 or 233) is passed through the hole so that the arms are separated by the spinous process, and the reduced section hinge lies generally within the hole created in the spinous process. A screw could then be drilled through the hole 235 in outrigger arm 233, through the spinous process and then through a preexisting hole in outrigger arm 232.

A second method for assembling the outrigger of FIG. 23A to a spinous process is as follows. A small hole is created in the interspinous ligament at the superior surface of the spinous process. One arm of the outrigger (either 232 or 233) is passed through the hole so that the arms are separated by the spinous process, and the reduced section hinge lies generally between the targeted spinous process and the adjacent spinous process. A screw could then be drilled through the hole 235 in outrigger arm 233, through the spinous process and then through the preexisting hole in outrigger arm 232. This method could be advantageous for small spinous processes, such as those seen in the cervical spine. In the cervical spine, it may not be desirable that the outrigger arms 232 and 233 extend below the spinous process.

Fixation of one or more implants could be done using the means and methods already described for attaching implants to hardware.

Figure 24A:
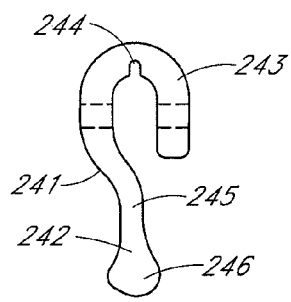
FIG. 24A shows a front view of an alternative outrigger.
Figure 24B:
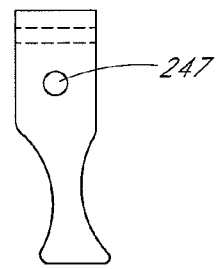
FIG. 24B shows a side view of the alternative outrigger in FIG. 24B.

As an alternative to having to pass one or more implants through holes in an outrigger as described above, it is also possible to have a post outrigger 241, as shown in FIG. 24A and FIG. 24B. In one possible configuration, the arms are not symmetric, with arm 242 extending longer than arm 243. The arms 242 and 243 are connected through a reduced section hinge 244. Fixation of one or more implants to the outrigger 241 is intended to occur along the reduced section length 245. The increased section 246 lies below the reduced section as a stop or limit to prevent the one or more implants from sliding off of the outrigger 241. Both arms 242 and 243 have an aligned hole 247 that could receive a screw (not shown) to fix the outrigger 241 to the spinous process.

The outrigger of FIGS. 24A and 24B could be assembled to the spinous process using the following procedure. A hole of appropriate shape is cut or punched through the spinous process. The short arm of the outrigger 243 is passed through the hole so that the arms are separated by the spinous process, and the reduced section hinge lies generally within the hole created in the spinous process. A screw could then be drilled through the hole 247 in outrigger arm 243, through the spinous process and then through the preexisting hole in outrigger arm 242.

Fixation of one or more implants to the outrigger 241 could be done using the means and methods already described for attaching implants to hardware.

Figure 25A:
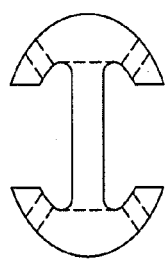
FIG. 25A shows a front view of an alternative spinous process anchor according to one embodiment.
Figure 25B:
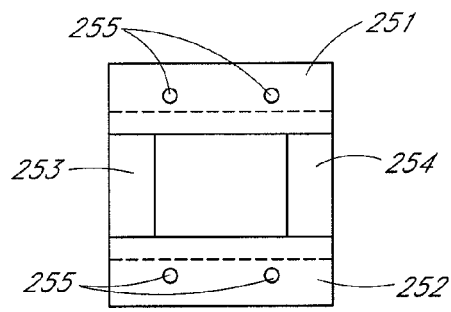
FIG. 25B shows a side view of the alternative spinous process anchor of FIG. 25A

An alternative spinous process anchor is also embodied that permits a similar means of fixation of the implant but without the outrigger. FIGS. 25A and 25B show front and side views respectively of such an anchor. It is composed of top 251 and bottom roofs 252 which are connected by spaced apart uprights 253 and 254. The top and bottom roofs 251 and 252 preferably have a multitude of holes 255 or features to permit bone and soft tissue ingrowth into the anchor. The overall shape of the roofs 251 and 252 are intended to snugly fit within a hole created in the spinous process.

The anchor of FIGS. 25A and 25B could be assembled to the spinous process using the following procedure. A hole of appropriate shape is cut or punched through the spinous process. The anchor would then be pressed into the created hole. Implants would then be fixed to the anchor by means of the spaced apart uprights 253 and 254. Preferably, the distance from the outside surface of uprights 253 and 254 is on the order of the thickness of the spinous process so that the implants are located in close proximity to the bone of the spinous process. This permits tissue ingrowth into the implants and the anchor thus providing the system with biological fixation.

Figure 26A:
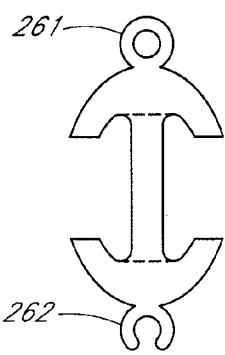
FIG. 26A shows a front view of an alternative spinous process anchor according to one embodiment.
Figure 26B:
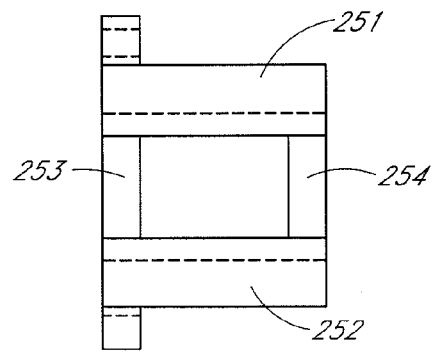
FIG. 26B shows a side view of the alternative spinous process anchor of FIG. 26A.

Modifications to the anchor of FIGS. 25A and 25B are also contemplated which could enhance the short term fixation of the anchor. One set of features that could enhance short term fixation include rings 261 or partial rings 262 attached to the top 251 and bottom roofs 252 at one end as shown in FIGS. 26A and 26B. The ring 261 and partial ring 262 could accommodate screws to provide temporary fixation to the spinous process. Alternatively, teeth could be cut on the outside of the top and bottom roofs to increase resistance to relative motion of the anchor with respect to the spinous process. In a similar manner, the outside of the top and bottom roofs could be made of porous materials such as Zimmer's trabecular metal or a metal porous coated with beads or plasma spray.

Fixation of the one or more implants to the anchor of FIGS. 25A and 25B, as well as to the anchor of FIGS. 26A and 26B could be done using the means and methods already described for attaching implants to hardware. The uprights would serve as the members about which the implants could be passed.

Fixation to the spinous process could also be accomplished with a thimble 281 shown in FIGS. 28A and 28B. It has two arms 282 and 283 with an opening at one end 284. It has a curvilinear groove 285 in cross section that runs along both arms 282 and 283 and serves to align the implant with the thimble.

The thimble 281 could be assembled to a spinous process in the following manner. A small hole is created in the interspinous ligament at either the superior or inferior surface of the spinous process. One arm of the thimble (282 or 283) is passed through the hole so that the arms are separated by the spinous process. This method could be advantageous for small spinous processes, such as those seen in the cervical spine. To mate with a spinous process in the cervical spine, it may be advantageous to have the inner aspect of the thimble shaped to match the bone receiving it. Also, it may be advantageous to fix the thimble to the spinous process and this could be accomplished with a screw driven through a hole (not shown) in one or both of the arms 282 or 283 of the thimble 281.

Once the thimble is in place, an implant can pass to the spinous process, wrap around the spinous process while in alignment with the thimble, be tightened so as to bring the implant into contact with the thimble, then passed to the inferior vertebral body for further tensioning and fixation.

In summary, a variety of hardware has been described that can be used to fix one or two implants in a position generally aligned with the disc space between adjacent vertebral bodies so as to treat a targeted disc and limit or prevent torsion of the targeted spinal disc.

To perform the insertion of the hardware and implants contemplated in a less invasive way, various instruments may be used by the surgeon. FIG. 29 shows the top view of a multi-functional surgical instrument 300. The instrument 300 has a handle 292, and three arms 293, 294, 295. Arms 293 and 295 are symmetric about a line through the handle 292 and each arm features two holes 296 and 297. The central arm 294 has a stationary element 299 and a movable arm 298. The movable arm rotates about a pin 2991. At the handle end of the movable arm, there is a ratchet mechanism 2981 to permit controlled positioning of the movable arm 298 with respect to the stationary arm 299. The ratchet mechanism 2981 mates with a ratcheting element (not shown) on the handle 292. Motion of the movable arm is permitted in one direction of rotation about the pin 2991 and prevented in the opposite direction by means of teeth (not shown). To hold the movable arm in position, there is a spring element 2982 in the space between the movable arm 298 and the handle 292. In some embodiments, the arms have a curvature that follows the contour of a subject's skin. While in some embodiments the arms may contact a subject's skin, in other embodiments, the arms are lifted and removed from the subject's skin.

The central arm 294, the stationary element 299, movable arm 298, the pin 2991, the ratchet mechanism 2981 and the spring element 2982 form a bone clamp. The purpose of the bone clamp is to hold the surgical instrument to the spinous process. The faces of the bone clamp 2992 and 2983 may be configured to mate with particular bone geometry. Also, the bone clamp elements may be modified to serve as a combination bone punch and bone clamp so that it could create a hole in the spinous process based on the geometry of the faces of the bone clamp 2992 and 2983 and then hold that position. Specifically, the faces of the bone clamp 2992 and 2983 could be pointed so that when the movable arm 298 is moved towards the handle 292, bone is crushed to create a hole in the spinous process.

Figure 30:
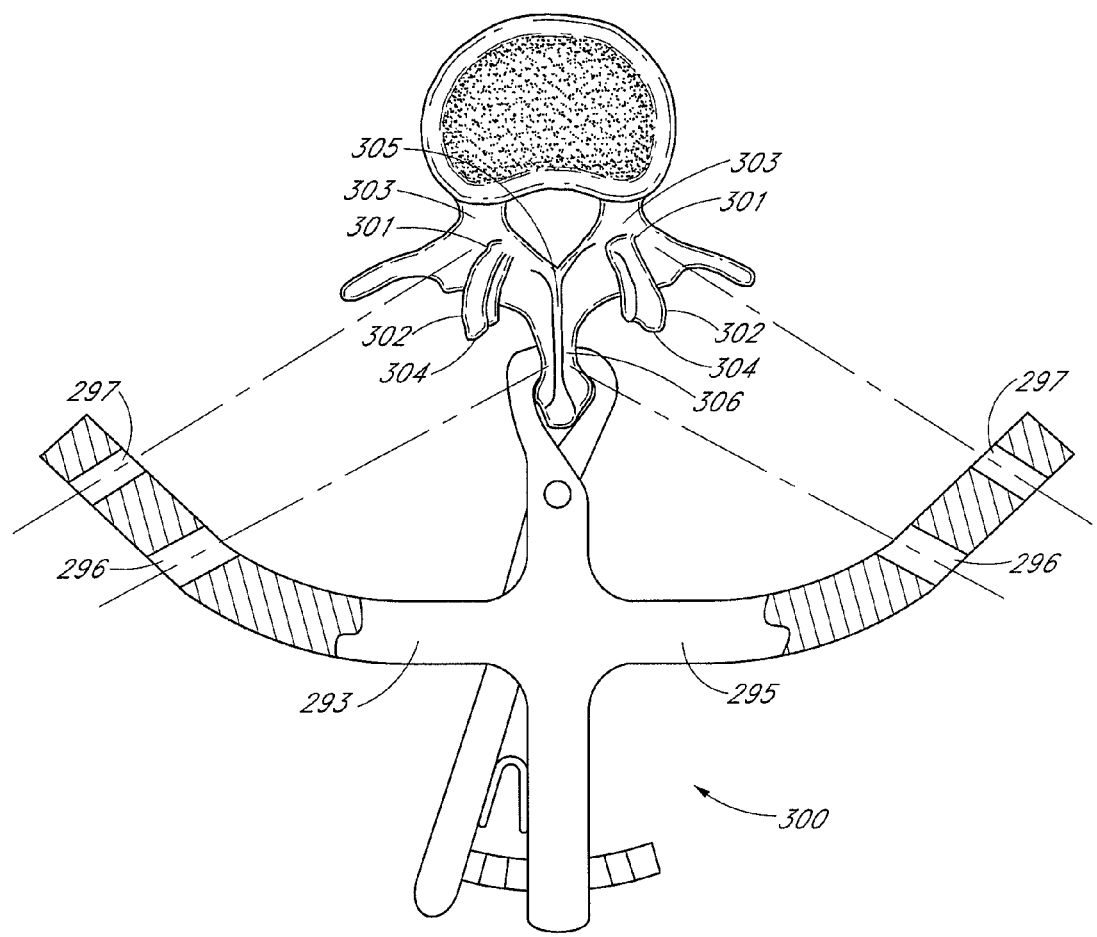
FIG. 30 shows an alternate top view of the multi-functional surgical instrument of FIG. 29 attached to a lumbar spine.

The holes 296 and 297 of the arms 293 and 295 are oriented to align a series of locations. FIG. 30 shows an alternate top view of the instrument 300 of FIG. 29 attached to a lumbar spine. The holes 297 are aligned with the location desired for fixation to the inferior vertebral body. As shown in FIG. 30, one possible location 301 is at the intersection of the mamillary process 302 with the pedicle 303.

Depending on the subject, the size of the instrument may vary. In addition, specific features of the instrument, such as the clamping portion, may vary. In some embodiments, different instruments are used to accommodate different subjects, while in other embodiments, a single instrument is provided that is adjustable. The instrument may have detachable portions (e.g., the arms) that are removable and can be replaced subject to subject. Alternatively, the position of the holes could be made adjustable by creating hollow tubes, which represent the holes 296 and/or 297, and configuring the instrument to permit the tubes to controllably slide with respect to the arms.

The holes 296 are aligned with the point 306 on or near the spinous process 305 of the superior vertebral body and a second point 304 just posterior to bone that prevents one or more implants from traversing a linear path between the points of fixation on the inferior vertebral body to the fixation on the superior vertebral body. In the example shown in FIG. 30, the second point 304 is just posterior to the tip of the mamillary process of the inferior vertebral body. It is also noted that the axis of the hole 296 on the right arm 295 may intersect with the axis of the hole 297 on the left arm 293 of the instrument. Likewise, the axis of the hole 296 on the left arm 293 may intersect with the axis of the hole 297 on the right arm 295 of the instrument.

Figure 31A:
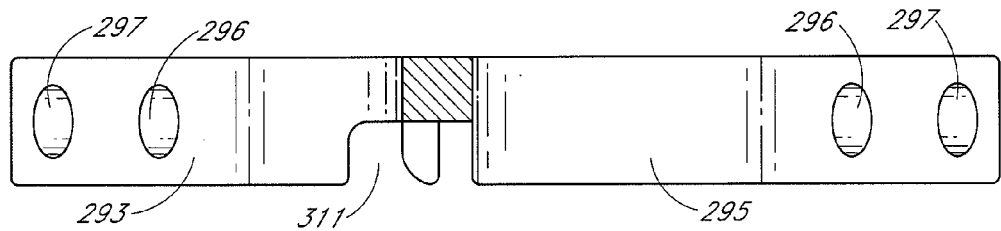
FIG. 31A shows one embodiment of a front section view of a multi-functional surgical instrument, with the movable arm removed for purposes of clarity, according to one embodiment.

FIG. 31A shows a front section view as defined by section line A-A in FIG. 29 of the multi-functional surgical instrument of FIG. 29, with the movable arm removed for the purposes of clarity. The holes 296 and 297 in the arms 293 and 295 could be circular or non-circular in shape. Also as shown, the holes 296 and 297 are aligned in the same plane, which is coincident with the position of the bone clamp (not shown). A cavity 311 is made in the lower part of the instrument to receive the movable arm.

Figure 31B:
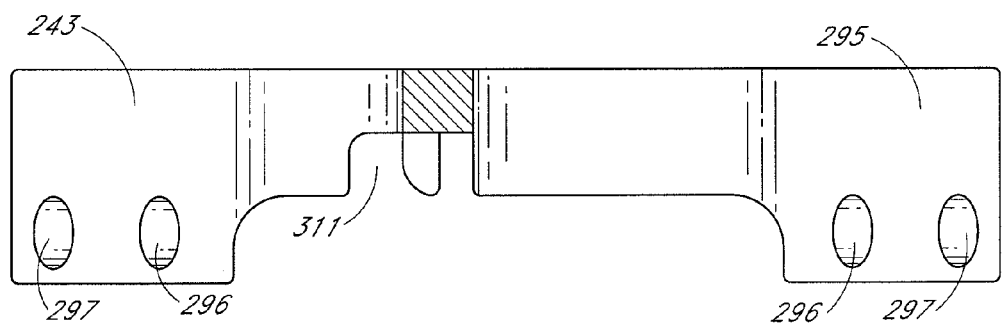
FIG. 31B shows a second embodiment of a front section view of a multi-functional surgical instrument, with the movable arm removed for purposes of clarity.

FIG. 31B shows an alternative front section view as defined by Section Line A-A in FIG. 29 of a surgical instrument, with the movable arm removed for purposes of clarity. In this embodiment, the holes 296 and 297 are aligned but offset from the bone clamp. This embodiment could be useful when it is desired to use an outrigger to fix to a position below the spinous process, or when the implant is intended to pass under the spinous process or around the spinous process.

Figure 31C:
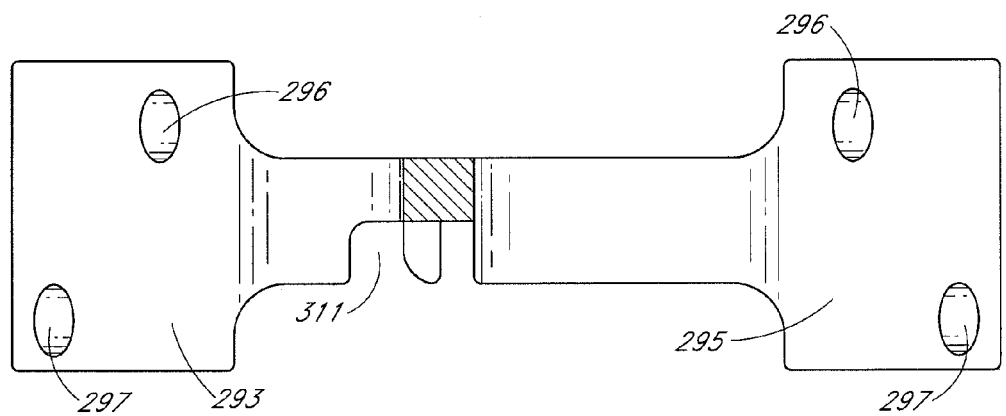
FIG. 31C shows a third embodiment of a front section view of a multi-functional surgical instrument, with the movable arm removed for purposes of clarity.

FIG. 31C shows yet another alternative front section view as defined by Section Line A-A in FIG. 29 of a surgical instrument, with the movable arm removed for purposes of clarity. In this embodiment, the holes 296 and 297 are offset in opposite directions.

A variety of hardware are intended to pass through each hole 296 and 297, and it is preferable that each hole 296 and 297 be of the same cross section so as to be capable of receiving the same set of tools. Further, it is preferable that the shape of the holes be matched to the shape of the implants being used and also to the shape of the fixation to be used on the inferior vertebral body. For example, an implant of the shape shown in FIG. 6 would be preferably matched to a staple type fixation of FIG. 9A which in turn would be preferably matched with a generally oval shape cross section of holes 296 and 297.

Figure 32A:
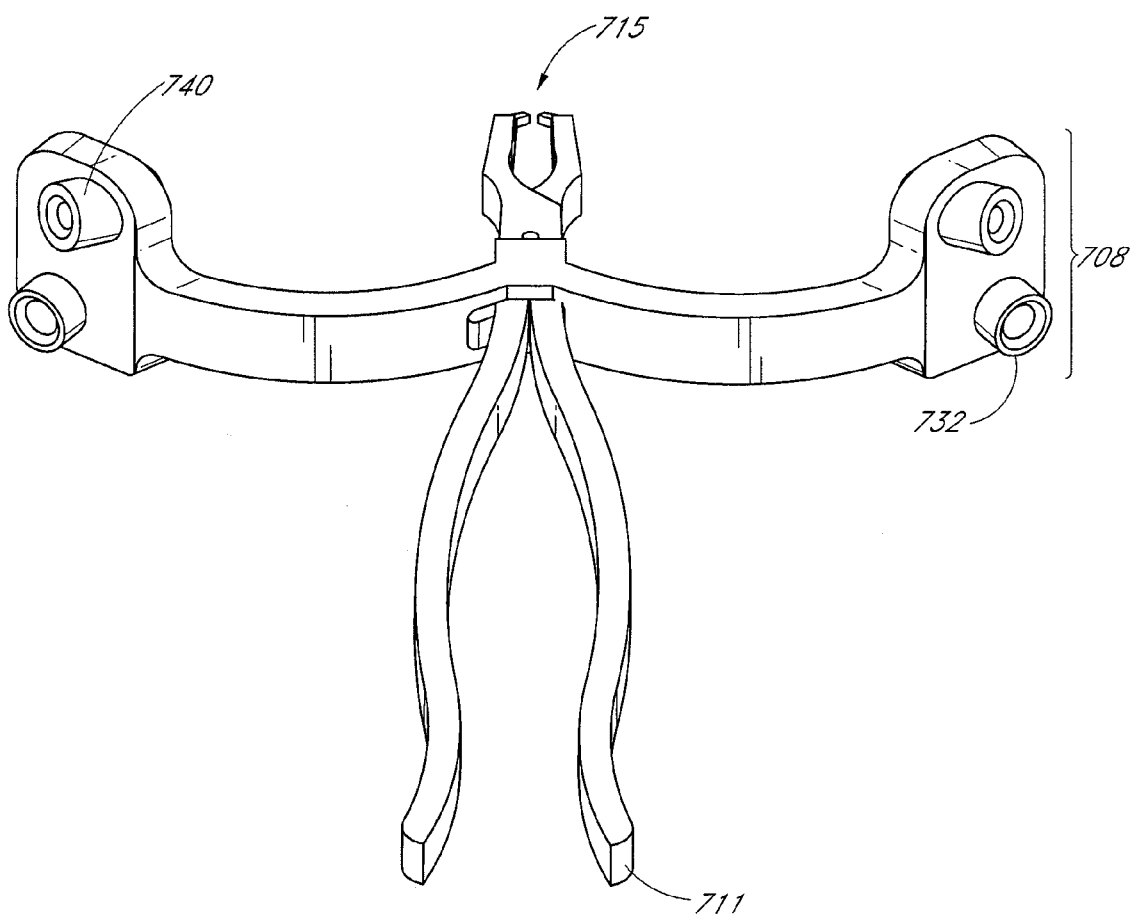
FIG. 32A shows an oblique view of a multi-functional surgical instrument according to one embodiment.
Figure 32B:
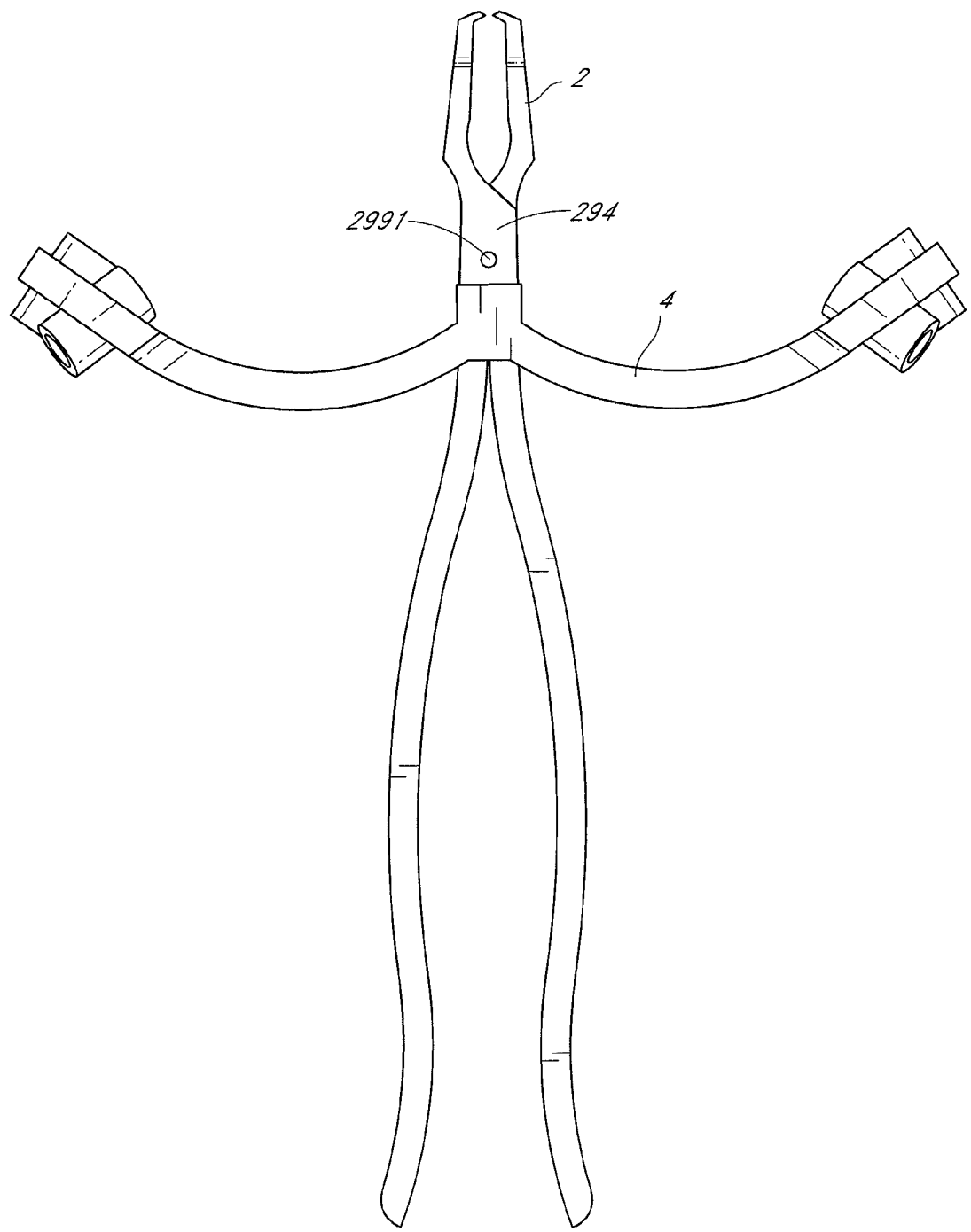
FIG. 32B shows an alternative top view of the multi-functional surgical instrument of FIG. 32A.

FIG. 32A illustrates an oblique view of an alternate embodiment of a multi-functional instrument 708. The instrument 708 includes a handle 711, tines 715, anchor holes 732 and passing holes 740. FIG. 32B illustrates an alternative top view of the multi-functional instrument, and points out additional features of the instrument, including a fixed arm 294, a movable arm 2, a pin 2991 and a fixed arm drill guide 4.

Figure 32C:
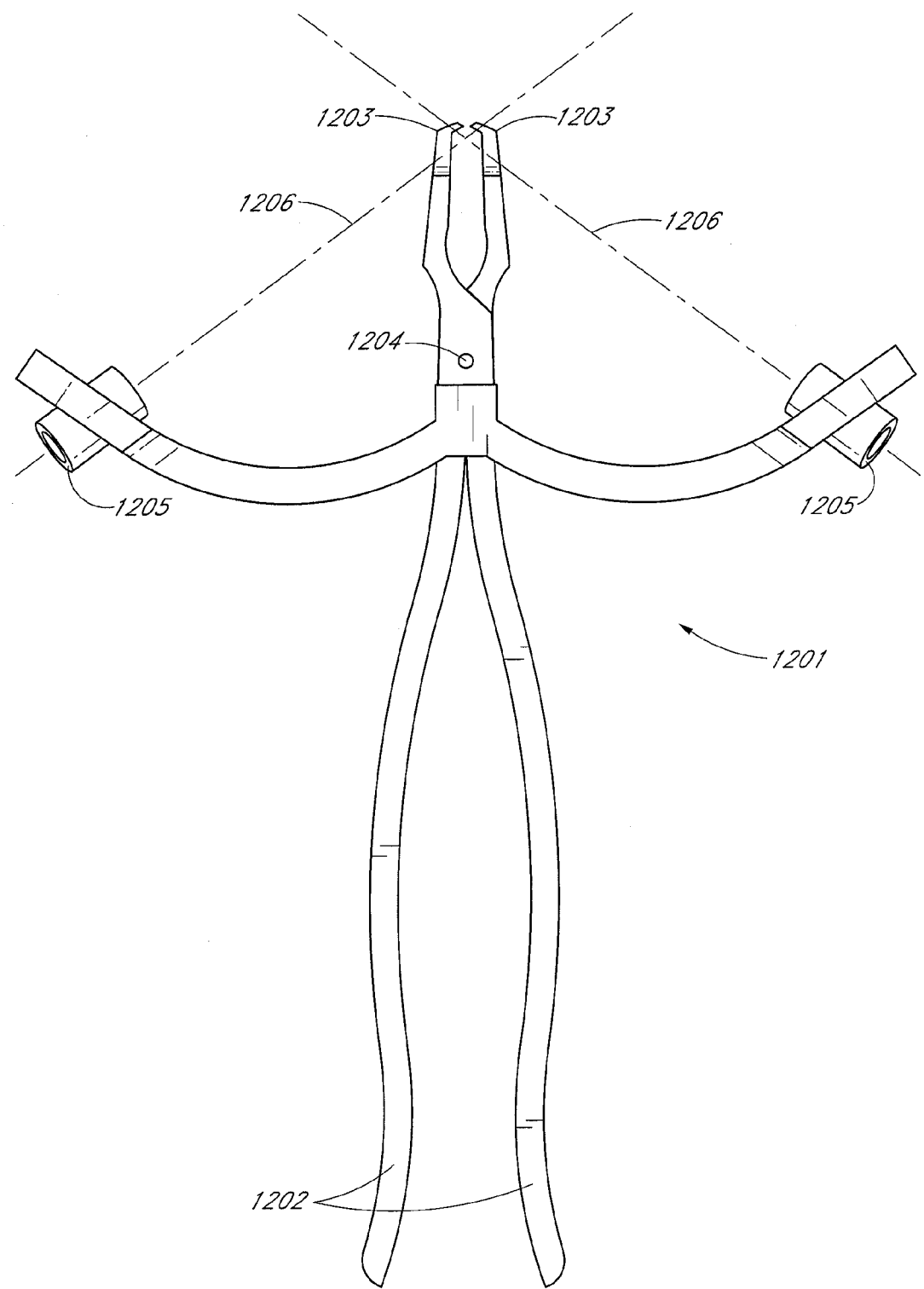
FIG. 32C shows an alternative multi-functional surgical instrument according to one embodiment.
Figure 32D:
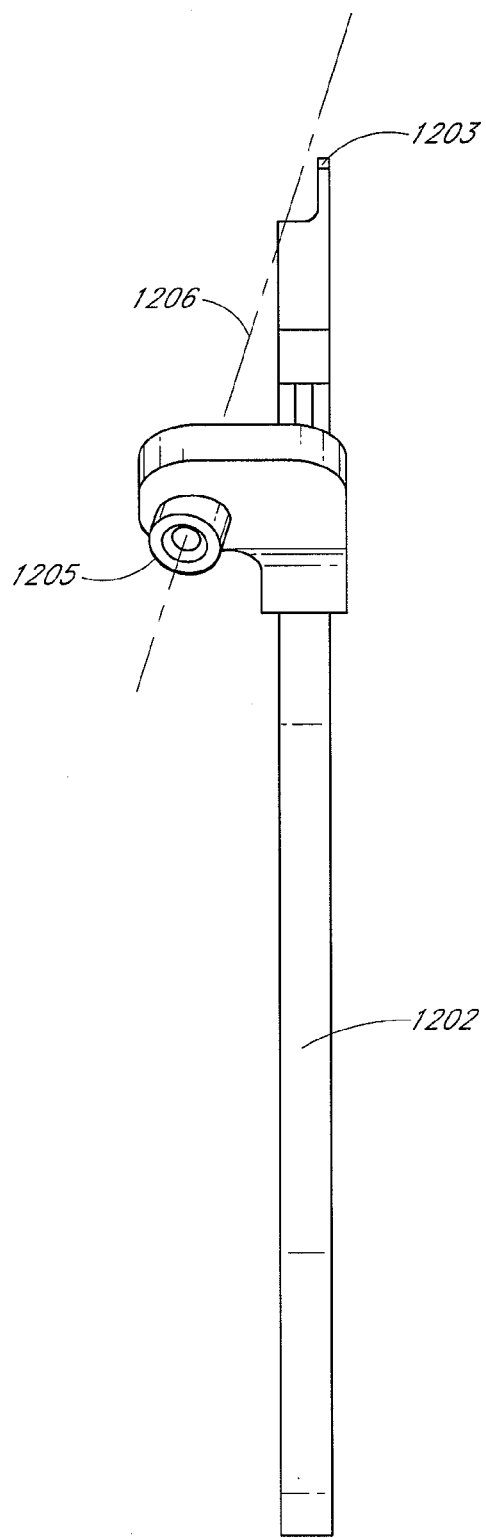
FIG. 32D shows a side view of the multi-functional surgical instrument of FIG. 32C.

FIGS. 32C and 32D show a top view and side view, respectively, of an alternate embodiment of a multi-functional surgical instrument 1201 having a combination anchor and passing hole 1205 according to one embodiment. A multi-functional instrument as shown in FIGS. 32C and 32D may be used in conjunction with various types of hardware and implants (including suture anchors) to provide torsional stabilization. The instrument 1201 includes two handles 1202, two tines 1203, a hinge 1204 and a combination anchor and passing hole 1205. The axis of the combination anchor and passing hole 1205 is shown as 1206. While the multi-functional instruments shown in FIGS. 29-32D may not be necessary to accomplish the methods of torsional stabilization described herein (for example, several different instruments may be used for clamping and alignment), using the multi-functional instruments described herein allow for advantageously using a single instrument capable of performing multiple functions with precision and accuracy.

Figure 33:
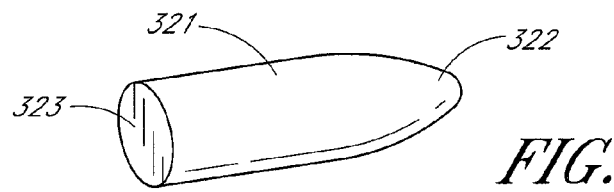
FIG. 33 shows a dilator.

In addition to the instruments and hardware described above, others may also be used to facilitate the methods, systems and apparatuses described herein. FIG. 33 shows a dilator 321. It has a leading end 322 which transitions the dilator from the cross section 323 of the trailing end to a point. The leading end 322 can be configured as a bullet nose, a conical end or any other gradually tapering surface suitable for blunt dissection of the muscle tissue of the neck and back. The cross section 323 is selected so that the dilator has a slidable fit with the holes 296 and 297 of the instrument.

Figure 34:
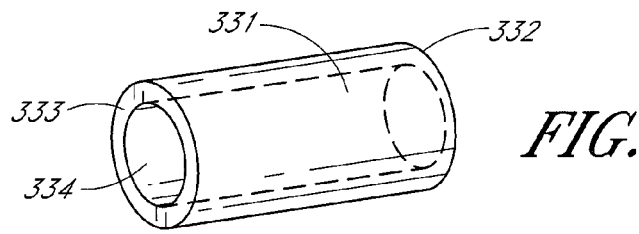
FIG. 34 shows a cannula.

FIG. 34 shows a cannula 331. It has a leading end 332 which transitions the dilator from the cross section 333 of the trailing end to an edge. The leading end 332 can be configured as a portion of a sphere, a portion of a cone or any other gradually tapering surface suitable for blunt dissection of the muscle tissue of the neck and back. The cross section 333 is configured so that the dilator has a slidable fit with the holes 296 and 297 of the instrument. The inner hole 334 of the cannula is configured to be a reduced size version of the cross section 333.

A reduced size dilator is also contemplated, similar to that shown in FIG. 33. The reduced size dilator would have a smaller cross section 323 to create a slidable fit with the inner hole 334 of the cannula. The assembly of the cannula and the reduced size dilator could be used to dissect tissue in a path followed by removal of the reduced size dilator to create a working channel within the cannula.

Figure 35A:
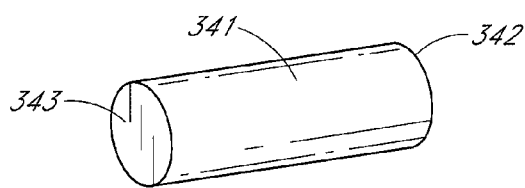
FIG. 35A shows an oblique view of a tamp.
Figure 35B:
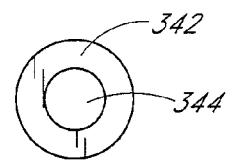
FIG. 35B shows an end view of the tamp of FIG. 35A.

FIGS. 35A and 35B show a tamp 341. It has a leading end 342 which has a reduced size surface 344 suitable for impacting or pushing on the implant or anchor as necessary. It has a cross section 343 that matches the holes 296 and 297 of the instrument and permits the tamp to slide within the hole. It can also be made in a reduced section size so that the outside of the tamp fits slidably within the hole 334 of the cannula.

Figure 36:
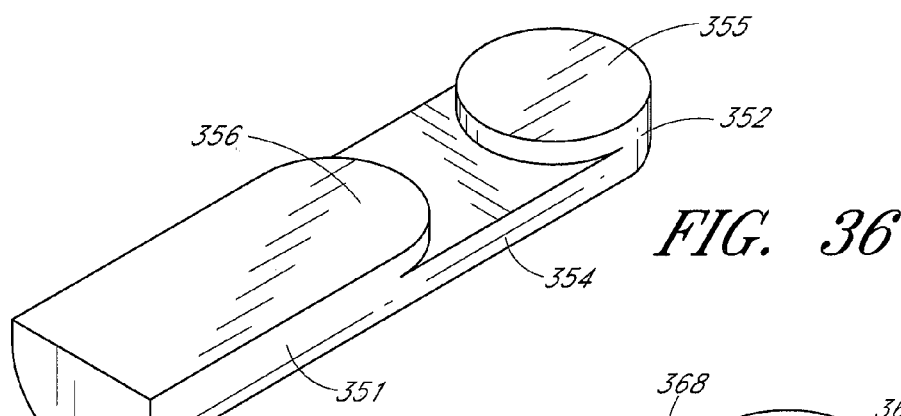
FIG. 36 shows a hooker.

FIG. 36 shows a hooker 351. It has a leading end 352 and a trailing end 353. The leading end 352 can be configured as a portion of a sphere, a portion of a cone or any other gradually tapering surface suitable for blunt dissection of the muscle tissue of the neck and back. The trailing end 353 can be shaped to be a portion of the hole 296 and 297 so that it can fit slidably within a hole, while not filling the entire space of the hole 296 and 297. The hooker 351 has a reduced section portion 354. Adjacent to the reduced section are curved surfaces 355 and 356.

Figure 37:
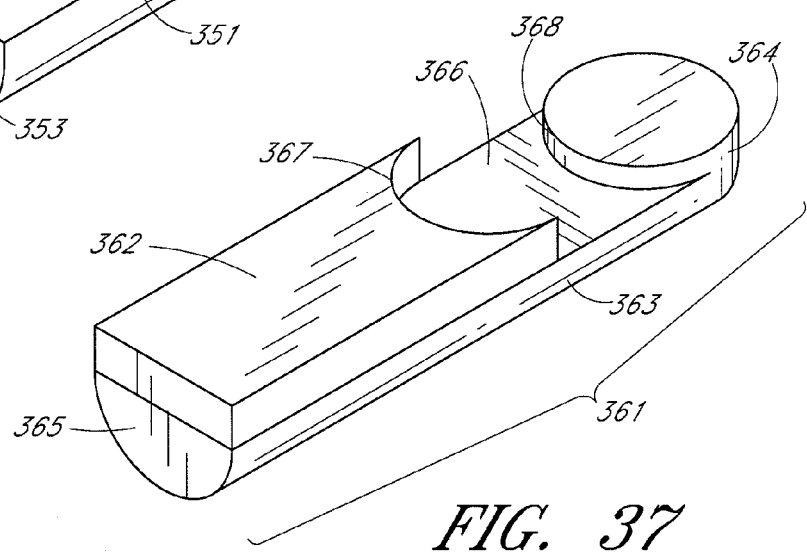
FIG. 37 shows a portion of a grabber.

FIG. 37 shows a portion of a grabber 361. It has two pieces, a slider 362 and a fixed element 363. It has a leading end 364 and a trailing end 365. The leading end 364 can be configured as a portion of a sphere, a portion of a cone or any other gradually tapering surface suitable for blunt dissection of the muscle tissue of the neck and back. The trailing end 365 is composed of portions of both the slider 362 and the fixed element 363. The trailing end 365 can be shaped to fill a portion of the hole 296 and 297 so that it can fit slidably within the hole, while not filling the entire space of the hole 296 and 297. The fixed element 363 is of reduced section until the leading end 364. Between the slider 362 and the leading end 364 is a space 366. To best grab an implant, the slider end 367 adjacent to the space 366 can be configured to mate with the trailing portion 368 of the leading end 364. The mating elements 367 and 368 provide a means to grab an implant between them.

Figure 39:
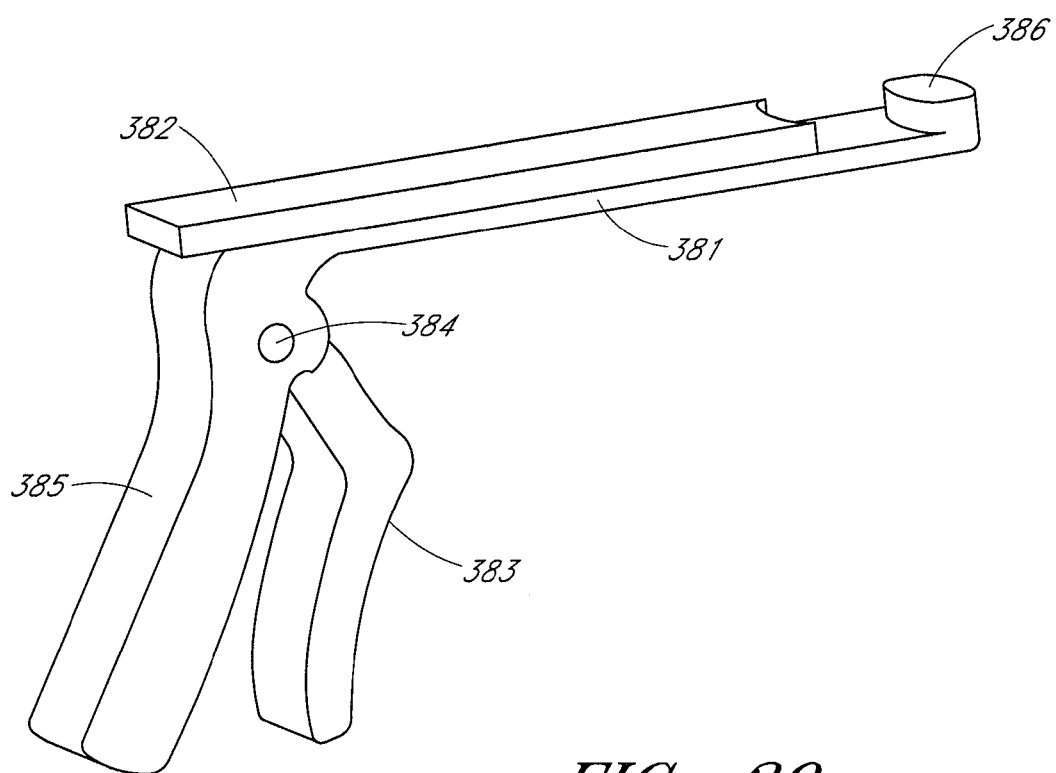
FIG. 39 shows an oblique view of a kerrison-type rongeur configured as a grabber.

Incorporation of the grabber 361 into an instrument is contemplated as shown in FIG. 39, which is a Kerrison type rongeur configured as a grabber. The Kerrison is a widely used surgical instrument composed of a fixed element 381, a slider 382, a moveable handle 383 and a hinge 384. The movable handle 383 has a portion of it extending to and fixing to the slider 382. When the movable handle 383 is rotated about the hinge 384 towards the handle 385 of the fixed element 381, the slider 282 is moved towards the leading end 386.

Figure 38:
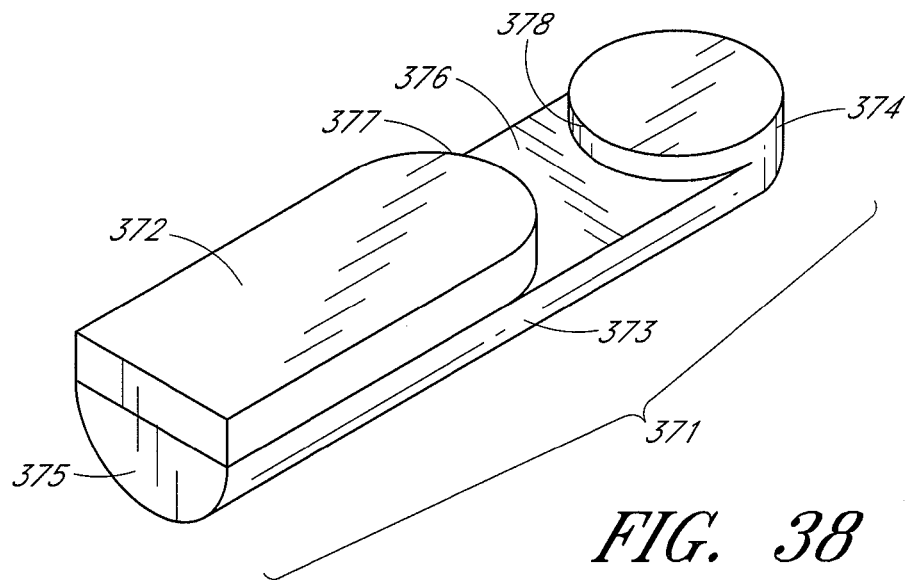
FIG. 38 shows a portion of a puller.

In some configurations, it may be desirable to hold an implant while letting the implant slide relative to the holding instrument. FIG. 38 shows a portion of a puller 371 intended to hold an implant while letting the implant slide relative to the holding instrument. It has two pieces, a slider 372 and a fixed element 373. It has a leading end 374 and a trailing end 375. The leading end 374 can be configured as a portion of a sphere, a portion of a cone or any other gradually tapering surface suitable for blunt dissection of the muscle tissue of the neck and back. The trailing end 375 is composed of portions of both the slider 372 and the fixed element 373. The trailing end 375 can be shaped to fill a portion of the hole 296 and 297 so that it can fit slidably within the hole, while not filling the entire space of the hole 296 and 297. The fixed element 373 is of reduced section until the leading end 374. Between the slider 372 and the leading end 374 is a space 376. To best pull an implant, the slider end 377 adjacent to the space 376 can be configured as a portion of a cylinder while the trailing portion 378 of the leading end 374 has a similar cylindrical shape. When the slider 372 is slid towards the leading end 374, it is possible to hold an implant in the space 376. Due to the small contact area resulting from the cylindrical surfaces apposing each other, the implant will have an increased tendency to slide. Incorporation of the puller into a Kerrison type rongeur is analogous to that described for the grabber.

FIGS. 40A, 40B and 40C show a side view, top view, and front view, respectively, of an inserter 391. It has a leading end 392 with a mating surface 393 that mates with an anchor intended to be impacted into place such as a staple. It has a trailing end 394 that slidably fits within a cannula, such as that of FIG. 34. A reduced section portion 395 is adjacent to the leading end 392, which connects the leading end 392 with the trailing end 394. The reduced section portion 395 helps to remove material from the inserter such that there is space for an implant when inserting an anchor preassembled with an implant, such as that described in FIG. 9B. Additionally, the reduced section portion 395 permits passing of grabbers, hookers and pullers below the inserter to snare the implant. The mating surface 393 is reduced in size from the cross section of the inserter 394, as shown in FIG. 40C, so as to permit an implant preassembled onto the anchor to pass adjacent to the mating surface and into the reduced section portion 395.

FIGS. 41A, 41B and 41C show a side view, top view and front view, respectively, of an alternative inserter 401. The inserter has a leading end 402 with a slot 403 that mates with an anchor intended to be rotated into place such as that shown in FIG. 10. It has a trailing end 404 that slidably fits within a cannula, such as that of FIG. 34, but is of the largest round cross section that can fit within the cannula. Adjacent to the leading end 402 it has a reduced section portion 405 that connects the leading end 402 with the trailing end 404. The reason for the reduced section portion 405 is to remove material from the inserter so that there is space for implant when inserting an anchor preassembled with an implant. Additionally, the reduced section portion 405 permits the passing of grabbers, hookers and pullers below the inserter to snare the implant. The leading end surface 406 is reduced in size from the circular cross section of the inserter 404, as shown in FIG. 41C, so as to permit an implant pre-assembled onto the anchor to pass adjacent to the leading end surface and into the reduced section portion 405.

It is conceived that a variety of alternative mating geometry could be incorporated into the alternative inserter replacing the slot 403 to match the anchor geometry.

Figure 42:
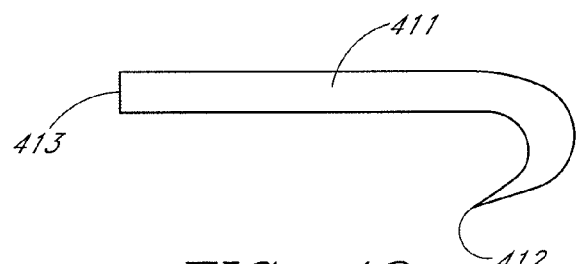
FIG. 42 shows a front view of an alternative hooker.

FIG. 42 shows a front view of an alternative hooker 411. It has a leading end 412 and a trailing end 413. The leading end 412 is offset from the trailing end and may be pointed to enhance its ability to capture the implant.

Figure 43A:
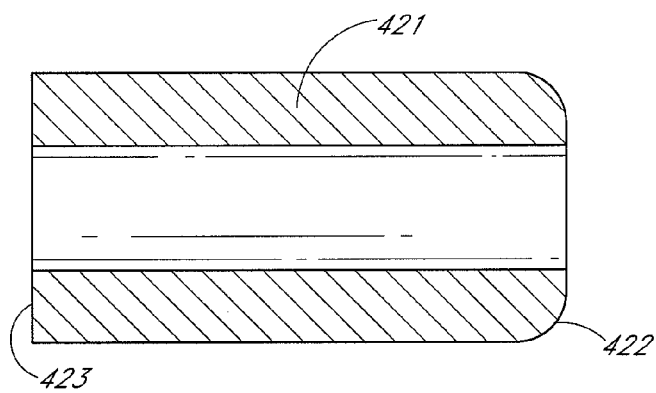
FIG. 43A shows a front section view of a combination tamp/inserter cannula.
Figure 43B:
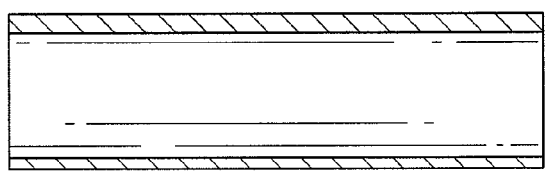
FIG. 43B shows a top section view of the combination tamp/inserter cannula of FIG. 43A.
Figure 43C:
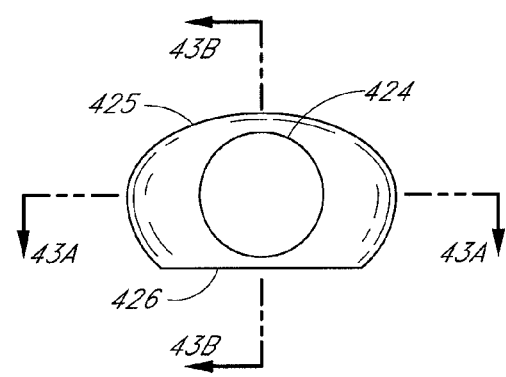
FIG. 43C shows a side view of the combination tamp/inserter cannula of FIG. 43A.

FIGS. 43A, 43B and 43C show a combination tamp/inserter cannula 421. The combination tamp/inserter cannula has a leading end 422, a trailing end 423 and a central bore 424. The leading end 422 is generally blunted for pushing on the implant. As seen in FIG. 43C, the central bore 424 is circular in cross section, making it suitable to receive a screw and screwdriver. The outside 425 is generally the shape of the cross section of the hole 297, except for a flat 426. The overall shape ensures that the combination tamp/inserter cannula 421 slidably fits with the hole 297, while the flat 426 ensures that there is space within the hole for the alternative hooker 411 previously described. This configuration ensures that both the combination tamp/inserter cannula and the alternative hooker can be placed within the hole 297 of the instrument of FIG. 29.

In sum, a variety of implant alternatives and hardware alternatives to fix the implant to the inferior and superior vertebral bodies have been described. Additionally, a set of instruments have been described that can be used to assist the surgeon in positioning one or more implants between the inferior vertebral body and the superior vertebral body such that the implant is aligned with the disc space.

A preferred surgical technique can now be described. The described surgical technique utilizes the surgical instrument 300 shown in FIG. 29, although various surgical instruments may be used to perform the surgical technique. The surgical technique can begin by having a surgeon identify a spinal level to be treated. This step is optional, for in some embodiments, a spinal level location may have been pre-determined, such that identification of the spinal level need not be considered part of the surgical technique. A midline incision is made, progressing down to the level of the spinous process of the superior vertebral body. This step is also optional, for in some embodiments, an incision may have already been made as part of an open surgery. The surgical instrument of FIG. 29 is clamped onto the sides of the spinous process of the superior vertebral body. Using the holes 297 of the surgical instrument as guides, incisions are made that are aligned with the holes 297 of the instrument. These incisions are made bilaterally, although in some embodiments, an incision need only be made unilaterally on one side. Optionally, a reduced size dilator and cannula can be assembled and introduced through the holes 297 in the instrument and used to bluntly dissect down to the point of fixation on the inferior vertebral body. In one embodiment, the dilator can be temporarily removed from the cannula to incise the fascial layer. The fascia may then be incised and the dilator reassembled to the cannula. The assembly is advanced to the points of fixation on the inferior vertebral body. The dilator is withdrawn, leaving the cannula.

The anchor for fixation to the inferior vertebral body can be assembled to an implant, or preferably come preassembled to an implant. The anchor is put on an inserter. The inserter is passed through the cannula and used to fix the anchor to the fixation point. This is done bilaterally, although in some embodiments, the inserter may pass through the cannula on one side unilaterally.

A grabber, hooker or puller can be introduced through the hole 296 on the opposite arm of the surgical instrument 300 of FIG. 29 and advanced laterally toward the implant. In one embodiment, an additional skin incision is made for the grabber, hooker or puller. When the grabber, hooker or puller contacts the cannula, the cannula is retracted until it clears the grabber, hooker or puller. The grabber, hooker or puller is then further advanced to capture the implant. Once the implant is captured, the grabber, hooker or puller is retracted to bring the implant to the spinous process of the superior vertebral body. This step is repeated on both sides. In one embodiment, a dilator may be inserted to the point of contact with the cannula, so as to perform blunt dissection of the tissue, prior to use of the grabber, hooker or puller. In some embodiments, the hooker, grabber or puller can be used to pull an implant through a hole in the spinous process after making a hole in the spinous process, such as by using a combination bone clamp and bone punch as described below.

The combination bone clamp and bone punch is then used to make a hole in the spinous process suitable to receive the spinous process anchor described in FIGS. 25A and 25B. The bone clamp and bone punch are released and the surgical instrument of FIG. 29 removed. The spinous process anchor is inserted into the created hole in the spinous process. The implant is passed around the spaced apart uprights and tensioned using a hemostat or other clamping instrument. The implant is fixed in position either with a clamp such as that shown in FIG. 18A, FIG. 20A or FIG. 27, a knot tying the implant to the anchor, sutures fixing the implant to itself, or a staple fixing the implant to itself. The surgical sites can be closed in the usual manner.

An alternative surgical technique using the surgical instrument 300 of FIG. 29 is now described, in which a single implant from one inferior vertebral body is passed to and partially around the spinous process of the superior vertebral body and to the inferior vertebral body on the opposite side. The implant is flexible and capable of being placed in tension. Again, a midline incision may be made, progressing down to the level of the spinous process of the superior vertebral body. The surgical instrument may be clamped onto the sides of the spinous process of the superior vertebral body. An incision may be made aligned with the hole 297 on one arm of the instrument. A reduced size dilator and cannula may be assembled and introduced through the hole 297 in the instrument to bluntly dissect down to the point of fixation on the inferior vertebral body. In one embodiment, the dilator may be temporarily removed from the cannula to incise the fascial layer. The fascia may then be incised and the dilator reassembled to the cannula. The assembly is advanced to the points of fixation on the inferior vertebral body. The dilator is withdrawn, leaving the cannula.

The anchor for fixation to the inferior vertebral body is assembled to an implant, or preferably comes preassembled to an implant. The anchor is put on the inserter. The inserter is passed through the cannula and used to fix the anchor to a first location on an inferior vertebral body. This may be done unilaterally.

A grabber, hooker or puller is then introduced through the hole 296 on one arm of the surgical instrument of FIG. 29 and advanced laterally toward the implant. In one embodiment, an additional skin incision may be made for the grabber, hooker or puller. When the grabber, hooker or puller contacts the cannula, the cannula is retracted until it clears the grabber, hooker or puller. The grabber, hooker or puller is then further advanced to capture the implant. Once the implant is captured, the grabber, hooker or puller is retracted to bring the implant to the spinous process of the superior vertebral body. In one embodiment, a dilator may be inserted to the point of contact with the cannula, so as to perform blunt dissection of the tissue, prior to use of the grabber, hooker or puller. In some embodiments, the hooker, grabber or puller can be used to pull an implant through a hole in the spinous process after making a hole in the spinous process, such as by using a combination bone clamp and bone punch as described below.

The combination bone clamp and bone punch is then used to make a hole in the spinous process. One skilled in the art will appreciate that in other embodiments, a hole in the spinous process can be made prior to fixation of an anchor and implant to the inferior vertebral body. The bone clamp and bone punch are released and the surgical instrument of FIG. 29 removed.

The implant is then fixed to the spinous process by passing the implant through the created hole in the spinous process, along the side of the spinous process, looping under the spinous process, along the side of the spinous process and back through the created hole. In an alternative embodiment, the implant passes under the spinous process, through the created hole in the spinous process and under the spinous process again. In another embodiment, the implant passes over the spinous process, through the created hole in the spinous process and then over the spinous process again.

Optionally, after fixing the implant to the spinous process, the surgical instrument of FIG. 29 can be reapplied and its alignment checked with the initial incision prior to fixation of the implant to a second location on the inferior vertebral body.

A second incision (on the opposite side) is made for inferior vertebral body fixation aligned with the hole 297 of the instrument. An assembled cannula and reduced size dilator is advanced in the manner previously described to the point of fixation. The dilator can then be removed.

A grabber, hooker or puller is then introduced through the hole 296 of the instrument arm opposite the second incision to engage the implant, and then be advanced to the cannula. An alternative hooker is introduced through the cannula and advanced to the point of fixation. The cannula is withdrawn completely. The grabber, hooker or puller is advanced to pass beyond the alternative hooker. The alternative hooker is then withdrawn until it captures the implant. The grabber, hooker or puller is retracted. A combination tamp/inserter cannula is introduced through the hole 297 and advanced to the implant. As the combination tamp/inserter cannula is advanced, the alternative hooker is retracted, thus tensioning the implant. The combination tamp/inserter cannula is advanced to the point of fixation. A screw is then inserted through the tamp/inserter cannula and fixed through the implant into the bone. The combination tamp/inserter cannula is removed. The implant is cut into two pieces between the screw fixation and the site of connection to the alternative hooker. The alternative hooker is removed (with the unsecured piece of implant) and the surgical sites closed in the usual manner.

There are a variety of alternative surgical methods that could be done to treat a spinal level by fixing the superior vertebral body to the inferior vertebral body using the implants, instruments and methods of the current application. These include fixation of the implant to the superior vertebral body and then passing it bilaterally to the inferior vertebral body. Additionally, optional additional steps could be performed to enhance fixation of the implant. For example, one additional step would be to use an implant with some porosity (such as a polymeric fabric) and to abrade the periosteum and bone surfaces where there is implant contact. The abrasions could be done with a variety of burrs or files. With abrasion, bleeding bone can be exposed and thus biological ingrowth into the implant may be possible. This biological ingrowth can enhance the fixation of the implant.

It is conceived that the implants, hardware, instruments and methods of the current application could be used on their own. It is also conceived that they could be used in addition to other methods of treatment. Specifically, the current application could be used in combination with discectomy. This would result in removal of the chemical and physical impact of the herniated nucleus, while providing torsional reinforcement to prevent abnormal torsional kinematics. Also, the current application can be used to supplement the use of a spinal artificial disc. In patients receiving artificial discs, a large amount of the annulus is removed, thus destabilizing the spine torsionally. This is supported by the significant percentage of patients who have facet pain following placement of an artificial disc.

The current application can also be used in combination with a plug or patch to repair the annulus. There are annular repair products that attempt to fix tears in the annulus by applying a patch or similar product to the site of the tear. Anulex ™ is one such company attempting to develop this technology. In its product, a patch is sutured to the annulus. However, this is very difficult to perform and maintain, for when a spinal level experiences significant torsion, it is likely that the sutures will be unable to maintain fixation. In contrast, the current application can used as described and augmented with a simple porous plug of polymeric material, preferably one that is resorbable, to fill the hole and provide a scaffold for cells to heal the tear. In this instance, it might be advantageous to expose bleeding bone adjacent to the plug to provide a larger source of cells and thereby stimulate healing. Alternatively, the current application can be used with a product such as Anulex's which allows for fixation in addition to a scaffolding. The use of the current application would reduce the load on the sutures in the Anulex product, thus increasing the potential for repair.

The implants, hardware, instruments and methods of the current application can also be used to treat multiple levels in a single surgical procedure. In addition, the implants, hardware, instruments and methods of the current application could also be used to provide multidirectional stability to the spine for multilevel treatment. That is, instead of treating a single level, multiple levels could be treated simultaneously. To provide multilevel treatment, a preferred method of treating the levels would be to install hardware to the vertebral body below the lowest disc level to be treated (as described in this application) and above the highest disc level to be treated (as described in this application). Treatment in this manner may require that the implants no longer be aligned with the disc space. However, there are some advantages to this approach:

- The line of action of the implants would be posterior to the pedicle fixation that is commonly used, resulting in less force to resist the moments applied to the spine and thus reducing the risk of hardware loosening found in existing pedicle screw based systems.
- The surgery would be percutaneous thus reducing the surgical trauma.
- The triangular fixation resulting from bilateral fixation to the inferior vertebral body and unilateral fixation to the superior vertebral body would provide multidirectional stability in a way not found in common pedicle screw constructs.

Additional Embodiments

Additional systems, methods and apparatuses related to providing torsional stabilization to a spinal motion segment are discussed below.

Suture as a Stabilizing Implant

As described above, various stabilizing implants (such as those shown in FIGS. 4 through 8) may be placed in the spine, often in a generally transverse manner, to provide torsional stabilization to a spinal motion segment. According to one embodiment, the stabilizing implant may be comprised of wires or cables made of a metal, a metal alloy (such as nitinol), a mono or multifilament polymeric material, or combinations thereof. In a preferred embodiment, the stabilizing implant is comprised of one or more sutures placed in tension between multiple locations along the spine to limit axial torsion in one or more directions. The amount of tension in one or more sutures may vary between 5 and 200 N, more preferably between 10 and 150 N. In some embodiments, the sutures may be used on their own as a stabilizing implant, while in other embodiments, the sutures are used as a stabilizing implant in addition to other implants.

Stabilizing implants may be fixed to various locations of the spine by using one or more anchoring devices. These anchoring devices may include the anchors shown in FIGS. 9 through 12, including one or more staples, threaded bone anchors, offset anchors, as well as various other anchors and combinations thereof. In some embodiments, one or more suturing anchors (as shown in FIG. 44) may also be used.

Figure 44:
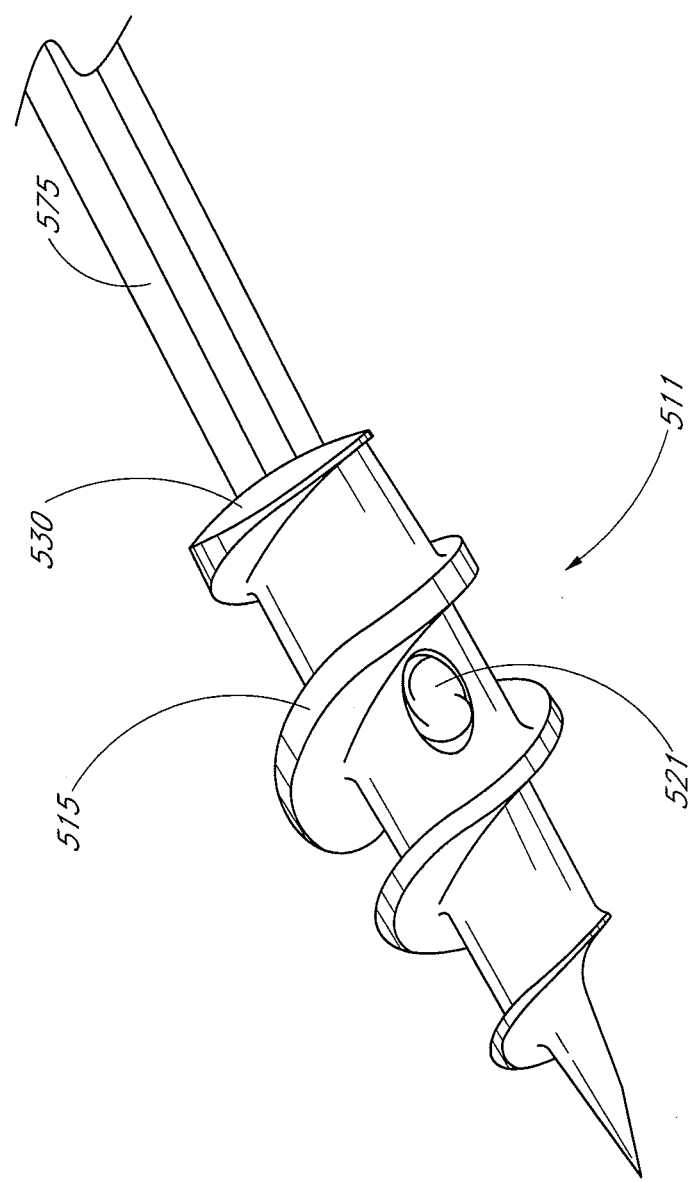
FIG. 44 shows a suture anchor according to one embodiment.

FIG. 44 illustrates a suture anchor 511 according to one embodiment that includes a threaded anchoring portion 515, a suture eye 521, and a receiving hole 530. The suture anchor 511 may serve to anchor an end point of one or more sutures 575 that enter through the receiving hole 530. The suture anchor 511 may be comprised of various materials, including but not limited to stainless steel, titanium, titanium alloy, nitinol, composites (such as combinations of TCP/PLGA), polymeric materials such as PEEK, polyglycolic or polylactic acid polymers, and combinations thereof.

The suture eye 521 may be of varying configurations and geometries, and may be used to hold one or more pieces of suture 575. In one embodiment, one or more pieces of suture may be looped through the eye 521. Additionally, the eye 521 may also hold a knot of one or more sutures 575. In another embodiment, the suture anchor 511 may be a knotless system such that there is no need to loop a suture around an eye portion of a suture anchor. One preferred embodiment of a suture and anchor combination uses a single suture that is attached to the anchor in the midst of the suture, resulting in two ends of a single suture for use as the stabilizing implant. This may be achieved by passing the suture through an eye 521 in the anchor, or by knotting the suture to itself after passing through an eye 521. This preferred embodiment in that it enables use with an endobutton (shown in FIG. 46) to tension the stabilizing implant by tying one end of the suture to the other.

One embodiment of the present application may use one or more suturing anchors 511 (as shown in FIG. 44) to torsionally stabilize a spinal motion segment by placing in tension one or more sutures 575 between an inferior vertebrae and a superior vertebrae. The stabilizing implant may include sutures 575 that are preloaded and fixed to one or more anchors 521. In another embodiment, one or more suturing anchors 511 may be used in conjunction with an endobutton to tension one or more sutures between adjacent vertebrae to resist axial torsion.

In embodiments that are comprised of one or more sutures, the sutures may be absorbable and made, for example, of a biodegradable polymeric fiber. Alternatively, the sutures may be non-biodegradable and made of a material such as polypropylene, polyester or polyethylene. One of skill in the art will appreciate that various sutures may be used as a stabilizing implant and the choice of materials is not limited to those materials mentioned above. Furthermore, the stabilizing implant may use one or more sutures that may be braided or unbraided. In one embodiment, a suture used as a stabilizing implant is constructed of a monofilament polymer chain having a braided jacket.

As shown in FIG. 44, the anchoring portion 515 of the suture anchor 511 may be externally threaded to facilitate insertion of the suture anchor into the bone. In one embodiment, the suture anchor 511 may be inserted into a pre-drilled hole of a bone. In another embodiment, the suture anchor 511 may be self-tapping by using the threaded anchoring portion 515. Regardless of the type of anchor used, one or more instruments may be used to facilitate placement of the anchor in a desired location of the bone.

FIG. 45A illustrates a side view of an anchor driver 501 according to one embodiment that may be used to facilitate and drive an anchor into a bone. The anchor driver 501 includes a handle end 505 and a driving end 508. The anchor driver 501 may be generally cylindrical in shape, and as shown in FIG. 45A, the handle end 505 may have a greater circumference than the driving end 508. The handle end may be affixed to a handle (not shown).

FIG. 45B illustrates a cross-sectional top view of the anchor driver of FIG. 45A. The driving end 508 of the anchor driver includes a protrusion 509 capable of making contact with an anchor head. In some embodiments, the protrusion 509 (which is also shown prominently in the exploded side view of the tip of the anchor head in FIG. 45C) may shapely fit into a hole in the anchor head to engage the tip of the anchor driver with the suture anchor. When the anchor driver and anchor head are engaged, the anchor driver may then be used to drive the anchor into a position in the bone.

Figure 46A:
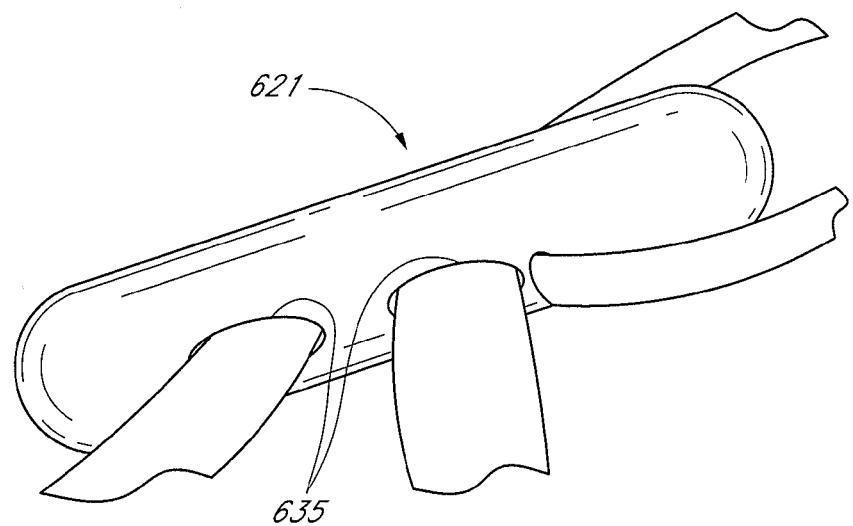
FIG. 46A shows a side view of an endobutton according to one embodiment
Figure 46B:
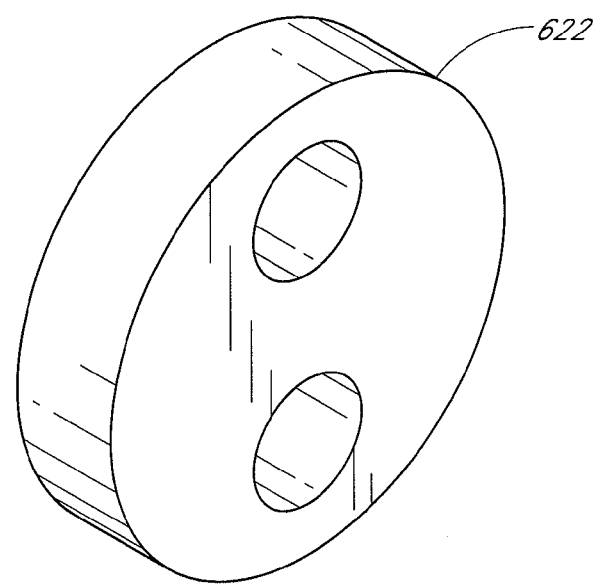
FIG. 46B shows a front view of an alternative embodiment of an endobutton according to one embodiment.

FIG. 46 illustrates one embodiment of an endobutton 621 having holes 635. In an embodiment utilizing sutures as the stabilizing implant, one or more sutures connected to suturing anchors may be threaded through holes 635 of the endobutton. The endobutton 621 may then be advanced into contact with a spinous process of a vertebrae. The sutures may then be knotted to each other or the endobutton 621, resulting in tension in the sutures to limit axial torsion. In one embodiment, the endobutton 621 and sutures may be used to attach various types of soft tissue to the spinous process, including allograft, autograft, or xenograft tissue.

To facilitate torsional stability between adjacent vertebrae, one or more instruments may be used. In some embodiments, a multi-functional instrument such as any one of shown in FIGS. 29-32D can be used to attach one or more implants between adjacent vertebrae.

Methods are described below using a multi-functional instrument and a stabilizing implant utilizing sutures according to one embodiment. While the methods described are applied unilaterally to a single side of the spine, in other embodiments, a method of stabilization is applied bilaterally. Whether a stabilizing implant is applied unilaterally or bilaterally may depend on the treatment desired and the location of the treatment area of the patient. For example, for herniated nucleus pulposus (slipped disk) patients who have a tear in the annulus that detrimentally permits nucleus material to escape from the disc space, a unilateral system may be used to augment muscle that may be weakened only on the side of the herniation. For other types of patients seeking different treatments, a bilateral system may be more appropriate.

One of skill in the art will appreciate that the methods described below using an implant comprising sutures are only a few of many methods in which a multi-functional instrument may be used to resist axial torsion. While the methods described use sutures in tension to provide torsional stabilization, one of skill in the art will appreciate that sutures are not mandatory, and other implants with or without sutures may also be used with the multi-functional instrument. Moreover, those skilled in the art will appreciate that the steps need not be performed in the exact order as described and may be performed in various orders to achieve similar results.

Figure 47A:
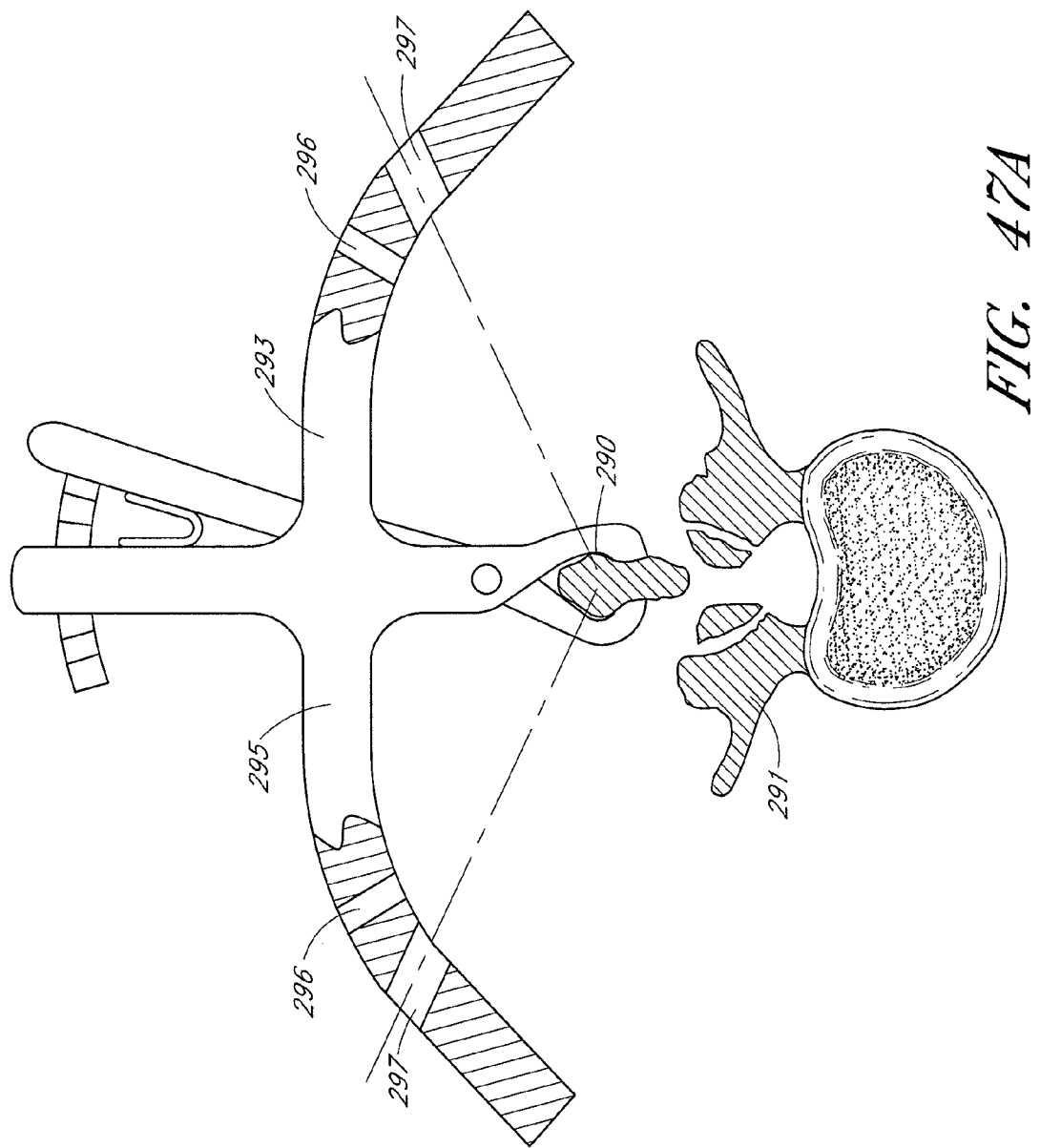
Figure 47B:
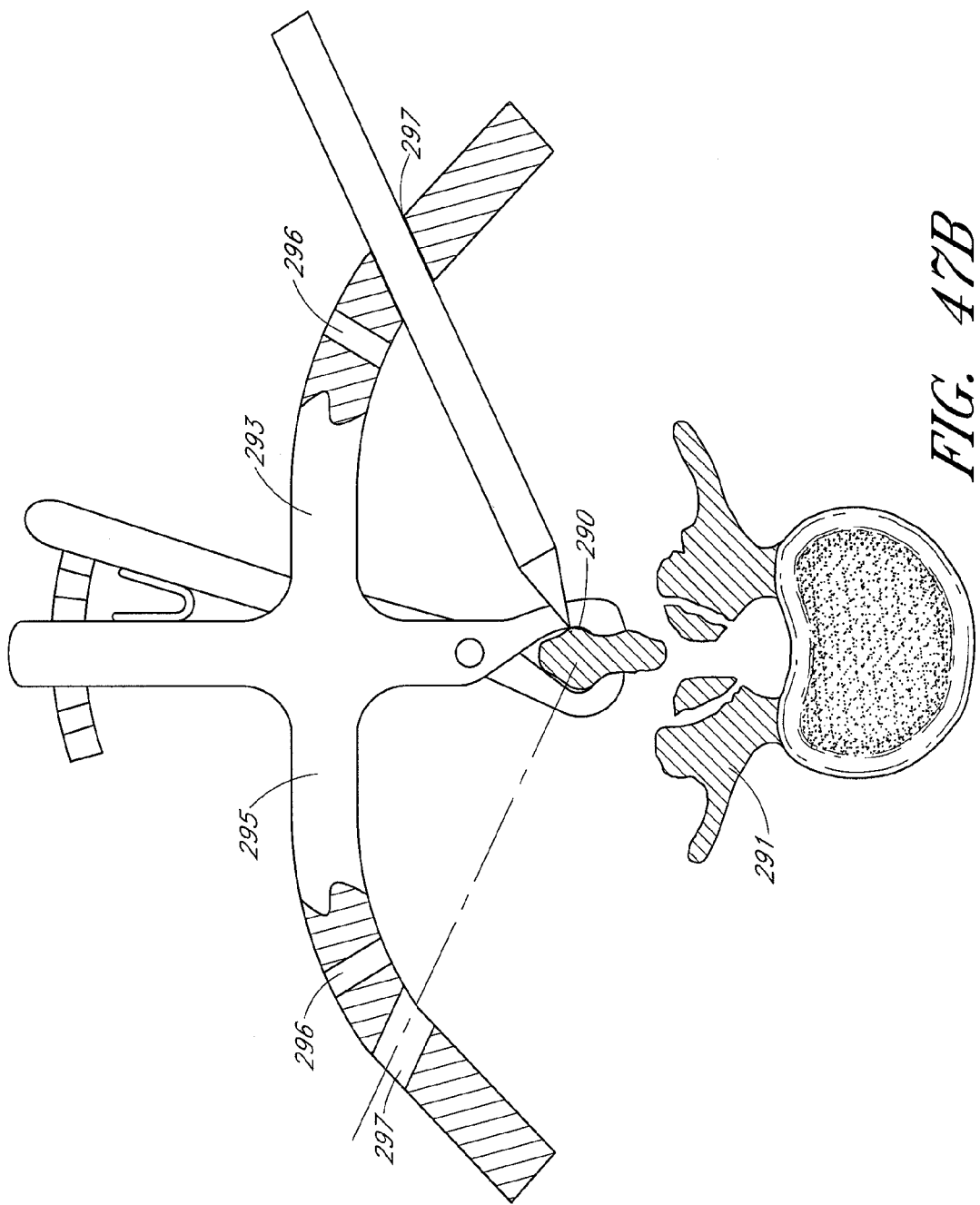
Figure 47D:
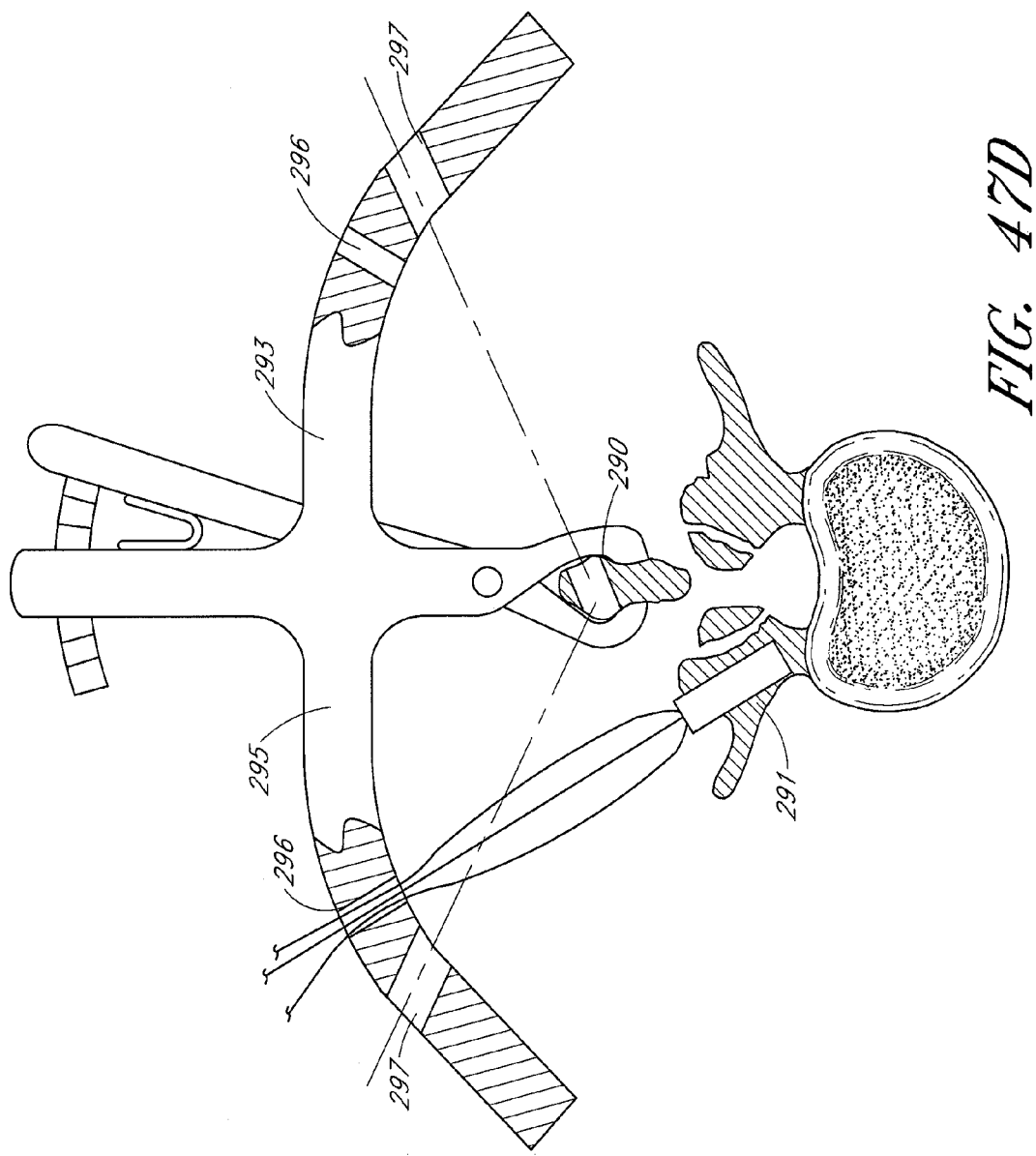
Figure 47E:
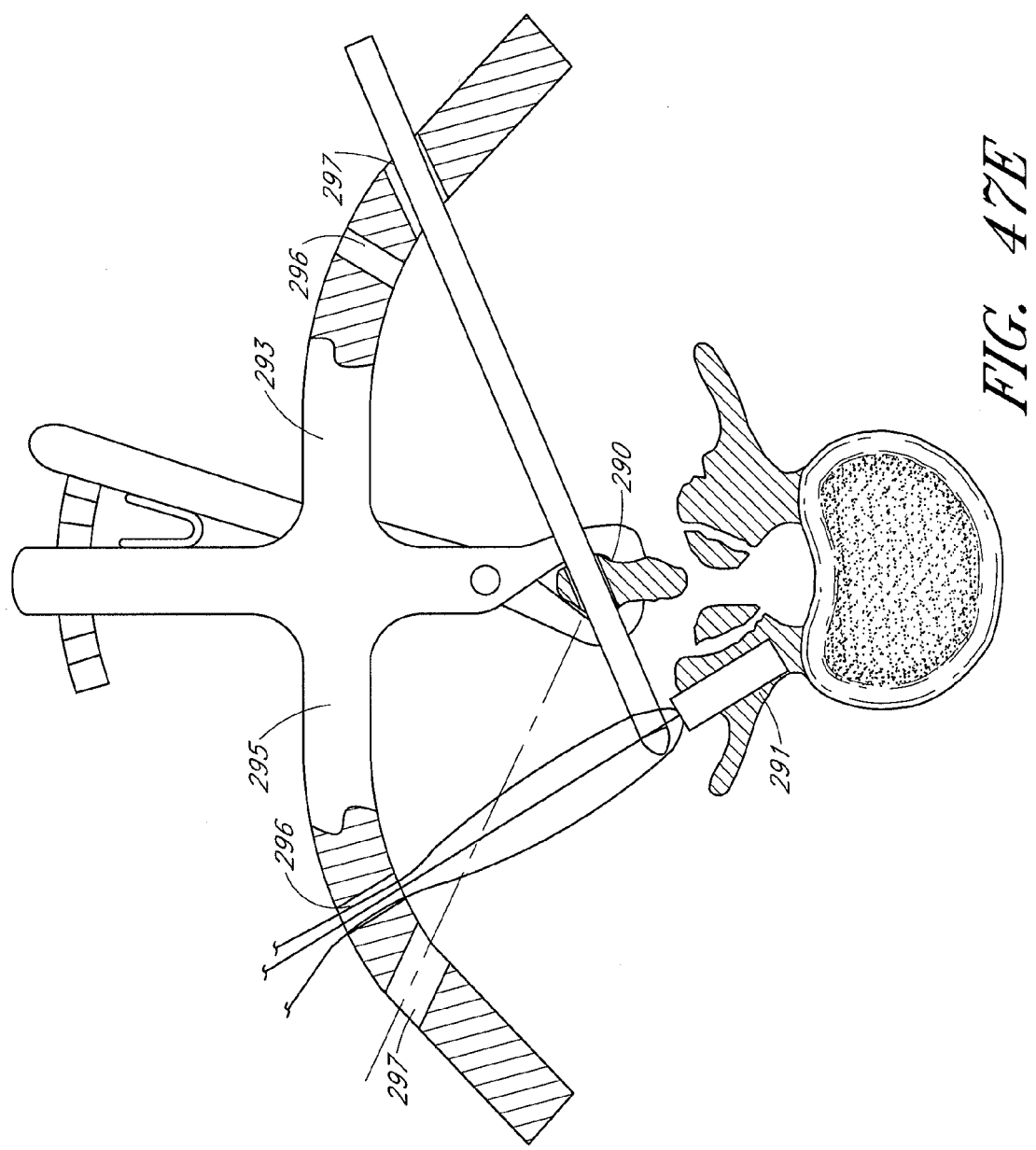

A method using the multi-functional instrument 300 of FIG. 29 will now be described with accompanying illustrations in FIGS. 47A-47J:

1. A clamping mechanism of instrument 300 is used to clamp to the spinous process 290 of a superior vertebral body as shown in FIG. 47A. The clamping mechanism may access the spinous process through an incision made over the spinous process. With the clamping mechanism clamped to the spinous process 290, the arms 293, 295 of the instrument 300 will be positioned over the skin of the patient.
2. Using hole 297 of the instrument 300 as a guide, a guide drill may be guided to create a hole in the spinous process 290 of the superior vertebral body as shown in FIG. 47B.
3. After creating a hole in the spinous process 290, a fixation device and suture implant can be guided using hole 296 to a location 291 of an inferior vertebral body as shown in FIG. 47C. In the illustrated embodiment the location 291 is the pedicle. The fixation device and suture implant can then be attached to a location 291 on the inferior vertebral body as shown in FIG. 47D.
4. After fixing the fixation device and implant to the inferior vertebral body at 291, a pulling instrument (such as a grabber, hooker or puller) can be passed through the hole 297 of the multi-functional instrument, and through the hole created in the spinous process 290, as shown in FIG. 47E. In other embodiments, the grabber, puller or hooker need not go through the hole in the spinous process, but rather, can go below or along side of the spinous process to pull an implant.

Figure 47G:
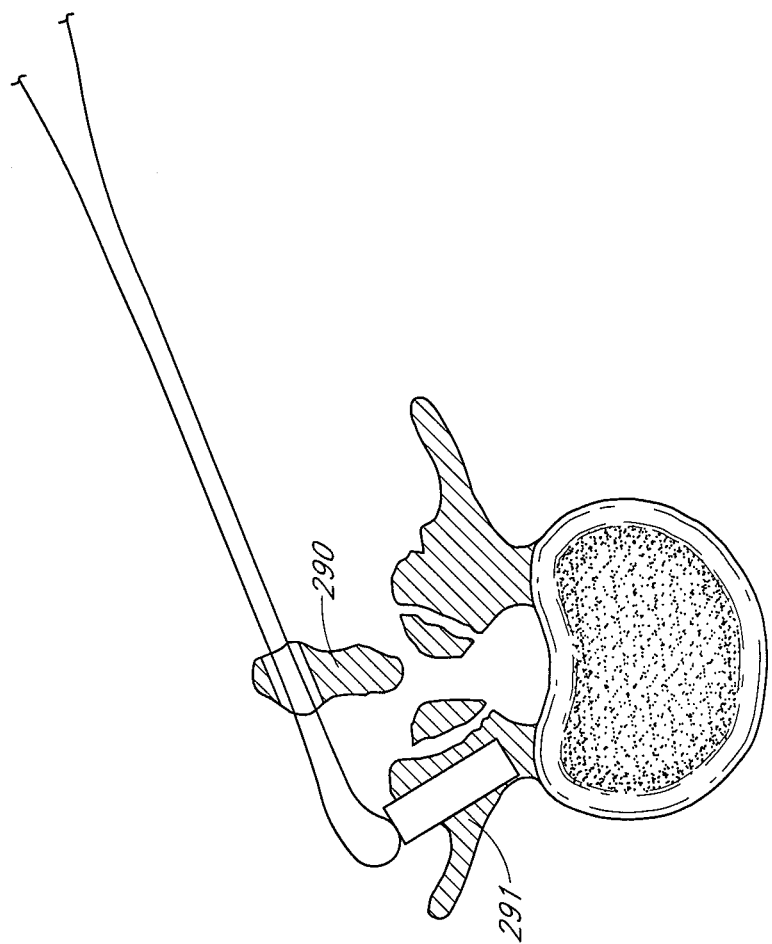
Figure 47H:
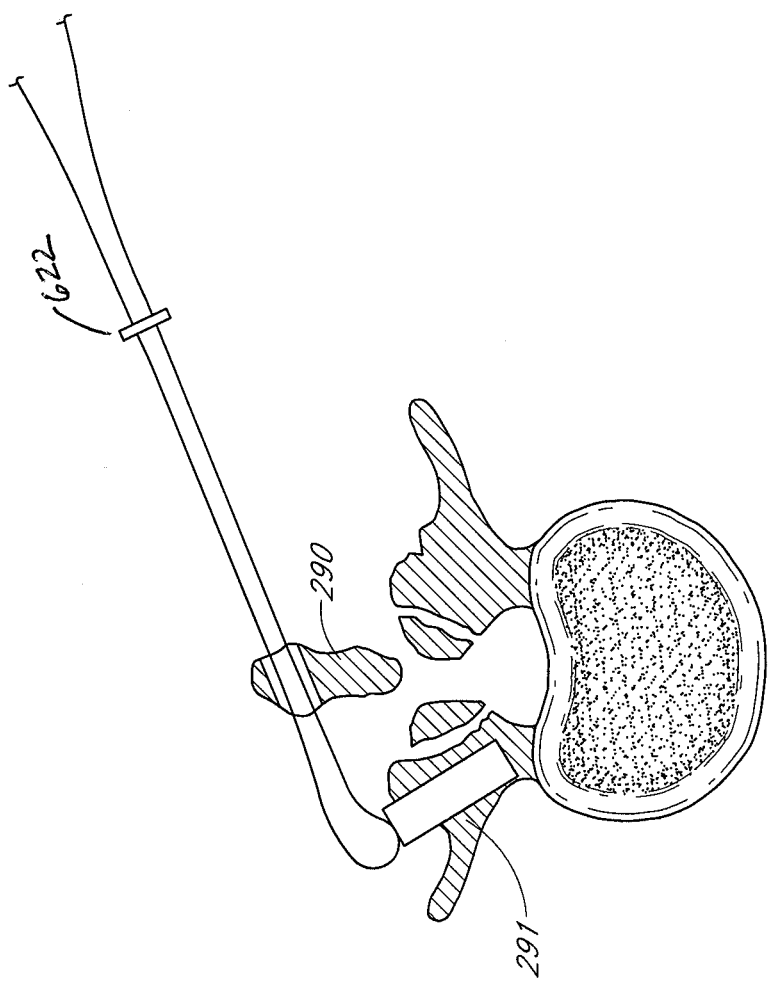
Figure 47J:
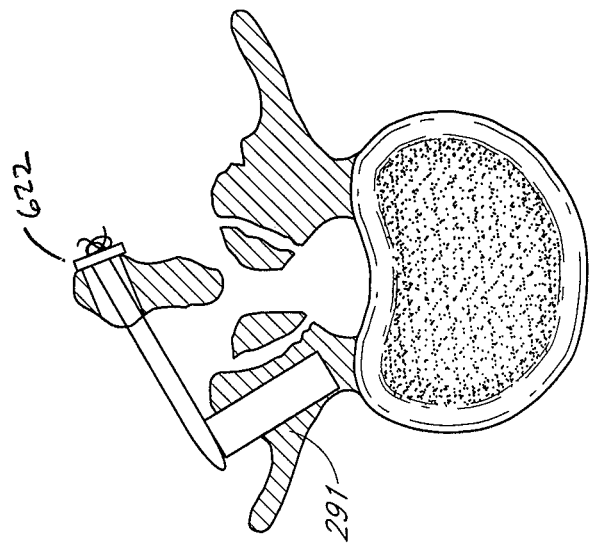
Figure 47I:
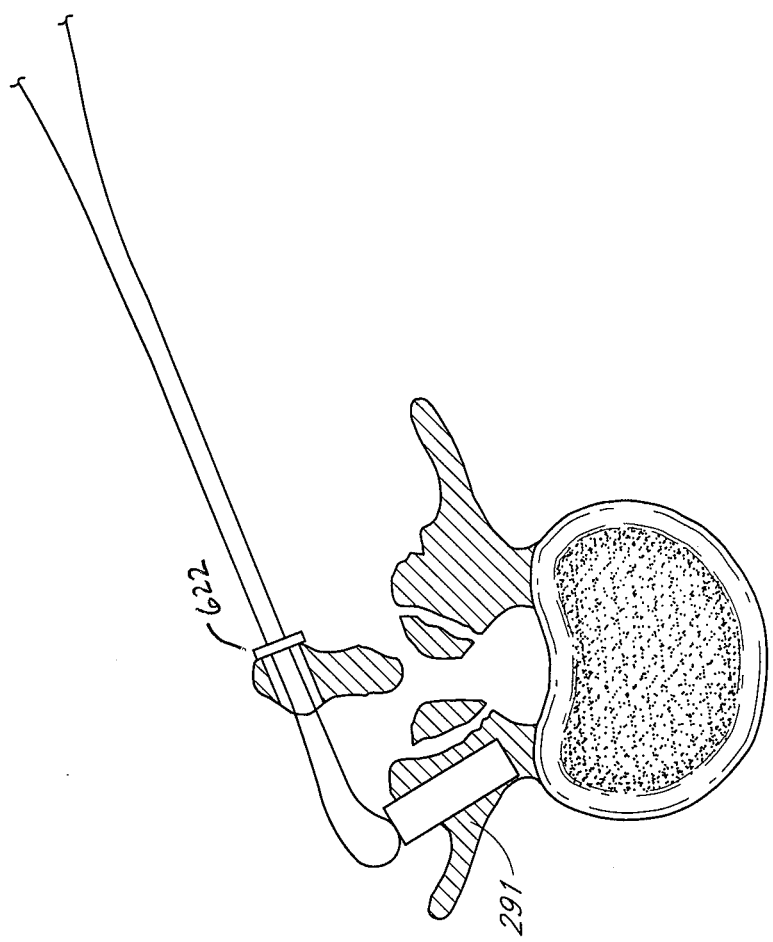

5. The pulling instrument can be used to pull the suture implant through the hole in the spinous process 290 as shown in FIG. 47F.
6. Once the suture implant has been pulled through the hole in the spinous process, the clamping instrument may be removed, leaving the suture implant fixed at a location 291 of the inferior vertebral body and through the spinous process 290 as shown in FIG. 47G.
7. An endobutton 622 (such as that shown in FIG. 46B) can then be provided. The suture implant can then be threaded through the holes of the endobutton 622 as shown in FIG. 47H.
8. The endobutton 622 and thread can then be advanced down the implant until the endobutton 622 is in contact with the side of the spinous process as shown in FIG. 47I.
9. After advancing the endobutton 622 to the spinous process, the implant may be placed in tension and a tie knot may be made using the two ends of the suture implant as shown in FIG. 47J. One method of placing the suture implant in tension is by applying a tensioner, which is commonly used in sports medicine applications. In other embodiments, hand tension can also be used to snug the knot against the endobutton 622.

As a result of the method above, torsional stabilization is provided in a unilateral manner using a suture implant and endobutton. In other embodiments, torsional stabilization may be applied bilaterally by applying the same method to the opposite side of the spinous process.

An alternative method using the multi-functional instrument 708 of FIG. 32A is described below. The steps described below may also be implemented with the methods previously described.

1. A patient is positioned so that the anterior-posterior axis of a targeted disc space is oriented vertically. This alignment is optional; however, in some patients, it may be much easier to perform a surgery according to this alignment.
2. An incision is made over the spinous process of the superior vertebral body. The depth of the incision will vary depending on the area of the body to be treated.
3. The instrument 708 may then be used to attach to the spinous process by using a clamping mechanism. In one embodiment, tines 715 may be used to clamp on the sides of the spinous process. Alternatively, a bone clamp may be used that serves as a combination clamp and bone punch such that a hole may be created in the spinous process.
4. The instrument 708 may then be held in a vertical position, matching the anterior-posterior axis of the disc space.
5. A skin incision may then be made using one of the anchor holes 732 as a guide. The anchor holes 732 are oriented to align with a series of locations that may be desirable locations for fixing one or more fixation devices, such as screws, staples or soft tissue anchors.
6. Through the skin incision, a needle, dilator or cannula as described above may be used to create a working channel from the incision to the desired location for fixing one or more fixation devices.
7. Using the cannula described above, a soft tissue anchor preloaded with one or more sutures as described herein may be implanted.
8. A drill or bone awl may be introduced through one of the passing holes 740 and may be used to create a hole in the spinous process adjacent to the tines 715.
9. A hooker, grabber or puller as described above may be inserted through the passing hole 740, through the created hole in the spinous process and across to the cannula containing the soft tissue anchor.
10. The cannula and inserter may then be retracted.
11. The hooker, grabber or puller may then be advanced to capture the sutures. In one embodiment, the sutures may be tensioned to enhance capture.
12. The hooker, grabber or puller, along with the captured sutures, may then be retracted through the created hole in the spinous process and out of the patient's body completely along with the sutures.
13. The instrument 708 may then be removed.
14. The sutures may then be threaded through holes in an endobutton, such as described above, and the endobutton advanced in contact with the spinous process.
15. Knots may then be used to tighten the sutures to the endobutton, resulting in adequate tension in the sutures to limit axial torsion. In a preferred embodiment, two ends of a single suture are used as the stabilizing implant and are tied to each other after passing through separate holes in an endobutton. Although in one embodiment, axial torsion is limited in a single direction, it may be possible to limit axial torsion in multiple directions using sutures of different orientation.
16. The incisions may then be closed in a normal fashion.

Soft Tissue Graft and Fabric Implants

Various stabilizing implants may be used as described above. In one embodiment, the stabilizing implants may be comprised of soft tissue grafts, including autograft, allograft, xenograft or combinations thereof. Examples of tissue to be used includes fascia latae, semitendonosis and gracilis tendons, hamstring tendon, patellar tendon, quadriceps tendon, Achilles tendon, small intestine submucosa (SIS) and skin, including processed xenografts such as the Zimmer® Collagen Repair Patch and DePuy® Restore Biologic Implant. In an alternative embodiment, the implants may be comprised of one or more fabrics. These implants may be placed proximate to various locations along the spine, and may be fixed into position by using screws, staples, anchors or other fixation devices as described herein. Depending on the fixation device, one or more sutures may be attached to one end of the fixation device (such as a screw or staple) to maintain an implant in tension.

Numerous methods exist that allow one skilled in the art to position one or more implants between different locations of the same vertebrae or in between different locations of adjacent vertebrae. In one embodiment, a stabilizing implant may be pre-assembled to a fixation device, such as an anchor, before being used in a surgery. The term "pre-assembled" refers to an implant that has been assembled to a fixation device before the implant is placed into actual use, and pre-assembly can take place, for example, on a back table in the operating suite or in an outside facility.

Figure 50:
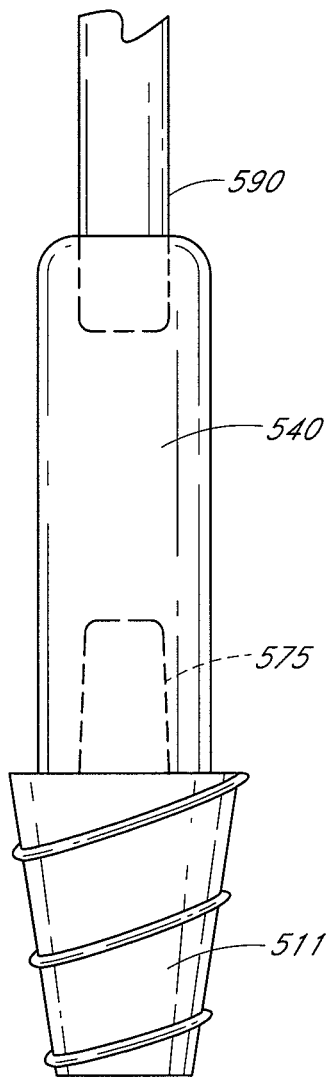
FIG. 50 shows an anchor assembled to a stabilizing implant with sutures according to one embodiment.

FIG. 50 illustrates one embodiment in which a suture anchor 511 with one or more sutures 575 is attached to one end of an implant 540, while one or more sutures 590 are attached to an opposite end of the implant 540. In a preferred embodiment, the implant comprises a soft tissue graft or a fabric. In one embodiment, and with reference to FIG. 50, a method of fixation is provided in which a suture anchor 511 is pre-assembled to one end of a stabilizing implant 540 before the stabilizing implant 540 is inserted into the body of the patient. One or more sutures 575 of the suture anchor 511 are used to sew, knot and/or tie the suture anchor 511 to the stabilizing implant 540 prior to insertion into the patient. Besides the sutures 575 of the suture anchor 511, one or more additional sutures 590 may be pre-attached to the opposite end of the stabilizing implant 540. When the suture anchor 511 having sutures 575 attached to one end of the stabilizing implant 540 is inserted into a desired location in the bone, in one embodiment, the sutures 590 at the opposite end of the implant 540 may be placed in tension, for example, by hooking, grabbing or pulling the sutures 590. These sutures 590 may be used to help maintain tension in the implant while the sutures are themselves maintained in tension, for example, when a hooker, grabber or puller is used to capture the sutures 590. Alternatively, the implant may be placed in tension when a hooker, grabber or puller is used to capture the stabilizing implant 540. In yet another embodiment, the sutures 590 that are used to maintain tension in the implant may also be used to fix the implant to an endobutton 621 as shown in FIG. 46.

Figure 51:
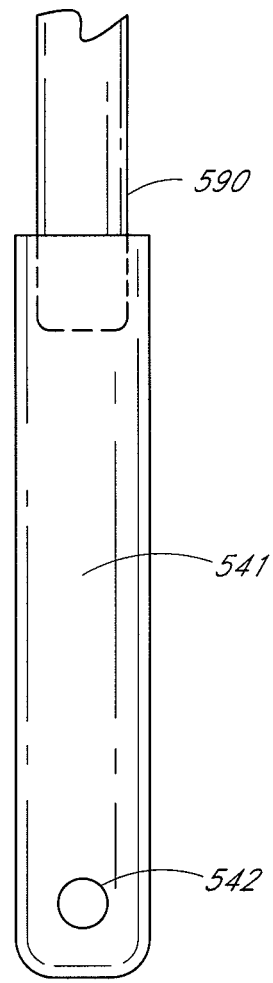
FIG. 51 shows a stabilizing implant with a hole assembled with sutures according to one embodiment.

In accordance with systems, methods and apparatuses of another embodiment, a hole 542 may be created in a stabilizing implant 541, such as a fabric or soft tissue graft, to pass a headed screw through the hole as shown in FIG. 51. The head of the screw may be used to hold the stabilizing implant down to the bone. In one embodiment in which the implant is a fabric, a hole may be used with or without reinforcement. The term "reinforcement" is used to describe using a metal or polymeric grommet, or using sewing, knitting or embroidery techniques to increase the thread density in the area surrounding the hole. In an alternative embodiment in which the implant is a soft tissue graft, a hole may be created by looping the graft back on itself and suturing across one or more legs of the graft. At the end opposite the hole, one or more sutures 590 may be provided to maintain an implant in tension as described above. In another embodiment, the sutures 590 that are used to maintain tension in the implant may also be used to fix the implant to an endobutton 621 as shown in FIG. 46.

Measuring Devices and Methods

Methods and apparatuses are described that relate to measuring a stabilizing implant, such as a soft tissue graft or fabric. In one embodiment, the stabilizing implant may be measured and in some cases, modified, after being inserted into the body. In a preferred embodiment, the stabilizing implant will be measured to be an appropriate length before insertion into the body. Techniques for measuring the stabilizing implants can be incorporated into any of the methods described herein.

In one embodiment, the sizing of an implant may be based on the instruments used to insert the implants. Under this approach, the size of the implants may be based on the dimensions of the instrument that is used. In one embodiment, for example, in which a multi-functional instrument as shown in FIG. 32A is used to position implants for torsional stabilization, the position and orientation of the anchor hole 732 relative to the tines 715 and the passing hole 740 generally specify the length of the stabilizing implant. Once the instrument is selected (for example, based on the location of the spinous process and the anchor holes), in one embodiment, the stabilizing implant may be selected from a group of implants sized to match the selected instrument appropriately. Under this approach, one or more multi-functional instruments may be provided to cover the variations in size expected in the patient population.

In another embodiment, one skilled in the art may use a measuring instrument 802 as shown in two different views in FIGS. 48A and 48B. FIG. 48A illustrates a side view of a measuring instrument assembly 802 comprised of a measurement instrument frame 822 and a measurement filament 830. FIG. 48B illustrates a front view of the measurement instrument assembly 802, in which the measurement instrument includes a cut out portion 850 that allows a hooker, grabber or puller to capture the measurement filament 830 when the instrument is assembled and in use.

Figure 49A:
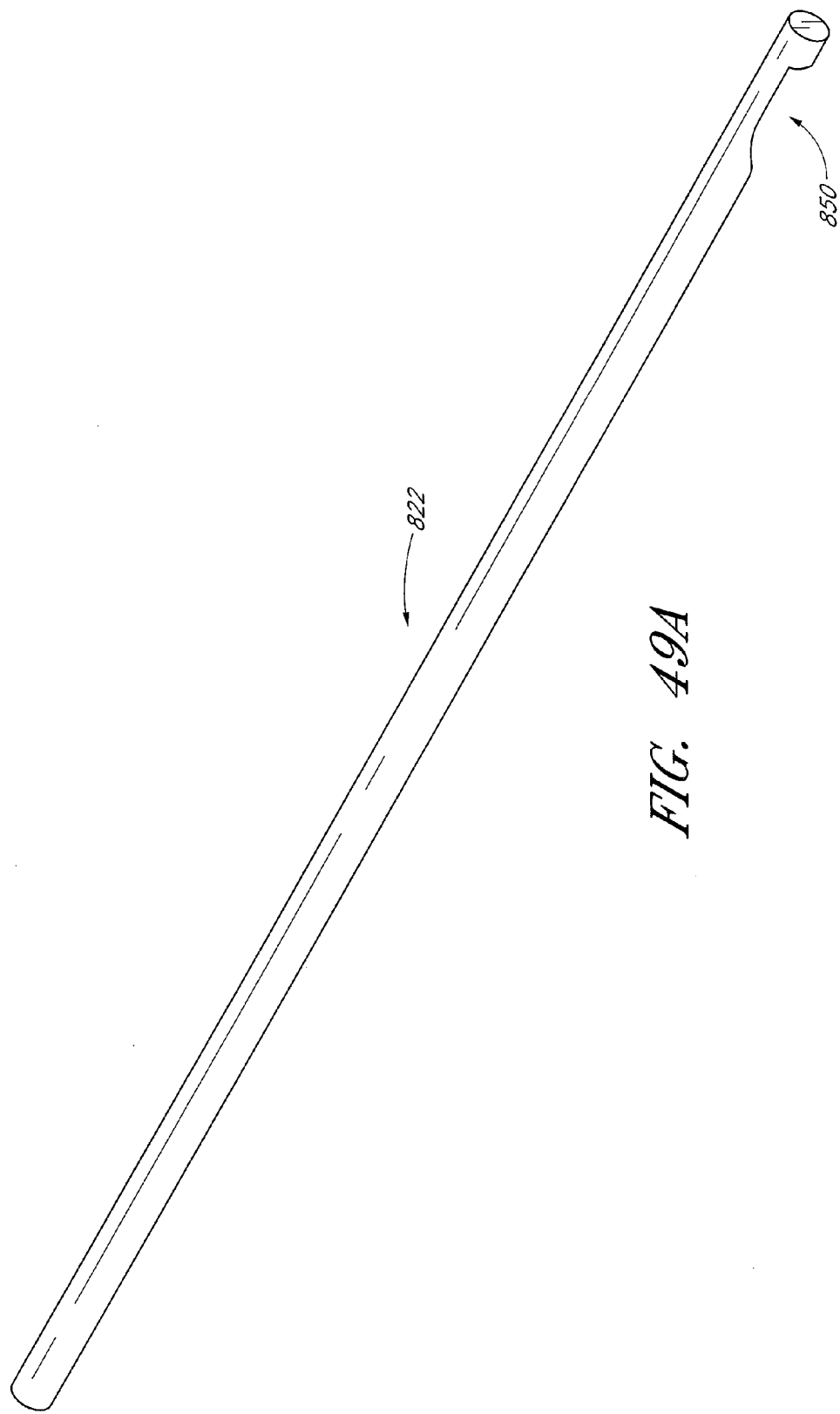
FIG. 49A shows a measurement instrument frame according to one embodiment.

FIG. 49A illustrates one embodiment of the measurement instrument frame 822 according to one embodiment. With respect to an assembly 802 having two components, the frame 822 and the filament 830, the frame 822 may be the stationary portion. The frame may have a cut out portion 850 that permits a hooker, grabber or puller from capturing a filament 830 located in the frame 822. Moreover, in another embodiment, the frame may include a post that spans the inner diameter of the frame. The post provides a means for attachment of the filament.

Figure 49B:
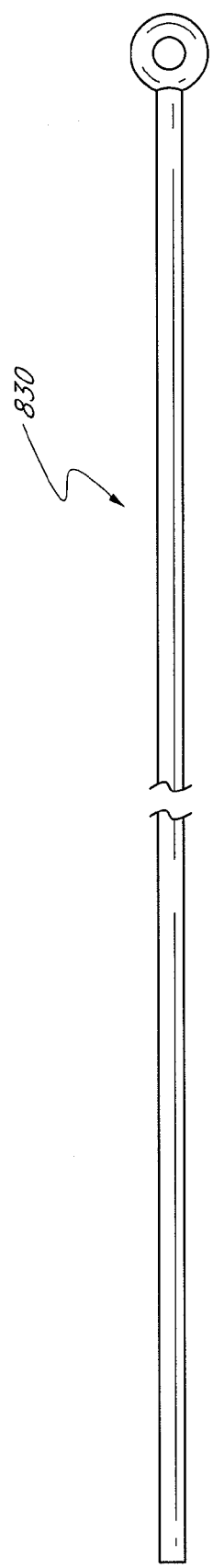
FIG. 49B shows a measuring filament according to one embodiment.

FIG. 49B illustrates one embodiment of a measuring filament 830 according to one embodiment. The filament 830 may be comprised of a suture, wire, cable or other flexible material. In some embodiments, the filament 830 is comprised of a biocompatible polymer or metal. In a preferred embodiment, the filament is comprised of a flexible material capable of being placed in tension in order to provide a proper measurement of a suitable implant.

In one embodiment, and as shown in FIG. 49B, the filament 830 may be an unmarked suture, wire, cable or other flexible material. In some embodiments, the filament may include a series of marked parallel lines that extend around the shape of the filament. The lines could be created by printing, engraving, laser marking or etching. Such lines may correspond with length, and would aid in the proper measuring of an implant. In some embodiments, it is possible that the filament include a series of grooves or indentations, which may also serve to assist in proper measuring of an implant. In one embodiment, the filament 830 is read within the body, such as through an opening in the patient's body, with or without an instrument. For example, one may be able to view a filament that is marked with actual numbers while the filament is in use within a patient's body without using any additional instruments. Alternatively, one may view the filament 830 after it is removed from a patient's body, for example, by using a chemical compound such as methylene blue with the filament to indicate areas in which the measurement instrument was placed in the body. Besides these methods, other methods of reading the measurement filament 830 may also be employed, and one skilled in the art will not be limited to any particular technique.

The frame 822 and filament 830 may assume a number of shapes. In one embodiment, the filament has one end shaped like a toroid (as shown in FIG. 49B) to allow for rotational movement of the filament about the post within the frame. This rotational movement may be important when the filament 830 is assembled into the frame 822, as the rotation may be important for measuring the length of the stabilizing implant and it is expected that an implant may rotate similarly when tensioned.

In some embodiments, filament 830 may be suitable for permanent use with a frame 822, and thus may be suitable for reuse. Under these embodiments, the filament 830 may be marked, either by writing or indentation, so that it could be reused multiple times. In other embodiments, the filament 830 may be made completely disposable, which would allow the filament 830 to be cut as desired to assist in measuring an implant. The cut filament 830, once removed from a patient, may be measured using a standard measuring means such as a ruler to assist in finding an implant of appropriate size. In an alternative embodiment, a measurement assembly 802 can be designed such that a frame 822 is reusable.

A method is now provided for using the multi-functional instrument 708 in FIG. 32A and the measuring instrument 802 having a measuring filament 830 and measuring frame 850 shown in FIGS. 48A and 48B to measure and install an implant. One of skill in the art will appreciate that the method described is only one of many methods in which the measuring instrument assembly 802 can be used to measure an implant. Moreover, those skilled in the art will appreciate that the steps need not be performed in the exact order as described, and therefore, may be performed in various orders to achieve similar results.

The method is described as follows:

1. A patient is positioned so that the anterior-posterior axis of a targeted disc space is oriented vertically. This alignment is optional; however, in some patients, it may be much easier to perform a surgery according to this alignment.
2. An incision is made over the spinous process of the superior vertebral body. The depth of the incision will vary depending on the area of the body to be treated.
3. A multifunctional instrument 708 may then be used to attach to the spinous process by using a clamping mechanism. In one embodiment, tines 715 may be used to clamp on the sides of the spinous process. Alternatively, a bone clamp may be used that serves as a combination clamp and bone punch such that a hole may be created in the spinous process.
4. The instrument 708 may then be held in a vertical position, matching the anterior-posterior axis of the disc space.
5. A skin incision may then be made using one of the anchor holes 732 as a guide. The anchor holes 732 are oriented to align with a series of locations that may be desirable locations for fixing one or more fixation devices, such as screws, staples or soft tissue anchors.
6. Through the skin incision, a needle, dilator or cannula as described above may be used to create a working channel from the incision to the desired location for fixing one or more fixation devices.
7. A drill or bone awl may be introduced through one of the passing holes 740 and may be used to create a hole in the spinous process adjacent to the tines 715.
8. A measuring instrument 802 with measurement filament 830 may then be inserted into the cannula and held to the bone.
9. A hooker, grabber or puller is inserted through the passing hole 740, through the created hole in the spinous process, and across to the cannula containing the measuring instrument 802.
10. The cannula may then be partially retracted.
11. The hooker, grabber or puller may then be advanced to capture the measurement filament.
12. The hooker, grabber or puller (with the captured measurement filament) may then be retracted through the created hole in the spinous process, and out of the patient's body along with the measurement filament 830.
13. The measurement filament 830 may be tensioned and read or cut to length for measurement outside of the patient's body.
14. The measuring instrument 802 (including filament 830) may then be removed.
15. A stabilizing implant of an appropriate length may then be selected from a plurality of implants based on the measurement provided by the measuring instrument 802. In an alternative embodiment, if an implant of appropriate size is not available, a stabilizing implant of an appropriate length may be prepared.
16. The dilator and cannula may then be reinserted through the anchor hole and advanced to the targeted position. The dilator may then be removed.
17. The stabilizing implant and inserter may then be inserted through the cannula and fixed to the lower vertebral body.
18. A hooker, grabber or puller may then be inserted through the passing hole, through the drilled hole in the spinous process, and across to the cannula containing the stabilizing implant.
19. The cannula and inserter may then be retracted.
20. The hooker, grabber or puller may then be advanced to capture the stabilizing implant and associated sutures.
21. The hooker, grabber or puller (with the captured sutures) may then be retracted through the created hole in the spinous process, and out of the patient's body along with the sutures.
22. The instrument 708 may then be removed.
23. One or more sutures may then be threaded through holes in an endobutton 621 and the endobutton 621 may be advanced into contact with the spinous process.
24. One or more knots may be used to tighten the sutures to the endobutton 621, resulting in adequate tension in the sutures to limit axial torsion in one or more directions. In a preferred embodiment, two ends of a single suture 590 are tied to each other after passing through separate holes in an endobutton.
25. Incisions are closed in the normal fashion.

Suture Anchor and Suture Plug

With the advent of stronger and more durable suture materials, there is the potential to have sutures function mechanically for a long period of time. One current limitation of suture longevity is the connection between the suture and its associated hardware, such as soft tissue anchors. A publication by Bardana et al. entitled "The Effect of Suture Anchor Design and Orientation on Suture Abrasion: An In Vitro Study," Arthroscopy, 2003, 19(3), 274-281, highlights some concerns. In the article, the authors found that the eyelet geometry and surface finish of the suture anchors had a significant effect on suture abrasion. Abrasion of the suture was also impacted by the direction of pull on the suture.

An improved suture anchor and associated devices, such as suture plugs, that result in reduced (minimal to zero) abrasion on sutures to prevent the repeated replacement of sutures used in patients is desired. Embodiments of improved suture anchors and suture plugs are described below. The suture anchor and suture plug may be used on their own, in combination or in addition to the systems, methods and apparatuses described herein for providing torsional stabilization.

This application describes novel suture anchors that will reduce abrasion associated with motion between the suture anchor and suture and thereby enhance the mechanical longevity of the suture assembly. The design of the improved suture anchor may have slight variations depending on the line of pull of the suture with respect to the long axis of the anchor. In this application, two embodiments are described, one in which a suture is at a generally 90 degree orientation with a long axis of an anchor (shown in FIG. 52) and another in which the line of pull of a suture is generally aligned with the long axis of the anchor (shown in FIG. 59). A novel suture plug that can be fixed into the spinous process of a spinal vertebral body is also described. In addition, systems, methods and apparatuses related to surgical instruments that allow for proper alignment between the suture anchor, the suture plug and the spinous process are also provided.

Figure 52:
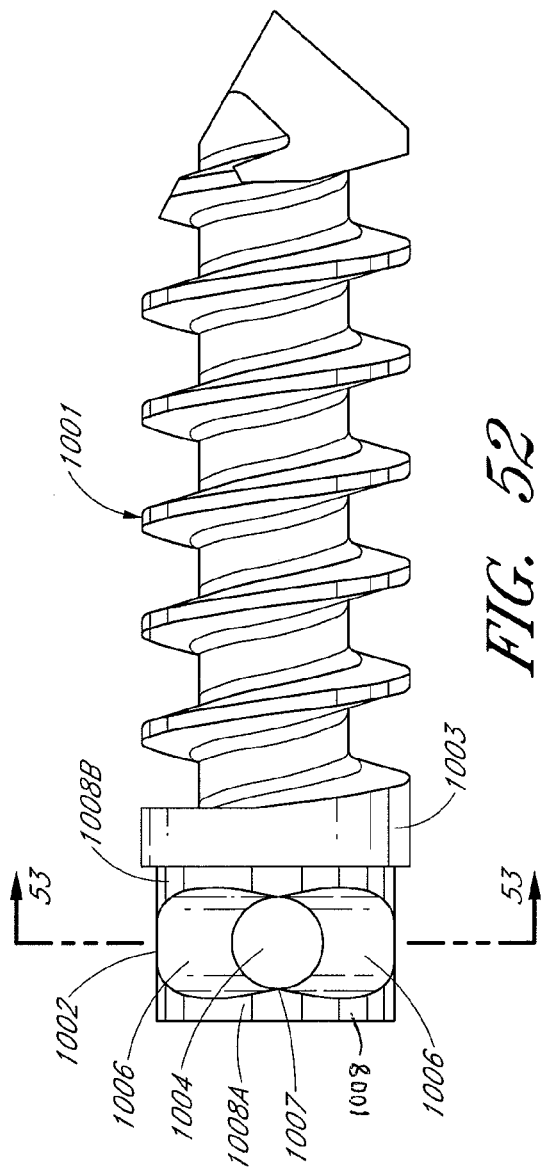
FIG. 52 is a side view of a suture anchor according to one embodiment.
Figure 54:
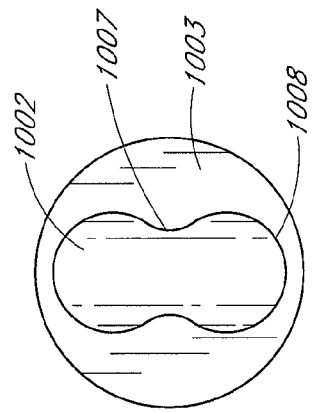
FIG. 54 is a top view of the suture anchor and collar of FIG. 52.

FIG. 52 shows a side view of one embodiment of a suture anchor for use with a suture that is to be pulled along a line generally 90 degrees to the long axis of the anchor. According to the embodiment, one or more sutures may be pulled transversely to the long axis of the anchor. The suture anchor 1002 has a standard means for attaching to bone, in this case, a self-tapping thread 1001. The head of the suture anchor 1002 is separated from the thread by a collar 1003 which may be cylindrical in shape, or may have any other suitable shape. The head 1008 of the suture anchor extends above the collar 1003, and within the head 1008 of the suture anchor is an eyelet hole 1004 defining an opening extending transversely to the long axis of the anchor. When viewed from above as shown in FIG. 54, the head 1008 of the anchor may in one embodiment have generally a figure-eight shape.

Figure 53:
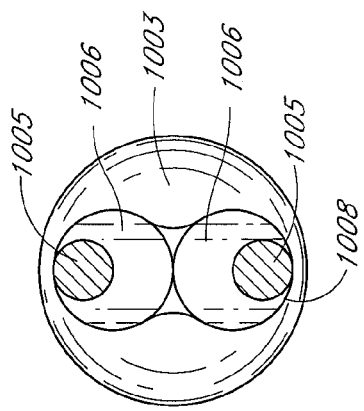
FIG. 53 is a cross-sectional top view of the suture anchor of FIG. 52.

In addition to these features, the suture anchor provides an anchor head 1008 having a novel geometry that mitigates abrasion to a suture when in use. In the illustrated embodiment, the eyelet hole 1004 transitions smoothly into and is defined between two posts 1005 shown in FIG. 53. FIG. 53 illustrates the transverse cross-section of the head of the suture anchor at the center of the eyelet as measured along long axis of the anchor, wherein the eyelet diameter is at its largest. The posts 1005 at this central eyelet location in one embodiment each has a round cross-section, and when extending away from the central eyelet location along the long axis of the anchor, either toward the thread 1001 or toward the top of the head of the anchor, each of the rounded posts gradually increase in diameter. As the diameter of the rounded posts increases in diameter both toward the top and bottom ends of the anchor, the center points defining the diameter of the posts moves gradually away from the outer edge of the head of the anchor toward the other post. Eventually, at the top and bottom of the head of the anchor, the two posts merge together, thereby closing off the eyelet.

The outer surfaces of the posts 1005 as they vary in diameter adjacent to the eyelet may be considered to be lofted surfaces 1006, which may also be seen as one side of each of the posts 1005. One or more sutures are capable of being pulled in tension while resting on the lofted surfaces 1006 with minimal risk of abrasion. The head 1008 of the suture anchor 1002 also provides indentations 1007, as best seen in FIG. 54, which assist in the placement of one or more sutures in the head of the suture anchor via use of an inserter as described below. As shown in FIG. 52, the head 1008 of the suture anchor also comprises a top surface 1008A and base surface 1008B of the anchor head that enclose the eyelet hole 1004 from top and bottom, with the base surface 1008B being the portion that rests on collar 1003. These surfaces of anchor head 1008 may be considered to be the portions where the posts 1005 merge as described above. The surface of the suture head also helps to contain the sutures in the track created by the surface. Depending on the size of the eyelet, the suture anchor shown in FIG. 52 may contain and receive one suture or multiple sutures, such as two, three, four, five or more.

In one embodiment, one or more sutures may pass through the eyelet 1004 such that when tensioned, the sutures pull around one or more posts 1005. In the illustrated embodiment, the cross-section of the post 1005 is circular (as shown in FIG. 53), while in other embodiments, the cross-section may be elliptical, oval or other generally round geometries. There are no sharp edges that can abrade the sutures when the suture slides relative to the post through the eyelet. Lofted surfaces 1006, seen in FIG. 52, may help to ensure that there is a smooth transition between the eyelet 1004 and the edge of the head. In some embodiments, these "lofted" surfaces refer to smooth, rounded surfaces that form one side of the post 1005 and form the material between the eyelet hole 1004 and the edge of the head of the suture anchor 1002. In the illustrated embodiment, the lofted surfaces 1006 form a smooth surface from the base of the anchor head 1008 to the top of the post 1005. In one embodiment, the lofted surfaces 1006 form an arcuate seat or groove upon which one or more tensioned sutures may rest on and be cupped with minimal risk of abrasion. In some embodiments, the lofted surfaces 1006 may form two or more arcuate seats or grooves that allow multiple sutures in tension to be cupped with minimal risk of abrasion.

Figures 57, 58, 59:
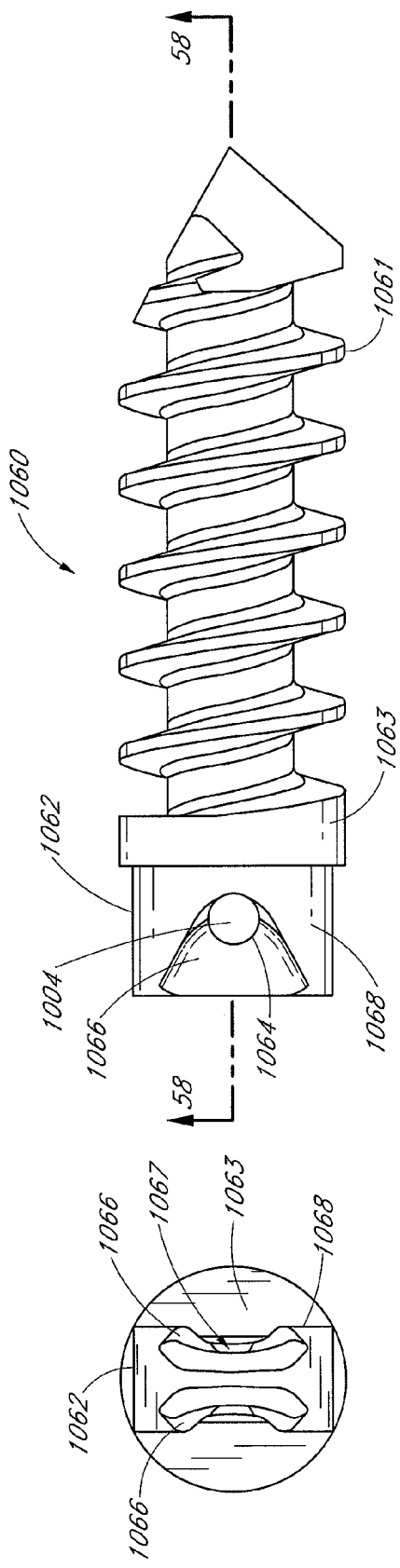
FIG. 57 is a side view of a suture anchor according to one embodiment.
FIG. 58 is a cross-sectional side view of the suture anchor of FIG. 57.
FIG. 59 is a top view of the suture anchor of FIG. 57.
Figure 62:
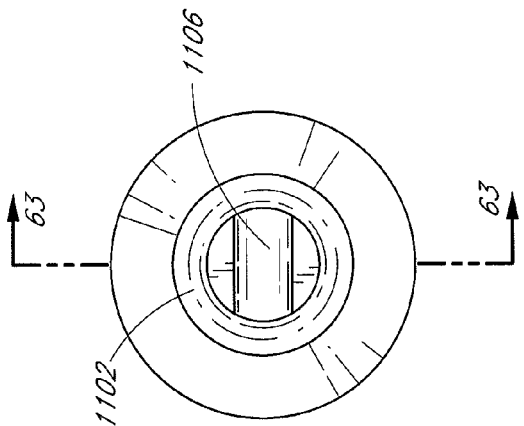
FIG. 62 is a bottom view of the suture anchor of FIG. 60.
Figure 61:
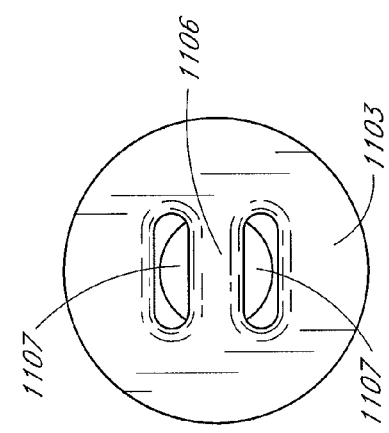
FIG. 61 is a top view of the suture anchor of FIG. 60.
Figure 63:
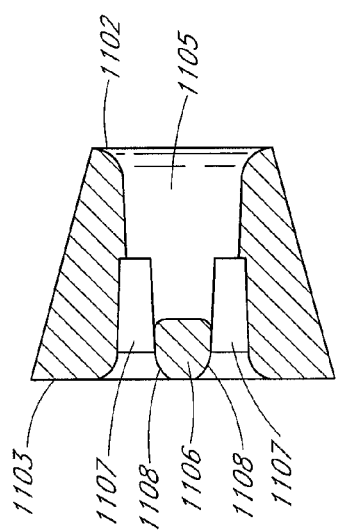
FIG. 63 is a cross-sectional view of the side of the suture plug of FIG. 60.

FIG. 53 shows a cross-sectional top view of the suture anchor of FIG. 52. FIG. 53 illustrates how the suture anchor head 1008 is shaped similar to a figure eight. While the suture anchor head 1008 is shaped like a figure eight for purposes of this embodiment, one skilled in the art will appreciate that the suture anchor head may be of other shapes including a rectangle (as shown in FIG. 59). The shape of the surfaces can be designed to mate with a portion of an inserter device as shown in FIG. 55. As shown in FIG. 53, the post 1005 is circular and formed by the contour of the lofted surfaces 1006. In this embodiment, the cross-section of the lofted surfaces 1006 form generally round surface areas from the base surface of the anchor head 1008 to the post 1005. In one embodiment, the area of the generally round surface areas decreases in size from the base surface of the anchor head 1008 to around the middle of the post 1005 and increase in size from around the middle of the post 1005 to the top surface of the anchor head 1008, to form a smooth arcuate seat or groove where one or more sutures in tension can be placed. While the illustrated embodiment shows the cross-section of the post 1005 and its lofted surfaces 1006 as being circular, the cross-section may vary in shape (e.g., they may be elliptical) so long as the lofted surfaces 1006 form a smooth, edgeless section that reduces the risk of suture abrasion.

FIG. 54 shows a top view of the suture anchor of FIG. 52. FIG. 54 illustrates geometrical portions 1008 for mating with the suture anchor inserter as described below and indentations 1007 which can be used to provide an opening for the one or more sutures to pass through when using a suture anchor inserter. Also shown in FIG. 54 is the top of the collar 1003, over which the suture anchor head rests.

In a preferred embodiment, the surfaces 1006 of the suture anchor head 1002 are produced to a high surface finish, such as would be appropriate for use on the metal articulation of total joint replacements (between 0.1 to 0.5 microns (Ra)). At the same time, the geometrical portion 1008 that mates with the inserter (seen in FIGS. 52 and 54), may be more roughly finished without impacting the articulation between the anchor and the suture.

FIGS. 55 and 56 illustrate a side view and cross-sectional view respectively of an anchor inserter 1041 according to one embodiment. The anchor inserter 1041 has an end 1042 which connects to a suture anchor, and a second end 1043 which can affix to a handle (not shown). A central hole 1051 penetrates through the inserter which allows one or more sutures to pass through while the inserter is connected to a suture anchor. In one embodiment, the anchor inserter 1041 has an oblong cavity 1052 designed to slidably mate with the top of the suture anchor at the anchor head 1008 at surfaces adjacent to the lofted surface 1006 of the suture anchor. In other embodiments, such as those that include suture anchor heads having different geometries, the anchor inserter may have a cavity of a different shape, such as rectangular. Indentations 1007 allow sutures loaded on the suture anchor to be torqued and extended through the cavity 1052 of the anchor inserter. This is because there is minimal to zero contact between the inserter 1041 and the anchor in the region of the indentations 1007, which permits the suture to be pulled within the central hole 1051 of the inserter 1041 while the inserter is being used to place the suture anchor loaded with the sutures in a certain location. In addition, the inserter and suture anchor contact are designed to avoid the surfaces 1006 of the suture anchor so as to avoid marring the surface.

An alternative embodiment of a suture anchor 1060 is shown in FIGS. 57-59, in which the line of pull of the suture is intended to be generally along the long axis of the suture anchor. The suture anchor 1060 has a means for attaching to bone, in this case, a self-tapping thread 1061. The head of the suture 1062 is separated from the thread by a collar 1063 as described above. Within the head of the suture anchor is an eyelet hole 1064 that extends transverse to the long axis of the anchor. In addition to these features, the suture anchor provides a suture head having a novel geometry that allows for reduced abrasion when in contact with one or more sutures. The eyelet hole 1064 transitions smoothly into a post 1065 (shown in FIG. 58) having one side with lofted surfaces 1066. Unlike the embodiment of FIG. 52, wherein the posts 1005 are located to the transverse sides of the eyelet 1004, in FIG. 59, the post 1065 is located above and toward the top of the eyelet 1064. One or more sutures can pass through the eyelet and when tensioned, can pull around the post 1065 and rest on or be cupped in portions of the lofted surfaces 1066 with minimal risk of abrasion. In one embodiment, the cross section of the post is circular, while in other embodiments it may be elliptical, oval or other generally round geometries. There are no sharp edges that can abrade the sutures when the suture slides relative to the post. Lofted surfaces 1066, seen in FIG. 57, may help ensure that there is a smooth transition between the eyelet 1064 and the edge of the head. The surface 1066 also tends to contain the sutures in the track created by the surface. The lofted surfaces 1066 are formed by the post 1065 gradually increasing in diameter from the center of the eyelet transversely towards the edges of the eyelet. As the diameter increases away from the center of the eyelet, the center of radius for the post shifts downward toward the threads of the anchor.

FIG. 58 is a cross-sectional side view of the suture anchor of FIG. 57. From this view, the post 1065 and the lofted surfaces which surround the post can be easily seen. As in FIG. 53, the cross-section of the lofted surfaces form circles from the base of the anchor head to the top of the post 1065. The cross-sectional area of the circles may vary in size, such that the area decreases in size from one transverse side of the screw to the middle of the eyelet at the long-axis of the suture anchor, and increases in size from the middle of the eyelet at the long-axis of the suture anchor to the other transverse side of the screw. While the illustrated embodiment shows the cross-section of the post 1065 and its lofted surfaces 1066 as being circular, the cross-section may vary in shape (e.g., it may be elliptical) so long as the lofted surfaces 1006 form a smooth, edgeless section that reduces the risk of suture abrasion.

FIG. 59 is a top view of the suture anchor of FIG. 57. The top view illustrates the suture head 1062 having portions that surround the eyelet hole 1064 and the post 1065, and which rests on collar 1063. The suture head 1062 comprises a rectangular top with which an anchor inserter may geometrically mate. The lofted surfaces 1066 have sweeping, curved features that extend from the top of the anchor head 1062 downwardly toward the eyelet 1064.

For suture anchor 1062, a modification of the anchor inserter 1041 may be used, with an alternative cavity to receive the anchor. In one embodiment, the cavity may receive the suture anchor 1060 via a sliding fit with the surfaces 1068. In some embodiments, there is no contact between the inserter and the anchor in the region of the indentations 1067, permitting the suture to be pulled within the central hole of the inserter and avoid contact between the inserter and the surfaces 1066. Like the suture anchor in FIG. 52, the suture anchor 1060 may contain one suture or multiple sutures, such as two, three, four, five or even more.

In a preferred embodiment, the surfaces 1066 of the head 1062 are produced to a high surface finish, such as appropriate for use on the metal articulation of total joint replacements (between 0.1 to 0.5 microns (Ra)). At the same time, the geometrical portion 1068 that mates with the inserter can be more roughly finished without impacting the articulation between the anchor and the suture.

The suture anchors of the present application can be composed of a variety of biocompatible materials, including metals (notably titanium alloys, nitinol alloys, Co—Cr alloys, stainless steels), polymers (PEEK, UHMWPE, Acetal, polylactic acid), composites (such as PEEK reinforced Carbon Fiber, hydroxyapatite-polyhydroxybutyrate composite material trademarked Biosteon®, and tricalcium phosphate-polylactic acid composites), allograft or xenograft bone.

While described as a suture anchor, the suture anchors of the present application could be used with a variety of relatively compliant structures besides or in addition to sutures, such as monofilament or multifilament wire, cable, weaves, braids or knits, including those manufactured of biocompatible metals, polymers or composites, including both resorbable and nonresorbable materials, and assemblies of the above structures.

Figure 60:
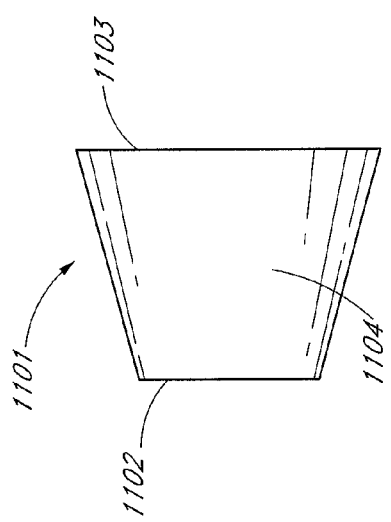
FIG. 60 is a side view of a suture plug according to one embodiment.

FIGS. 60-63 illustrate a novel suture plug 1101 for fixing one or more sutures in tension with a bony component, such as the spinous process. The suture plug 1101 has a leading end 1102 and a trailing end 1103. In some embodiments, one or both ends 1102 and 1103 may be circular in shape, thus making the outer surface 1104 of the suture plug a conic section. The leading end 1102 is generally smaller in diameter than the trailing end 1103 as shown in FIG. 60. Within the suture plug is a central cavity 1105. The central cavity is bridged by a strut 1106 at the trailing end 1103 of the suture plug. Two openings 1107 are formed from the combination of the central cavity 1105 and the strut 1106. The corners 1108 of the strut 1106 are radiused so as to remove sharp corners that may result in abrasion or fretting of the suture.

Methods are now described using the suture plug according to one embodiment. A machined cavity is formed within a bone, using drills, reamers and similar instruments, some of which may be contoured to match the outer surface 1104 of the suture plug. One or more ends of a suture, or other similarly compliant structure, may be pulled through the machined cavity in the bone. The suture ends are threaded through the central cavity 1105 of the suture plug 1101, from leading end 1102 towards trailing end 1103. If using two or more suture ends, ends are passed on opposite sides of the strut 1106. If using one suture end, it is passed fully around the strut and then out through the trailing end. The suture plug 1101 may then advance along the sutures until it is pressed into the machined cavity in the bone. The suture is tightened, perhaps with the aid of a tensioner. The suture ends are then tied off, preferably using knots. Alternatively, the suture ends could be crimped, welded or otherwise joined so as to fix the ends of the suture with respect to the suture plug.

In a preferred embodiment, the central cavity 1105 of the suture plug 1101 is sized to have contact with one or more sutures only on the strut 1106. That is, the suture plug may be preferably oriented in either a collinear alignment with the long axis of a suture anchor such as that shown in FIG. 57. In an alternative embodiment, the suture plug is oriented in a perpendicular alignment with the long axis of a suture anchor such as that shown in FIG. 52 and aligned with the eyelet 1004 of the anchor. In these orientations, the sutures will be aligned with the central axis of the suture plug, avoiding misalignment that could cause contact between the sutures and the suture plug that may result in wear, fretting or fatigue of either the suture or the suture plug and a potential diminution of the mechanical life of the system.

The suture plug could be formed of a variety of metal, polymeric or natural materials, as well as composites of these materials. These include permanent materials such as titanium alloys, nitinol alloys, Co—Cr alloys, stainless steels, PEEK, PEEK reinforced carbon fiber, UHMWPE, nylon and acetal. Alternatively, the suture plug could be formed of resorbable or partially resorbable materials such as polylactic acid (PLA), polyglycolic acid (PGA), autograft, allograft or xenograft bone, as well as composites such as hydroxyapatite-polyhydroxybutyrate composite material trademarked Biosteon®, tricalcium phosphate-polylactic acid composites or biocomposites that are composed of part natural materials and either mineral or polymer, such as Plexur™ marketed by Osteotech, Inc.

The suture anchors, anchor inserters and suture plugs of the present application could have use in a variety of orthopedic surgical applications, such as shoulder, knee or hip applications. Additionally, the suture anchors, anchor inserters and suture plugs of the present application could be used as elements in addition to those systems, methods and apparatuses described above that are related to torsionally resistive spinal implantation. For example, in one embodiment, the suture anchor of FIGS. 52-54 may be used, so that the pull of the suture, when directed towards the spinous process of the superior vertebral body, would be along a line generally 90 degrees with respect to the axis of the anchor. The suture plug would be used to fix the plug to the spinous process of the superior vertebral body.

FIG. 64A illustrates one embodiment of a suture anchor 1110 and a suture plug 1112 including a single suture 1114 according to one embodiment. FIG. 64B illustrates the same suture anchor 1110 and suture plug 1112 of FIG. 63A shown from a top view. The suture anchor 1110 shown in FIGS. 64A and 64B is similar to the suture anchor shown in FIG. 52, as it allows for a line of pull of a suture 1114 that is perpendicular to the long axis of the suture anchor 1110. As shown in FIG. 64A, the single suture 1114 wraps around a single post on only one side of the suture anchor 1110 and enters through an opening of the suture plug 1112 such that there is little to no surface area that may abrade the suture 1114. In another embodiment, one or more sutures in addition to suture 1114 may be wrapped around the same post of suture anchor 1110. In yet another embodiment, one or more sutures may be wrapped around a different post of the suture anchor 1110 if needed. These sutures would have a pull in the opposite direction of the suture 1114, and may also be connected to a suture plug.

Accordingly, a method is presented below that applies both the multi-functional instrument 1201 shown in FIG. 32C and a novel suture anchor and suture plug to provide torsional stabilization. One of skill in the art will appreciate that the method described below is only one of many methods in which the instrument 1201 may be used to limit axial torsion. Moreover, those skilled in the art will appreciate that the steps need not be performed in the exact order as described and may be performed in various orders to achieve similar results.

The method is described as follows:
1. A patient is positioned so that the anterior-posterior axis of a targeted disc space is oriented vertically. This alignment is optional; however, in some patients, it may be much easier to perform a surgery according to this alignment.
2. An incision is made over the spinous process of the superior vertebral body. The depth of the incision will vary depending on the area of the body to be treated.
3. The instrument 1201 may then be used to attach to the spinous process by using a clamping mechanism. In one embodiment, tines 1203 may be used to clamp on the sides of the spinous process. Alternatively, a bone clamp may be used that serves as a combination clamp and bone punch such that a hole may be created in the spinous process.
4. The instrument 1201 may then be held in a vertical position, matching the anterior-posterior axis of the disc space.
5. The skin is retracted laterally and a cavity is created in the spinous process. In a preferred embodiment, the tools used to make the cavity may be guided by the combination passing and anchor hole 1205 so as to ensure alignment of the cavity. The cavity may match the outer surface 1104 of the suture plug 1101.
6. Following creation of the cavity in the spinous process, a needle, dilator or cannula may be used to create a working channel from the incision to the desired location for fixing one or more suture anchors, such as 1060.
7. Using the cannula described above, a soft tissue anchor preloaded with one or more sutures, such as described above, may be implanted using an anchor inserter.
8. The anchor inserter and cannula is retracted out through the cavity in spinous process and out of the patient along with the free end(s) of the suture.
9. The instrument 1201 may then be removed.
10. The sutures may then be threaded through holes in a suture plug, such as described above, and the suture plug advanced in contact with the cavity created in the spinous process.
11. Knots may then be used to tighten the sutures to the suture plug, resulting in adequate tension in the sutures to limit axial torsion. In a preferred embodiment, two ends of a single suture are used as the stabilizing implant and are tied to each other after passing through the suture plug. Although in one embodiment, axial torsion is limited in a single direction, it may be possible to limit axial torsion in multiple directions using sutures of different orientation and by proper positioning of the combination passing and anchor holes so that the sutures and suture plugs do not interfere with each other.
12. The incisions may then be closed in a normal fashion.

While this invention has been particularly shown and described with reference to embodiments thereof, it will be understood by those skilled in the art that various changes in form and details may be made therein without departing from the scope of the invention. For all of the embodiments described above, the steps of the methods need not be performed sequentially.

It will be apparent to those skilled in the art that various modifications and variations can be made in the present invention without departing from the scope or spirit of the invention. Thus, it is intended that the present invention cover modifications and variations of this invention.

I claim:
1. A method for providing torsional stabilization to a spine, comprising:
extending an implant between a first vertebral body and a second vertebral body, the implant being attached to a fixation device rigidly fixed to a spinous process of the second vertebral body and extending laterally outwardly to attach to a location on the first vertebral body without penetrating a facet of the first vertebral body, wherein the fixation device does not engage the spinous process of the first vertebral body;

wherein the implant is fixed at a first fixation point to the first vertebral body and at a second fixation point to the second vertebral body, wherein the first and second fixation points and the implant lie substantially within the same plane parallel with a disc space between the first and second vertebral bodies, such that relative movement between the first fixation point and the second fixation point away from one another is resisted during axial rotation of the spine by tensioning the implant without contacting or fixing any apparatus to the spinous process of the first vertebral body.

2. The method of claim 1, wherein the implant is attached to a pedicle of the first vertebral body.

3. The method of claim 1, wherein the implant is attached to a mamillary process of the first vertebral body.

4. The method of claim 1, wherein the implant is attached to the location on the first vertebral body by a screw, staple, soft tissue anchor, suture anchor or adhesive.

5. The method of claim 1, wherein the implant comprises a polymeric surgical fabric, autograft soft tissue or allograft soft tissue.

6. The method of claim 1, wherein the implant comprises one or more sutures.

7. The method of claim 1, wherein the implant passes through a hole in the spinous process of the second vertebral body.

8. The method of claim 1, wherein the fixation device comprises a turnbuckle, an outrigger, a thimble, an endobutton or a suture plug.

9. The method of claim 1, wherein the implant is prevented from translating with respect to the fixation device at least during axial rotation of the spine in which the first fixation point and the second fixation point are moved away from one another.

10. The method of claim 1, further comprising using an anchor driver to secure an anchor to the location on the first vertebral body.

11. The method of claim 1, wherein relative movement between the first fixation point and the second fixation point away from one another is resisted unilaterally during axial rotation of the spine by tensioning the implant on a first lateral side of the spine without contacting or fixing any apparatus to the first vertebral body on a second lateral side of the spine opposite the first side.

12. The method of claim 1, wherein the first fixation point is located on a first vertebral body in the lumbar spine in a region from the pedicle superiorly and medially onto the mammillary process.

13. The method of claim 1, wherein the first fixation point is located on a first vertebral body at the sacrum.

14. The method of claim 1, wherein the first fixation point is located on a first vertebral body in the cervical spine on the lateral aspect of the superior articular process.

15. A method for providing torsional stabilization to a spine, comprising:
creating a hole through a spinous process of a superior vertebral body;
attaching a suture to a location on an inferior vertebral body without penetrating a facet of the inferior vertebral body;
extending the suture from the inferior vertebral body to the spinous process of the superior vertebral body without passing through the facet of the inferior vertebral body, the suture extending substantially within a plane parallel with a disc space between the superior and inferior vertebral bodies; and
securing the suture to the spinous process of the superior vertebral body via an endobutton secured adjacent to the hole in the spinous process, the suture being tensioned within said plane;
wherein after securing the suture to the spinous process, the entire length of the suture between the inferior vertebral body and the spinous process lies substantially within the plane parallel with the disc space between the superior and inferior vertebral bodies.

16. The method of claim 15, wherein the suture is attached to the location on the inferior vertebral body with a suture anchor.

17. The method of claim 16, wherein the suture anchor is preloaded with one or more sutures.

18. The method of claim 15, wherein the location on the inferior vertebral body comprises a pedicle of the inferior vertebral body.

19. The method of claim 15, wherein the suture is attached to the location on the inferior vertebral body before creating the hole through the spinous process.

20. The method of claim 15, further comprising using an instrument to pull the suture through the hole in the spinous process prior to securing the suture to the spinous process of the superior vertebral body via the endobutton.

21. The method of claim 15, further comprising threading the suture through one or more holes in the endobutton.

22. The method of claim 15, further comprising applying a knot to the suture.

23. The method of claim 15, further comprising using a tensioner to place the suture in tension.

24. A method for providing torsional stabilization to a spine, comprising:
extending a suture between an inferior vertebral body and a superior vertebral body, the suture being attached at a first fixation point to a first fixation device rigidly fixed to a spinous process of the superior vertebral body and at a second fixation point to a second fixation device rigidly fixed to a location on the inferior vertebral body located laterally outward from the first fixation point, the suture being placed under tension between the first fixation point and the second fixation point, wherein the first fixation device does not engage the spinous process of the inferior vertebral body;
wherein relative movement between the inferior vertebral body and the superior vertebral body is resisted unilaterally during axial rotation of the spine by tensioning the suture on a first lateral side of the spine between the first fixation point and the second fixation point without contacting or fixing any apparatus to the inferior vertebral body on a second lateral side of the spine opposite the first lateral side, without contacting or fixing any apparatus to the spinous process of the inferior vertebral body, and without extending the suture through the facet of the inferior vertebral body; and
wherein the first and second fixation points and the entire length of the suture being tensioned between the first and second fixation points lie within a plane parallel with the disc space between the superior and inferior vertebral bodies.

* * * * *